United States Patent [19]

Baker et al.

[11] Patent Number: 5,496,833
[45] Date of Patent: Mar. 5, 1996

[54] PIPERIDINE TACHYKININ RECEPTOR ANTAGONISTS

[75] Inventors: Reymond Baker, Much Hadham; Tamara Ladduwahetty, London; Eileen M. Seward, Bishops Stortford; Christopher J. Swain, Duxford, all of England

[73] Assignee: Merck Sharp & Dohme Limited, Hertfordshire, United Kingdom

[21] Appl. No.: 387,684

[22] Filed: Feb. 13, 1995

Related U.S. Application Data

[62] Division of Ser. No. 46,538, Apr. 13, 1993, Pat. No. 5,444,074.

[51] Int. Cl.$^6$ .................. A61K 31/445; C07D 401/06
[52] U.S. Cl. .................. 514/326; 514/327; 546/194; 546/209; 546/210
[58] Field of Search .................. 514/326, 327; 546/194, 209, 210

[56] References Cited

U.S. PATENT DOCUMENTS

| | | | |
|---|---|---|---|
| 3,560,510 | 2/1971 | Warawa | 546/133 |
| 3,833,592 | 3/1974 | Papanastassiou | 546/133 |
| 4,599,344 | 7/1986 | Morgan, Jr. | 514/305 |
| 4,843,047 | 6/1989 | Rzeszotorski et al. | 514/228.2 |

FOREIGN PATENT DOCUMENTS

| | | |
|---|---|---|
| 0394989 | 10/1990 | European Pat. Off. . |
| 0436334 | 7/1991 | European Pat. Off. . |
| 0533280 | 3/1993 | European Pat. Off. . |
| WO90/05729 | 5/1990 | WIPO . |

OTHER PUBLICATIONS

1982 Substance P in Symposium 91, pp. 13–34, by Otsuka, et al.
TIPS, vol. 8, pp. 506–510, 1987.
J. of Med. Chem., vol. 25, p. 1009 (1982), by B. Sandberg, et al.
Science, vol. 226, pp. 547–549 (1984), by Levine, et al.
Neuroscience, vol. 25, pp. 817–837 (1988), by Mantyh, et al.
"Trends in Cluster Headache", Elsevier Science Publ., p. 85 (1987), by E. Sicuteri, et al.
The Lancet (1989), by Kidd, et al.
J. of Rheumatology, vol. 15, pp. 1807–1810, by Gronblad, et al., (1988).
Arthritis & Rheumatism, vol. 33, pp. 1023–1028 (1990), by O'Byrne, et al.
Can. Jour. Pharmacol. Physiol., vol. 66, pp. 1361–1367 (1988), by Hamlet, et al.
Science, vol. 241, pp. 1218–1221 (1988), by Lotz, et al.
J. of Immunology, vol. 141, pp. 3564–3569 (1988), Kimball, et al.
PNAS, vol. 85, pp. 3235–3239 (1988), by Mantyh, et al.
Science, vol. 350, pp. 279–282 (1990), Yankner, et al.

*Primary Examiner*—Yogendra N. Gupta
*Attorney, Agent, or Firm*—J. Eric Thies; David L. Rose

[57] ABSTRACT

Compounds of formula (I), and salts and prodrugs thereof

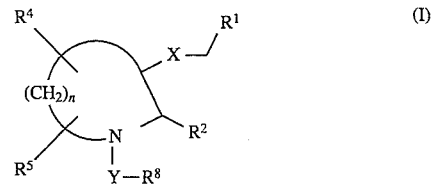

wherein
n is 1, 2 or 3;
X represents O or S;
Y represents a hydrocarbon chain of 1, 2, 3 or 4 carbon atoms optionally substituted by oxo;
$R^1$ is phenyl optionally substituted by 1, 2 or 3 of $C_{1-6}$alkyl, $C_{2-6}$alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$;
$R^2$ is phenyl, indazolyl, thienyl, furyl, pyridyl, thiazolyl, tetrazolyl, quinolyl, benzhydryl, or benzyl;
$R^4$ and $R^5$ each independently represent H, halo, $C_{1-6}$alkyl, oxo, $CH_2OR^a$, $CO_2R^a$ or $CONR^aR^b$;
$R^8$ represents an optionally substituted aromatic heterocycle; and
$R^a$ and $R^b$ are H, trifluoromethyl, $C_{1-6}$alkyl or phenyl optionally substituted by $C_{1-6}$alkyl, halo or trifluoromethyl;
are tachykinin antagonists useful in medicine.

12 Claims, No Drawings

PIPERIDINE TACHYKININ RECEPTOR ANTAGONISTS

This is a division of application Ser. No. 08/046,538, filed Apr. 13, 1993, now U.S. Pat. No. 5,444,074.

This invention relates to a class of azacyclic compounds, which are useful as tachykinin antagonists. More particularly, the compounds of the invention comprise an azacyclic ring system substituted by an arylmethyloxy or arylmethylthio moiety.

The tachykinins are a group of naturally-occurring peptides found widely distributed throughout mammalian tissues, both within the central nervous system and in the peripheral nervous and circulatory systems. The three known mammalian tachykinins are as follows:
Substance P,
Neurokinin A, and
Neurokinin B.

For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009; S. L. Shepheard et al., Br. J. Pharmacol. (1993), 108, 11–12) and in arthritis [Levine et al in Science (1984) 226 547–549]. These peptides have also been implicated in gastrointestinal (GI) disorders and diseases of the GI tract such as tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33–1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9] vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al Science, (1990) 250, 279–82] in senile dementia of the Alzheimer type, Alzheimer's disease and Down's Syndrome.

Substance P may also play a role in demyelinating diseases such as multiple sclerosis and amyotrophic lateral sclerosis [J. Luber-Narod et. al., poster presented at C.I.N.P. XVIIIth Congress, 28th Jun.-2nd Jul., 1992], and in disorders of bladder function such as bladder detrusor hyperreflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), ophthalmic disease such as conjuctivitis, vernal conjunctivitis, and the like, and cutaneous diseases such as contact dermatitis, atropic dermatitis, urticaria, and other eczematoid dermatitis (European patent application no. 0 394 989) and emesis (European patent application no. 0 533 280).

In view of their metabolic instability, peptide derivatives are likely to be of limited utility as therapeutic agents. It is for this reason that non-peptide tachykinin antagonists are sought.

European patent application no. 0 436 334 discloses 4- to 7-membered azacyclic compounds substituted at the 3-position by a substituted amino moiety. The compounds are said to be tachykinin antagonists.

The present invention provides a compound of formula (I), or a salt or prodrug thereof:

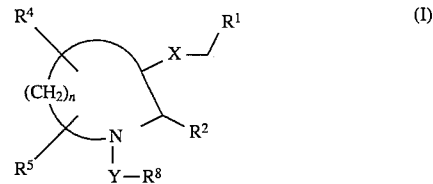

wherein n is 1, 2 or 3;

X represents O or S;

Y represents a hydrocarbon chain of 1, 2, 3 or 4 carbon atoms which may optionally be substituted by oxo;

$R^1$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, $—OR^a$, $SR^a$, $SOR^a$, $SO_2R^a$, $—NR^aR^b$, $—NR^aCOR^b$, $—NR^aCO_2R^b$, $—CO_2R^a$ or $—CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ may be present on any available carbon atom of the azacyclic ring and each independently represent H halo, $C_{1-6}$alkyl oxo, $CH_2OR^a$, $CO_2R^a$ or $CONR^aR^b$;

$R^8$ represents an optionally substituted aromatic heterocycle; and $R^a$ and $R^b$ each independently represent H, trifluoromethyl, $C_{1-6}$alkyl or phenyl optionally substituted by $C_{1-6}$alkyl, halo or trifluoromethyl.

As used herein, the definition of each expression, when it occurs more than once in any structure, is intended to be independent of its definition elsewhere in the same structure.

The alkyl, alkenyl and alkynyl groups referred to with respect to the above formula may represent straight, branched or cyclic groups, or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. In particular, the relative orientation of the 2- and 3-substituents on the azacyclic ring may give rise to cis and trans diastereoisomers, of which the cis stereochemistry is preferred. It is to be understood that all such isomers and mixtures thereof are encompassed within the scope of the present invention.

Preferably n is 2 or 3, more preferably 3.

Preferably X represents O.

Suitably Y represents a hydrocarbon chain of 1 or 2 carbon atoms optionally substituted by oxo, such as $CH_2$, $C=O$, $CH(CH_3)$, $CH_2(C=O)$ or $(C=O)CH_2$. Preferably Y represents $CH_2$, $CH(CH_3)$ or $CH_2(C=O)$, more preferably $CH_2$ or $CH(CH_3)$. A particularly preferred subgroup of compounds according to the invention is represented by compounds of formula (I) wherein Y is $CH(CH_3)$.

Preferably $R^1$ represents substituted phenyl. When $R^1$ is substituted phenyl suitable substituents include nitro, trifluoromethyl, trimethylsilyl, bromo, chloro, fluoro, iodo, cyano, $C_{1-6}$alkyl such as methyl, ethyl, i-propyl, i-butyl, t-butyl and cyclopropyl, $C_{2-6}$alkenyl such as vinyl, $C_{1-6}$alkoxy such as methoxy, ethoxy and i-propoxy, phenoxy, amino, carboxamido and carbonylmethoxy. Preferably $R^1$ represents phenyl substituted by one or more groups selected from $C_{1-4}$alkyl, such as methyl and t-butyl, trifluoromethyl and halo such as iodo, bromo chloro and fluoro.

Suitably $R^1$ represents monosubstituted phenyl, such as 3-substituted phenyl or, preferably, disubstituted phenyl, such as 3,5-disubstituted phenyl. Preferably $R^1$ represents phenyl substituted at the 3-position by trifluoromethyl or a $C_{1-6}$alkyl group such as t-butyl, or 3,5-disubstituted phenyl wherein the substituents are independently selected from trifluoromethyl, chloro, fluoro, methyl and t-butyl. Preferred values for $R^1$ include 3,5-bis(trifluoromethyl)phenyl, 3,5-dichlorophenyl, 3-t-butyl-5-methylphenyl, 3-chloro-5-methylphenyl, 3-t-butyl-5-chlorophenyl, 3-bis(trifluoromethyl)phenyl and 3-t-butylphenyl. Particularly preferred is 3,5bis(trifluoromethyl)phenyl.

Suitably $R^2$ represents benzhydryl or optionally substituted phenyl, such as phenyl optionally substituted by halo such as fluoro or chloro, preferably in the 3-position. Preferably $R^2$ represents unsubstituted phenyl or unsubstituted benzhydryl, more preferably unsubstituted phenyl.

Suitable values for $R^4$ and $R^5$ include H, $C_{1-6}$alkyl, especially methyl, hydroxymethyl and oxo. The substitutents $R^4$ and $R^5$ may be located on any available carbon atom of the azacyclic ring including, except in the case where the substituent $R^4$ or $R^5$ in question represents oxo, C-2 and C-3. Preferably at least one of $R^4$ and $R^5$ represents H. In one preferred group of compounds $R^4$ and $R^5$ both represent H. In a further preferred group of compounds one of $R^4$ and $R^5$ is H and the other of $R^4$ and $R^5$ is methyl, preferably 2-methyl.

When $R^8$ represents a substituted aromatic heterocycle, suitable substituents in the heterocyclic ring include one or more of $C_{1-6}$alkyl, $C_{1-6}$alkoxy, phenol, oxo, thioxo, halo, trifluoromethyl, $NR^aR^b$, $NR^aCOR^b$, $CONR^aR^b$, $CO_2R^a$, $SR^a$, $SO_2R^a$ and $CH_2OR^a$, where $R^a$ and $R^b$ are as previously defined. Particular examples of suitable substituents include methyl, methoxy, phenyl, oxo, thioxo, bromo, iodo, $NH_2$, $SCH_3$, $CONH_2$ and cyano. Particularly preferred substituents include oxo and $NH_2$.

Suitable values for $R^8$ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted.

In particular, $R^8$ may represent optionally substituted thienyl, furyl, pyridyl, triazolyl, tetrazolyl, thiazolyl, pyrazinyl, pyrimidinyl, pyridazinyl, triazinyl, oxazolyl, oxadiazolyl, thiadiazolyl, imidazolyl, benzimidazolyl or benzoxazolyl.

In one group of compounds according to the invention $R^8$ represents optionally substituted pyrrolyl, pyrazolyl, pyrazinyl, pyrimidinyl, pyridazinyl, triazinyl, oxadiazolyl, thiadiazolyl, imidazolyl, benzimidazolyl, benzoxazolyl, benzothiophenyl, benzofuranyl or indolyl.

Preferably $R^8$ represents a substituted or unsubstituted 5- or 6-membered nitrogen containing aromatic heterocycle such as for example oxazolyl, oxadiazolyl, tetrazolyl, thiazolyl, thiadiazolyl, triazolyl, pyrazinyl, pyridyl, pyrimidinyl, pyridazinyl, imidazolyl or triazinyl. More preferably $R^8$ represents optionally substituted oxazolyl, oxadiazolyl, imidazolyl, thiadiazolyl, triazolyl, pyrazinyl, pyrimidinyl, pyridazinyl or triazinyl, or tetrazolyl substituted by $C_{1-6}$alkyl, preferably methyl.

In one preferred group of compounds according to the invention, $R^8$ represents substituted or unsubstituted oxadiazolyl, for example, oxadiazolyl substituted by halo, amino, dialkylamino or methyl. More preferably $R^8$ represents 5-(3-aminooxadiazolyl).

In a further preferred group of compounds according to the invention, $R^8$ represents substituted or unsubstituted triazolyl, for example, unsubstituted triazolyl or triazolyl subtituted by oxo or thioxo, more preferably, triazolyl substituted by oxo.

It will be appreciated that, when the heterocyclic moiety $R^8$ is substituted by an oxo or thioxo substituent, different tautomeric forms are possible so that the substituent may be represented as $=O$ or $-OH$, or $=S$ or $-SH$, respectively. For the avoidance of doubt, all such tautomeric forms are embraced by the present invention.

One subgroup of compounds according to the invention is represented by compounds of formula (IA), and salts and prodrugs thereof:

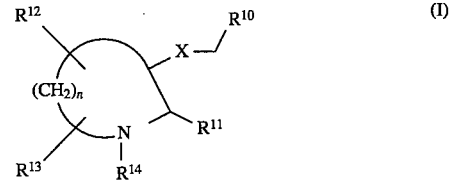

(I)

wherein n is 1, 2 or 3 and where any carbon atom of $(CH_2)_n$ may be substituted by $R^{12}$ and/or $R^{13}$;

X represents O or S;

$R^{10}$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, $-OR^c$, $SR^c$, $SOR^c$, $SO_2R^c$, $-NR^cR^d$, $-NR^cCOR^d$, $-NR^cCO_2R^d$, $-CO_2R^c$ or $-CONR^cR^d$;

$R^{11}$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^{12}$ and $R^{13}$ each independently represent H, halo, $C_{1-6}$alkyl, oxo, $CO_2R^c$ or $CONR^cR^d$;

R14 represents $C_{1-4}$alkyl, optionally substituted by oxo, substituted by an optionally substituted aromatic heterocycle; and $R^c$ and $R^d$ each independently represent H, $C_{1-6}$alkyl, phenyl optionally substituted by $C_{1-6}$alkyl or halo or trifluoromethyl.

Suitable values for the heterocyclic moiety of $R^{14}$ include thienyl, furyl, pyrrolyl, pyridyl, pyrazolyl, triazolyl, tetrazolyl, thiazolyl, pyrazinyl, pyridazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl.

In one sub-class of compounds of formula (IA), $R^c$ and $R^d$ each independently represent H, $C_{1-6}$alkyl, phenyl or trifluoromethyl.

A further subclass of compounds of formula (IA) is represented by compounds wherein n is 2 or 3; $R^{12}$ and $R^{13}$ each independently represent H, halo, $C_{1-6}$alkyl, $CO_2R^c$ or $CONR^cR^d$; $R^{14}$ represents $C_{1-4}$alkyl substituted by an optionally substituted 5- or 6-membered aromatic heterocycle; and $R^c$ and $R^d$ each independently represent H, $C_{1-6}$alkyl, phenyl or trifluoromethyl. For the compounds of this subclass, suitable values for the heterocyclic moiety of $R^{14}$ include thienyl, furyl, pyrrolyl, pyridyl, pyrazolyl, triazolyl, tetrazolyl, thiazolyl, oxazolyl, oxadiazolyl, thiadiazolyl, isoxazolyl, isothiazolyl and imidazolyl.

A preferred sub-class of compounds according to the invention is represented by compounds of formula (IB), and salts and prodrugs thereof:

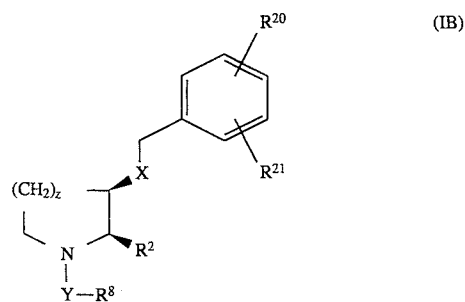

(IB)

wherein

X represents O or S, preferably O;

Y is as defined for formula (I), preferably $C_{1-2}$alkyl optionally substituted by oxo, more preferably $CH_2$ or $CH(CH_3)$;

$R^2$ represents phenyl or benzhydryl wherein any of the phenyl rings of the phenyl or benzhydryl moieties may optionally be substituted by halo or trifluoromethyl, preferably unsubstituted phenyl;

$R^8$ is as defined for formula (I); and $R^{20}$ and $R^{21}$ independently represent H, $C_{1-6}$alkyl, $C_{2-6}$alkenyl, $C_{2-6}$alkynyl, bromo, chloro, fluoro, iodo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$, or $CONR^aR^b$, where $R^a$ and $R^b$ are as previously defined; and z is 1 or 2.

Particular values of $R^{20}$ and $R^{21}$ include H, methyl, t-butyl, methoxy, i-propoxy, chloro, fluoro, nitro, amino, carbonylmethoxy, carboxamido and trifluoromethyl. Preferably $R^{20}$ and $R^{21}$ are both other than H, more preferably $C_{1-6}$alkyl, halo or trifluoromethyl, and are located at the 3- and 5-positions of the phenyl ring.

One sub-class of compounds according to the invention are compounds of formula (IB) wherein $R^8$ is optionally substituted pyrrolyl, pyrazolyl, pyrazinyl, pyrimidinyl, pyridazinyl, triazinyl, imidazolyl, benzimidazolyl, benzoxazolyl, benzothiophenyl, benzofuranyl, indolyl, thiadiazolyl or oxadiazolyl, more preferably oxadiazolyl.

A further sub-class of compounds according to the invention are compounds of formula (IB) wherein $R^8$ is optionally substituted oxadiazolyl, pyridinyl, benzimidazolyl, tetrazolyl, thiazolyl, furyl, thienyl, triazolyl, thiadiazolyl, benzoxazolyl, oxazolyl, pyrazinyl, pyridazinyl, triazinyl, pyrimidinyl or imidazolyl.

A particularly preferred group of compounds according to the invention are compounds of formula (Ia) wherein $R^8$ is optionally substituted triazolyl, especially triazole substituted by oxo.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalciumphosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of-the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure-breathing machine. Solution, suspension or powder compositions may be administered, preferably orally or nasally, from devices which deliver the formulation in an appropriate manner.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, bronchopneumonia, chronic bronchitis, cystic fibrosis and asthma, and bronchospasm; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg of a compound of formula (I) per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

According to one general process (A), the compounds according to the invention may be prepared by a process which comprises reacting a compound of formula (II):

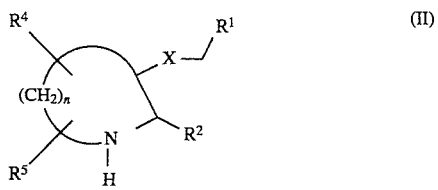

wherein $R^1$, $R^2$, $R^4$, $R^5$, X and n are as defined for formula (I) above, with a reagent suitable to introduce the group Y-$R^8$, for example, a halide or acyl halide, or corresponding mesylate or tosylate, of formula $R^8$-Y-L, where L represents halo, such as chloro, bromo or iodo, methylsulphonate or p-toluenesulphonate, or any other suitable leaving group, in the presence of a base.

Suitable bases of use in the reaction include inorganic bases such as alkali metal carbonates, for example, potassium carbonate.

Conveniently the reaction is effected in a suitable organic solvent, for example, dimethylformamide.

According to a second process (B), compounds of formula (I) wherein $R^8$ -represents 5-oxadiazolyl may be prepared by reaction of a compound of formula (III) with a compound of formula (IV):

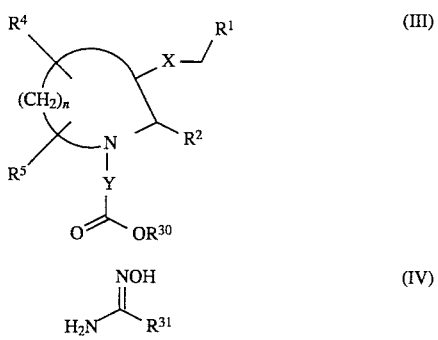

wherein $R^1$, $R^2$, $R^4$, $R^5$, X, Y and n are as defined for formula (I), $R^{30}$ represents an alkyl group and $R^{31}$ represents H or a suitable substituent such as $C_{1-6}$alkyl, $C_{1-6}$alkoxy, halo, $NR^aR^b$ or $NR^aCOR^b$, where $R^a$ and $R^b$ are as previously defined, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

According to a further process, (C), compounds of formula (I) wherein $R^8$ represents tetrazolyl may be prepared from intermediates of formula (V):

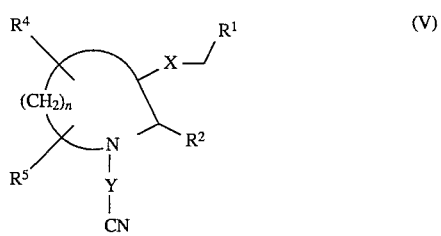

wherein $R^1$, $R^2$, $R^4$, $R^5$, X, Y and n are as defined for formula (I) by treatment with an alkali metal azide, such as sodium azide.

The reaction is conveniently effected in a high boiling organic solvent, such as, for example, N-methylpyrrolidinone.

According to a further process, (D), compounds of formula (I) wherein $R^8$ represents thiazolyl may be prepared from intermediates of formula (VI):

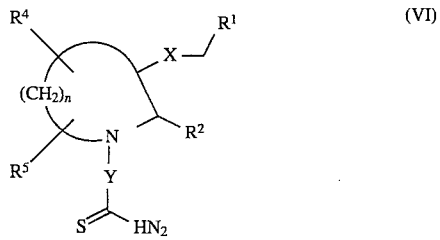

wherein $R^1$, $R^2$, $R^4$, $R^5$, X, Y and n are as defined for formula (I), by reaction with a compound of formula Hal-$CH_2C(O)$-$R^{60}$, where Hal represents halo such as bromo, chloro or iodo, and $R^{60}$ represents H or a suitable substituent such as $C_{1-6}$alkyl.

The reaction is conveniently effected in a suitable organic solvent, such as a ketone, for example, acetone, or an alcohol, for example, methanol, or a mixture of solvents, preferably at elevated temperature, such as the reflux temperature of the chosen solvent.

According to a futher process, (E), compounds of formula (I) wherein $R^8$ represents thioxotriazolyl may be prepared from intermediates of formula (VII)

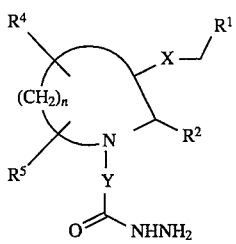

(VII)

wherein $R^1$, $R^2$, $R^4$, $R^5$, X, Y and n are as defined for formula (I), by reaction with a compound of formula $R^{61}$NCS, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable orgainc solvent, such as alcohol, e.g. butanol.

According to a further process, (F), compounds of formula (I) wherein $R^8$ represents unsubstituted or substituted triazolyl may be prepared by reaction of intermediates of formula (II) with a compound of formula (VIII):

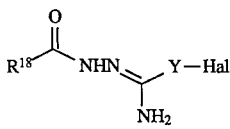

(VIII)

wherein Y and Hal are as previously defined and $R^{18}$ is H or a group suitable as a substituent of the triazole ring, or convertible to such a group under the reaction conditions, in the presence of a base.

Suitable bases of use in the reaction include alkali metal carbonates, such as, for example, potassium carbonate.

Suitably $R^{18}$ represents H, $OCH_3$ (which is converted to an oxo substituent under the reaction conditions) or $CONH_2$.

The reaction is conveniently effected in an anhydrous organic solvent, such as, for example, anhydrous dimethylformamide, preferably at elevated temperature, such as about 140° C.

According to a further process, (G), compounds of formula (I) wherein $R^8$ represents substituted or unsubstituted 1,3,5-triazine may be prepared by reaction of intermediates of formula (IX):

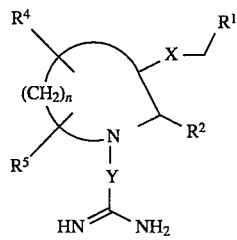

(IX)

wherein $R^1$, $R^2$, $R^4$, $R^5$, X, Y and n are as defined for formula (I), with substituted or unsubstituted 1,3,5-triazine.

The reaction is conveniently effected in a suitable organic solvent, such as acetonitrile, at elevated temperature, such as 80°–90° C., preferably about 82° C.

According to a further process, (H), compounds of formula (I) wherein $R^8$ represents substituted or unsubstituted 1,2,5-triazine may be prepared by reaction of an intermediate of formula (X) with a dicarbonyl compound of formula (XI):

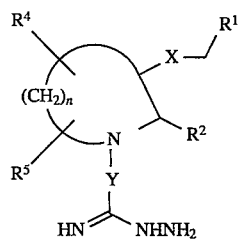

(X)

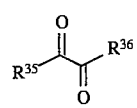

(XI)

wherein $R^1$, $R^2$, $R^4$, $R^5$, X, Y and n are as defined for formula (I) and $R^{35}$ and $R^{36}$ each independently represnt H or a suitable substituent such as $C_{1-6}$alkyl, e.g. methyl.

The reaction is conveniently effected in a suitable organic solvent, such as an ether, e.g. tetrahydrofuran, conveniently at ambient temperature.

Further details of suitable procedures will be found in the accompanying Examples.

Compounds of formula (VIII) may be prepared as described in *J. Med. Chem*, 27, (1984), 849.

Compounds of formula (I) may also be prepared from other compounds of formula (I) using suitable interconversion procedures. For example, compounds of formula (I) wherein Y-represents $C_{1-4}$alkyl substituted by an aromatic heterocycle may be prepared from compounds of formula (I) wherein Y represents $C_{1-4}$alkyl substituted by oxo by reduction, for example, using borane. Suitable interconversion procedures are described in the accompanying Examples, or will be readily apparent to those skilled in the art.

Intermediates of formula (III) may be prepared from intermediates of formula (II) by reaction with a compound of formula Hal-Y-$CO_2R^{30}$, where Hal represents halo such as chloro, bromo or iodo and $R^{30}$ and Y are as above defined, in the presence of a base. Suitable bases include tertiary amines, for example, triethylamine. Conveniently the reaction is effected in a suitable organic solvent, such as an ether, for example, tetrahydrofuran, at elevated temperature, such as the reflux temperature of the solvent.

Intermediates of formula (IV) are commercially available or may be prepared from commercially available materials by conventional procedures well-known to those skilled in the art.

Intermediates of formula (II) may be prepared as described in published European patent application no. 528 495.

Intermediates of formula (V) may be prepared from intermediates of formula (II) by reaction with a compound of formula Hal-Y-CN, wherein Hal is halo such as bromo, chloro or iodo and Y is as previously defined.

Intermediates of formula (VI) may be prepared from intermediates of formula (V) by treatment with an alkylthioamide, such as, for example, thioacetamide.

Intermediates of formula (VII) may be prepared from intermediates of formula (III) by treatment with hydrazine. The reaction is conveniently effected in a suitable organic solvent, such as an alcohol, for example, ethanol, at elevated temperature.

Intermediates of formula (IX) may be prepared from intermediates of formula (II) by reaction with a compound of formula Hal-Y-C(NH)$NH_2$, where Hal and Y are as previously defined.

Intermediates of formula (X) may be prepared from intermediates of formula (II) by reaction with a compound of formula Hal-Y-C(NH)NHNH-Boc, wherein Hal and Y are as previously defined and Boc stands for t-butoxycarbonyl, followed by deprotection under acidic conditions.

Compounds of formula (XI) are commercially available or may be prepared from commercially available compounds by known methods.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, any suitable intermediates may be resolved into their component enantiomers by standard techniques, such as the formation of diastereomeric esters or amides, followed by chromatographic separation or separation by fractional crystallization and removal of the chiral auxiliary. The diastereomeric intermediates can then be used to prepare optically pure compounds of formula (I).

During any of the above synthetic sequences it may be necessary and/or desirable to protect sensitive or reactive groups on any-of the molecules concerned. This may be achieved by means of-conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of Examples 1–10, for example, were found to have $IC_{50}$ values less than 500 nM.

DESCRIPTION 1 cis-3-((3,5-Bis(trifluoromethyl)phenyl)methyloxy)-2-phenylpiperidine Hydrochloride Salt a) A solution of methyl 4-nitrobutyrate (23 g) and benzaldehyde (16 ml) in acetic acid (39 ml) containing ammonium acetate (12.12 g) was heated at reflux under nitrogen for 2 h. The reaction mixture was cooled to 5° C., whereby a pale-yellow solid crystallised. This was isolated by filtration, then dissolved in dichloromethane, washed cautiously with saturated aqueous sodium bicarbonate solution (2 x), then dried ($MgSO_4$) and concentrated to leave a yellow solid. Recrystallisation from ethyl acetate provided 5-nitro-2-oxo-6-phenylpiperidine (12.5 g) as a crystalline, white solid. $^1H$ NMR ($CDCl_3$) d 7.46–7.26 (m), 6.0 (br s), 5.24 (dd, J=1.4, 7.0 Hz), 4.70 (m), 2.70–2.50 (m), 2.38–2.24 (m).

b) Potassium t-butoxide (1.68 g) was added to a solution of 5-nitro-2-oxo-6-phenylpiperidine (3 g) in a mixture of dichloromethane (50 ml) and methanol (50 ml) and the mixture was cooled to −78° C. under nitrogen. Ozone was bubbled through the solution for 3 h. A yellow-green solution resulted, and TLC indicated no starting material remained. The reaction mixture was purged with oxygen for 5 min to remove excess ozone, then dimethylsulfide (7 ml) was added and the reaction mixture was allowed to warm to 23° C. The solvent was removed in vacuo, and the residue was partitioned between dichloromethane and water. The layers were separated, and the aqueous phase was extracted twice with dichloromethane. The combined organic extracts were washed with brine, then dried ($K_2CO_3$) and concentrated to leave a yellow solid.

This crude material was slurried in dry tetrahydrofuran and added to lithium aluminium hydride (1M in THF, 50 ml) then heated at reflux for 12 h. After cooling to 23° C., the reaction mixture was quenched by the cautious addition of water (dropwise) under nitrogen, then 2M sodium hydroxide. The mixture was filtered through a pad of Hyflo, the flitrate was washed with brine, then dried ($K_2CO_3$) and concentrated to leave a yellow solid. Purification by silicagel chromatography ($CH_2Cl_2$/MeOH/$NH_3$ 97:3:1 then $CH_2Cl_2$/MeOH 95:5) provided 3-hydroxy-2-phenylpiperidine as a ca 4:1 mixture of cis- and trans-isomers respectively. $^1H$ NMR ($CDCl_3$) 7.44–7.20 (m), 3.84 (2), 3.76 (s), 3.54 (m), 3.4 (s), 3.3 (d, J=8 Hz), 3.26 (m), 3.04 (m) 2.78 (ddd, J=2.9, 11.9, 11.9 Hz), 2.70 (ddd, J=2.9, 11.9, 11.9 Hz), 2.18–1.78 (m), 1.48 (m). MS (EI) m/z 177 ($M^+$).

c) Di-t-butyldicarbonate (1.36 g) was added to a solution of 3-hydroxy-2-phenylpiperidine (1 g) in dichloromethane (8 ml) under nitrogen and the mixture stirred at 23° C. for 3 h. The solvent was removed in vacuo, and the residue purified by silica-gel chromatography ($CH_2Cl_2$/MeOH/$NH_3$ 97:3:0.5) to provide cis- and trans-1-t-butyloxycarbonyl-3-hydroxy-2-phenylpiperidine (1.4 g) as a clear, viscous oil. $^1H$ NMR ($CDCl_3$) d 7.50–7.42 (m), 7.40–7.14 (m), 5.36 (d, J=5.6 Hz), 4.50 (m), 4.44 (m), 4.12–3.92 (m), 3.02 (ddd, J=3.0, 12.5, 12.5 Hz), 2.87 (ddd, J=3.0, 12.5, 12.5 Hz), 1.88–1.66 (m), 1.46 (s), 1.36 (s).

d) To a cooled (0° C.) solution of 1-t-butyloxycarbonyl-3-hydroxy-2-phenylpiperidine (1.4 g) in dry dimethylformamide (5 ml) was added sodium hydride (80% dispersion in mineral oil; 182 mg). The cooling bath was removed and the reaction mixture stirred at 23° C. for 30 min. A solution of 3,5-bis(trifluoromethyl)benzyl bromide (1.87 g) in dry dimethylformamide (1 ml) was added and stirring was continued for 2 h at room temperature. The mixture was diluted with water (100 ml) and extracted with ethyl acetate (3×40 ml). The combined organic extracts were washed with brine (1×30 ml), dried ($MgSO_4$) and evaporated to yield a pale yellow oil. Purification by chromatography on silica using gradient elution of hexane in ethyl acetate (9:1–4:1) afforded the product cis-1-t-butyloxycarbonyl-3-((3,5-bis(trifluoromethyl)phenyl)methyloxy)-2-phenylpiperidine (350 mg) as an oil. $^1H$ NMR (250 MHz, $CDCl_3$) d 7.77 (1H, s, ArH), 7.71 (2H, s, ArH), 7.53–7.57 (2H, m, ArH), 7.2–7.4 (3H, m, ArH), 5.70 (1H, br d, app. J=7.0 Hz, NCHPh), 4.73 (2H, brs, $OCH_2$), 3.84–3.98 (2H, m, NCHCHO+NCHH), 2.77 (1H, ddd, J=13.0, 13.0, 3.0 Hz), NCHH̲), 2.00 (2H, mc, $CH_2$), 1.6–1.8 (2H, m, $CH_2$), 1.40 (9H, s, $C(CH_3)_3$).

e) Trifluoroacetic acid (3 ml) was added to the product of (d) above (800 mg) under nitrogen and the resulting solution was stirred for 1 h. Excess trifluoroacetic acid was removed in vacuo and the residue was partitioned between 2M sodium hydroxide and dichloromethane. The organic phase was washed with brine, dried ($MgSO_4$) and evaporated to afford a colourless oil. Purification on silica (dichloromethane in methanol, 98:2–95:5) afforded the product cis-3-((3,5-bis(trifluoromethyl)phenyl)methyloxy)-2-phenylpiperidine (360 mg) as a colourless oil. $^1H$ NMR (360 MHz, $CDCl_3$) d 7.78 (1H, s, ArH), 7.44 (2H, s, ArH), 7.18–7.38 (5H, s, ArH), 4.52 (1H, d, J=12.5 Hz, OCHH̲), 4.13 (1H, d, J=12.5 Hz, OCHH), 3.84 (1H, d, J=1.0 Hz, NCHPh), 3.68 (1H, d, J=1.5 Hz), 3.28 (1H, m, NCHCHO), 2.84 (1H, ddd, J=3.0, 12.5, 12.5 Hz, NCHH), 2.20 (1H, mc, NCHH), 1.8–1.98 (2H, m, CH$_2$), 1.64–1.78 (1H, m, CHH), 1.50–1.58 (1H, m, CHH); MS m/z 404 ((M+1)$^+$, 90%).

The oil was dissolved in ether to which was added excess ethereal hydrogen chloride. Upon standing a white solid crystallised. This was filtered and recrystallised from ethyl acetate-methanol to afford the title compound as white crystals: mp 200°–203° C. $^1$H NMR (360 MHz, DMSO) d 7.95 (1H, s, ArH), 7.81 (2H, s, ArH), 7.37–7.47 (5H, m, ArH), 4.78 (1H, d, J=13.0 Hz, OCHH), 4.56 (1H, s, NCHPh), 4.32 (1H, d, J=13.0 Hz, OCHH), 3.96 (1H, s, NCHCHO), 3.10 (1H, t, J=13.0 Hz, NCHH), 2.23 (1H, d, J=13.0 Hz, NCHH), 1.64–2.00 (4H, m, CH$_2$ ×2); MS (CI$^+$) m/z 404 ((M+1)$^+$, 90%); Found: C, 54.08;H, 4.47; N, 3.13. Calcd. for C$_{20}$H$_{20}$F$_6$NOCl.0.25H$_2$O: C, 54.06; H, 4.65; N, 3.15%.

DESCRIPTION 2

(2R*,3R*)-3-((3,5-Bis(trifluoromethyl)phenyl) methyloxy)-1-(carbomethoxy)methyl-2-phenylpiperidine cis-3-((3,5-Bis(trifluoromethyl)phenyl)methyloxy)-2-phenylpiperidine hydrochloride (Description 1, 1 g) was liberated from the hydrochloride salt by partitioning between ethyl acetate and 2M sodium hydroxide. The organic phase was washed successively with water, saturated brine, dried (MgSO$_4$) and evaporated in vacuo. To a solution of the residual oil in tetrahydrofuran (20 ml) was added triethylamine (0.4 ml) and methyl bromoacetate (400 mg) and the solution was heated at reflux under an atmosphere of nitrogen for 16 h. To the cooled solution was added ethyl acetate and water and the organic phase washed further with water and dried (MgSO$_4$). After the solvent had been removed in vacuo the residue was chromatographed on silica gel eluting with ethyl acetate/petroleum ether (3:10). The product was recrystallised from diethyl ether/petroleum ether to give the title compound: mp 81°–83° C. Found: C, 57.35; H, 4.98; N, 2.84; C$_{23}$H$_{23}$F$_6$NO$_3$.0.1(H$_2$O) requires C, 57.71; H, 4.86; N, 2.93%. MS (CI$^+$) m/z 476 (M+H)$^+$.

DESCRIPTION 3

(+)-(2S,3S)-cis-3-((3,5-Bis(trifluoromethyl)phenyl)methyloxy)-2-phenylpiperidine Hydrochloride Salt a) The mixture of cis- and trans-isomers of 3-hydroxy-2-phenylpiperidine (Description 1, (2b)) and 4-toluenesulfonic acid monohydrate was crystallized from methanol/ethyl acetate to give cis-3-hydroxy-2-phenylpiperidinium tosylate: mp 266°–267° C.

b) The tosylate salt (Description 3(a) above) was dissolved in a mixture of ethyl acetate and 10% aqueous Na$_2$CO$_3$ with warming. The organic phase was washed with saturated brine, dried (K$_2$CO$_3$) and evaporated to give crystalline cis-3-hydroxy-2-phenylpiperidine, mp 110°–110.5° C.

c) cis-3-Hydroxy-2-phenylpiperidine (Description 3b) and (−)dibenzoyltartrate were dissolved in methanol and crystallized by addition of ethyl acetate. The solid was recrystallised from hot methanol to give the hemi dibenzoyltartrate salt: mp 223°–224° C. This was liberated from the salt as described above to give the single enantiomer (+)-cis-3-hydroxy-2-phenylpiperidine, mp 93°–95° C. [a]$^{23}_D$=+98.5° (c=1, MeOH). The mother liquors were converted to the free base as described in Description 3b and crystallization using (+)dibenzoyltartrate in an analogous manner to that described above gave (−)-3-hydroxy-2-phenylpiperidine, mp 93°–95° C. [a]$^{23}_D$=−97.2° (c=1, MeOH).

d) (+)-cis-3-Hydroxy-2-phenylpiperidine was reacted according to the procedure detailed in Description 1c-e to give (+)-cis-3-((3,5-bis(trifluoromethyl)phenyl)methyloxy-2-phenylpiperidine hydrochloride as a crystalline solid: mp 215°–216° C. [a]$_D$=+87.3° (c=1, MeOH). $^1$H NMR (360 MHz, DMSO-d$_6$) d 7.95 (1H, s, ArH), 7.81 (1H, s, ArH), 7.47 (2H, m, ArH), 7.37 (3H, m, ArH), 4.78 (1H, d, J=13.0 Hz, OCHH), 4.56 (1H, s, NCHPh), 4.32 (1H, d, J=13.0 Hz, OCHH), 3.96 (1H, s, NCHCHO), 3.10 (1H, t, J=13.0 Hz, NCHH), 2.23 (1H, d, J=13.0 Hz, NCHH), 2.00–1.64 (4H, m, CH$_2$×2); MS (CI$^+$) m/z 404 (M+1$^+$, 90%); Found: C, 54.52; H, 4.60; N, 3.11. Calcd. for C$_{20}$H$_{19}$F$_6$NO.HCl: C, 54.62; H, 4.58; N, 3.18%.

DESCRIPTION 4

(+)-(2S,3S)-3-((3,5-Bis(trifluoromethyl)phenyl)methyloxy)-1-(carbomethoxy)methyl-2-phenylpiperidine The title compound was prepared from (+)-cis-3-((3,5-bis(trifluoromethyl)phenyl)methyloxy)-2-phenylpiperidine (Description 3) using the procedure detailed in Description 2: mp 60°–70° C. [a]$_D$=+132.3° (c=1, MeOH). $^1$H NMR (360 MHz, CDCl$_3$) d 1.57–1.63 (3H, m, CH$_2$+CHH), 2.04–2.17 (2H, m, CHH, CHHN), 3.07–3.10 (1H, m, NCHCHO), 3.20 (1H, d, J=17.0 Hz, NCHHCO$_2$CH$_3$), 3.31 (1H, d, J=17.0 Hz, NCHH CO$_2$CH$_3$), 3.58 (3H, s, CH$_3$), 3.93 (1H, s, NCHPh), 4.07 (1H, d, J= 12.0 Hz, OCHH), 4.49 (1H, d, J=12.0 Hz, OCHH), 7.28–7.34 (3H, m, ArH), 7.43–7.45 (2H, m, ArH), 7.54 (2H, s, ArH), 7.71 (1H, s, ArH). MS (CI$^+$) m/z 476 (M+1$^+$, 100%). Found: C 58.31; H, 4.90; N, 2.94. Calcd. for C$_{23}$H$_{23}$F$_6$NO$_3$: 58.11; H, 4.88; N, 2.95%.

DESCRIPTION 5

(2R*,3R*)-3-((3,5-Bis(trifluoromethyl)phenyl)methyloxy)-1-(cyanomethyl)-2-phenylpiperidinium Hydrochloride The compound of Description 1 (5 g), potassium carbonate (1.7 g) and bromoacetonitrile (0.87 ml) were suspended in dimethylformamide (15 ml) and the mixture was stirred under nitrogen at 60° C. for 3 h. The mixture was cooled, diluted with water (200 ml) and extracted with ethyl acetate (2×50 ml). The organic extracts were washed with brine, dried (MgSO$_4$) and evaporated, affording a brown oil. This was purified on silica using ethyl acetate in petrol (10%) as eluant. This afforded the product as a colourless oil. The hydrochloride salt was prepared by dissolution in ethereal hydrogen chloride and the salt was recrystallised from ether-hexane: mp 133°–134° C. $^1$H NMR (360 MHz, CDCl$_3$) d 1.75 (2H, mc, CHH), 1.90 (2H, mc, CHH), 2.31 (1H, mc, CHH), 2.71 (1H, mc, CHH), 3.19 (1H, mc, CHHN), 3.72 (1H, mc, CHHN), 3.81 (1H, d, J=17.5 Hz, NCHHCN), 3.86 (1H, s, CHO), 4.02 (1H, d, J=17.5 Hz, NCHHCN), 4.09 (1H, s, CHPh), 4.35 (1H, d, J=13.0 Hz, OCHH), 4.73 (1H, d, J=13.0 Hz, OCHH), 7.4 (3H, mc, ArH), 7.69–7.73 (5H, m, ArH); MS (CI$^+$) m/z 443 (M$^+$+1, 30%). Found: C, 54.87; H, 4.30; N, 5.66. Calcd. for C$_{22}$H$_{18}$F$_6$N$_2$O.HCl: C, 55.18; H, 4.42; N, 5.85%.

DESCRIPTION 6

(2R*,3R*)-3-((3,5-Bis(trifluoromethyl)phenyl) methyloxy)-2-phenyl-1-(thiocarboxamidomethyl)piperidine The compound of Description 5 (1 g) was dissolved in dimethylformamide (anhydrous, 10 ml) and the solution was saturated with dry hydrogen chloride gas. The reaction was heated to 100° C. under nitrogen and thioacetamide (0.34 g) was added; this mixture was allowed to stir at 100° C. for 3 h. Dimethylformamide was removed in vacuo. The residue was extracted with ethyl acetate and the organic layer was washed with aqueous sodium bicarbonate, brine, dried ($MgSO_4$) and concentrated in vacuo to afford a brown oil. This was purified on silica using a gradient elution of ethyl acetate in petrol (10–50%). The product was further purified by recrystallisation from ethyl acetate-petrol: mp 164°–166° C.; $^1$H NMR (360 MHz, $CDCl_3$) d 1.56–1.70 (2H, m, $CH_2$), 1.96–2.10 (1H, m, CHH), 2.15–2.32 (2H, m, CHHN+CHH), 2.98–3.06 (1H, bd, NCHH), 3.09 (1H, d, J=18.0 Hz, CHH-SNH$_2$), 3.50 (1H, d, J=18.0 Hz, NCHHCSNH$_2$), 3.50 (1H, s, CHO), 3.60 (1H, s, NCHPh), 4.04 (1H, d, J=12.0 Hz, OCHHAr), 4.47 (1H, d, J=12.0 Hz, OCHHAr), 7.26–7.36 (5H, m, CHPh), 7.53 (2H, s, Ar-H), 7.75 (1H, s, Ar-H), 7.61 (1H, bs, NHH), 8.99 (1H, bs, NHH); MS (CI$^+$) m/z 477 (M$^+$+1, 15%); Found: C, 55.09; H, 4.58; N, 5.97. Calc for $C_{22}H_{22}F_6N_2OS$: C, 55.46; H, 4.65; N, 5.88.

DESCRIPTION 7

(2R*,3R*)-3-((3,5-Bis(trifluoromethyl)phenyl)methyloxy)-1-(carboxyhydrazidomethyl)-2-phenylpiperidinium Hydrochloride Hydrazine hydrate (3.0 ml) was added to a solution of the compound of Description 2 (2.95 g) in ethanol (80 ml). The solution was heated at reflux for 18 h afar which the ethanol was removed in vacuo. The residue was extracted into ethyl acetate and the organic layer was washed with brine, dried ($MgSO_4$) and concentrated to give the title compound (2.79 g). This was dissolved in methanol (5 ml) and a methanolic solution of hydrogen chloride was added. Methanol was removed in vacuo and the salt was recrystallised from diethyl ether to give the hydrochloride salt. $^1$H NMR (360 MHz, DMSO) d 1.77–1.93 (2H, m, $CH_2$), 2.08–2.21 (1H, m, $CH_2$), 2.22–2.35 (1H, m, $CH_2$), 3.56 (1H, d, NCHHCH$_2$), 3.64 (1H, d, J=16.5 Hz, NCHHCO), 3.77 (1H, d, NCHHCH$_2$), 3.92 (1H, d, J=16.5 Hz, NCHHCO), 3.96 (1H, brs, CHO), 4.37 (1H, d, J=13.0 Hz, OCHH), 4.83 (1H, d, J=13.0 Hz, OCHH), 4.95 (1H, s, CHPh), 7.36–7.46 (3H, m, ArH), 7.53–7.62 (2H, brs, ArH), 7.95 (2H, s, ArH), 7.97 (1H, s, ArH); MS(CI)$^+$m/z 475.

DESCRIPTION 8

(2S,3S)-3-((3,5-Bis(trifluoromethyl)phenyl)methyloxy)-1-(carboxyhydrazidomethyl)-2-phenylpiperidinium Hydrochloride The title compound was prepared according to the procedure outlined in Description 7 using the compound of Description 4 as a starting material. $^1$H NMR (360 MHz, DMSO) d 1.77–1.93 (2H, m, $CH_2$), 2.08–2.21 (1H, m, $CH_2$), 2.22–2.35 (1H, m, $CH_2$), 3.56 (1H, d, NCHHCH$_2$), 3.64 (1H, d, J=16.5 Hz, NCHHCO), 3.77 (1H, d, NCHHCH$_2$), 3.92 (1H, d, J=16.5 Hz, NCHHCO), 3.96 (1H, brs, CHO), 4.37 (1H, d, J=13.0 Hz, OCHH), 4.83 (1H, d, J=13.0 Hz, OCHH), 4.95 (1H, s, CHPh), 7.36–7.46 (3H, m, ArH), 7.53–7.62 (2H, brs, ArH), 7.95 (2H, s, ArH), 7.97 (1H, s, ArH); MS (CI)$^+$m/z 475.

DESCRIPTION 9

(2S,3S)-3-((3,5-Bis(trifluoromethyl)phenyl)methyloxy)-1-(cyanomethyl)-2-phenylpiperidine The title compound was prepared from the reaction of bromoacetonitrile and the compound of Description 3 according to the procedure detailed in Description 5. Purification by chromatography on silica using 10% hexane in ethyl acetate afforded the product as a colourless oil. $^1$H NMR (360 MHz, $CDCl_3$) d 1.75 (2H, mc, $CH_2CH_2N$), 2.14 (2H, mc, $CH_2CH_2N$), 2.63–2.74 (1H, m, CHHN), 2.96–3.06 (1H, m, CHHN), 3.35 (1H, d, J=17.0 Hz, CHHCN), 3.48 (1H, d, J=2.0 Hz, CHO), 3.55 (1H, d, J=17.0 Hz, CHHN), 3.64 (1H, d, J=2.0 Hz, CHPh), 4.07 (1H, d, J=12.0 Hz, OCHH), 4.52 (1H, d, J=12.0 Hz, OCHH), 7.28–7.38 (3H, m, ArH), 7.4–7.48 (2H, m, ArH), 7.56 (2H, m ArH), 7.73 (1H, m, ArH).

DESCRIPTION 10

(2S,3S)-3-((3-t-Butyl-5-methylphenyl) methyloxy)-2-phenylpiperidine

This compound was prepared from the compound of Description 3c and 3-t-butyl-5-methylbenzyl bromide, following the procedure described in Descriptions 1c–e. mp 180°–182° C. MS (CI$^+$) m/z 338 (M$^+$+1, 100%). Found: C, 73.81; H, 8.63; N, 3.74. Calcd. for $C_{23}H_{31}NO\cdot HCl$: C, 73.87; H, 8.62; N, 3.75%.

DESCRIPTION 11

(2S,3S)-3-((3,5-Dichlorophenyl)methyloxy)-2-phenylpiperidine

This compound was prepared from the compound of Description 3c and 3,5-dichlorobenzyl chloride, following the procedure described in Descriptions 1c–e. $^1$H NMR ($CDCl_3$) δ 1.49–1.53 (1H, m, CHH), 1.60–1.70 (1H, m, CHH), 1.82–1.95 (1H, m, CHH), 2.14–2.18 (1H, m, CHH), 2.79–2.87 (1H, m, NCHH), 3.27–3.31 (1H, m, NCHH), 3.60 (1H, s, CHO), 3.82 (1H, s, CHPh), 4.02–4.05 (1H, d, J=13 Hz, OCHH), 4.31–4.35 (1H, d, J=13 Hz, OCHH), 6.80 (2H, s, ArH), 7.15 (1H, s, ArH), 7.25–7.35 (5H, m, ArH). Found: C, 58.24; H, 5.38; N, 3.91. Calcd. for $C_{18}H_{19}Cl_2NO\cdot HCl$: C, 58.01; H, 5.41; N, 3.76%.

DESCRIPTION 12

(2S,3S)-3-((3-Chloro-5-methylphenyl)methyloxy)-2-phenylpiperidine

This compound was prepared from the compound of Description 3c and 3-chloro-5-methylbenzyl bromide, following the procedure described in Descriptions 1c–e: mp 235°–237° C. MS (CI$^+$) m/z 316 (M$^+$+H, 100%). Found: C, 64.68; H, 6.50; N, 3.98. Calcd. for $C_{19}H_{22}ClNO\cdot HCl$: C, 64.78; H, 6.58; N, 3.98%.

DESCRIPTION 13

(2S,3S)-3-((3,5-Bis(trifluoromethyl)phenyl)methyloxy)-2-(diphenylmethyl)pyrrolidinium Hydrochloride (a) N-t-Butyloxycarbonyl-(S)-diphenylalanal A solution of methyl sulfoxide (4.4 ml) in dichloromethane (13 ml) was added dropwise to a cooled (−78° C.) solution of oxalyl chloride (4 ml) in dichloromethane (50 ml). After 15 min, a solution of N-t-butyloxycarbonyl-(S)-diphenylalanol (10 g) in dichloromethane (150 ml) was added dropwise at −30° C. The solution was allowed to stir for 30 min, triethylamine (17 ml) was added and the solution was allowed to warm to −10° C. Ice-water (200 ml) was added to the solution which was then poured onto hexane (600 ml). The organic phase was separated, washed successively with citric add (200 ml), saturated aqueous sodium bicarbonate (2×150 ml), brine (1×150 ml) then dried (MgSO$_4$) and concentrated in vacuo to leave a white crystalline solid. $^1$H NMR (250 MHz, CDCl$_3$) δ 1.42 (9H, s, C(CH$_3$)$_3$), 4.48 (1H, d), 4.86 (1H, d), 5.10 (1H, t), 7.26 (10H, m, ArH), 9.6 (1H, s, CHO).

(b) N-t-Butyloxycarbonyl-1-(diphenylmethyl)-2-hydroxypent-4-enyl-1-amine

A solution of N-t-butyloxycarbonyl-(S)-diphenylalanal (10.9 g) in tetrahydrofuran (60 ml) was added dropwise to a soluton of allyl magnesium chloride (2M in tetrahydrofuran, 36 ml) at −10° C. After 30 min the mixture was poured onto ice-cold saturated aqueous ammonium chloride and the resulting mixture was extracted with ethyl acetate (3×150 ml). The combined organic extracts were washed with brine (1×100 ml), then dried (MgSO$_4$) and concentrated in vacuo. The residue was purified by chromatography on silica gel using hexane in ethyl acetate (gradient elution of 9:1 to 4:1) as eluant to afford the compound as a white solid. $^1$H NMR (360 MHz, CDCl$_3$) δ 1.42 (9H, s, (CH$_3$)$_3$), 2.22 (2H, m), 2.68 (3H, brs), 3.48 (t), 3.57 (1H, m), 3.86 (1H, s), 4.07 (d, J=11 Hz), 5.04 (1H, m), 5.71 (1H, m), 6.97–7.36 (10H, m, ArH).

(c) 2-((3,5-Bis(trifluoromethyl)phenyl)methyloxy)-N-t-butyloxycarbonyl-1-(diphenylmethyl)-pent-4-enyl-1-amine Sodium hydride (80% in oil, 0.53 g) was added to a solution of 3,5-bis(trifluoromethyl)benzyl bromide (5 ml) and the compound of (13b) above (5 g)in dimethylformamide (8 ml). After stirring for 1 h water (80 ml) was added and the mixture was extracted with ethyl acetate (3×100 ml). The combined organics extracts were washed with brine (1×100 ml) then dried (MgSO$_4$) and concentrated to leave an oil which was purified on silica using hexane in ethyl acetate as eluant (gradient elution of 97:3 to 4:1). This afforded the title compound as a colourless oil. $^1$H NMR (360 MHz, CDCl$_3$) δ 1.25 (s), 1.30 (s), 2.35 (m), 3.31 (m), 3.40 (dd, J=5.2, 8.3 Hz), 3.97 (d), 4.27 (d), 4.38 (d), 4.65 (m), 4.85 (d), 5.16–5.02 (m), 5.77 (m), 7.35–7.13 (m), 7.76 (s), 7.85 (s).

(d) (2S,3S)-3-((3,5-Bis(trifluoromethyl)phenyl)methyloxy-2-(diphenylmethyl)pyrrolidinium Hydrochloride A solution of the compound of (c) above (5.2 g) in dichloromethane (40 ml) and methanol (40 ml) was treated with a stream of ozone in oxygen at −78° C. for 1 h. Methyl sulfide (3 ml) was added and the mixture was warmed to 23° C. and concentrated in vacuo. The residue was dissolved in chloroform (50 ml), triethylsilane (5.6 ml) was added followed by dropwise addition of a solution of trifluoroacetic add (6.9 ml) in chloroform (5 ml). After 1 h the solvent was evaporated in vacuo and trifluoroacetic acid (10 ml) was added to the residue. After stirring for 30 min the mixture was concentrated in vacuo and the residue was partitioned between dichloromethane and saturated aqueous sodium bicarbonate. The organic layer was dried (K$_2$CO$_3$) and concentrated to leave a brown oil. This was purified on silica gel eluting with dichloromethane/methanol (99:1) to provide the title compound as the free base. This was converted to the salt by treatment with methanolic hydrogen chloride: mp >230° C. [a]$^{23}_D$=+46.6° (c=1, CH$_3$OH). Found: C, 59.95; H, 4.74; N, 2.63%. Calcd. for C$_{26}$H$_{23}$F$_6$NO.HCl.0.2H$_2$O: C, 60.11; H, 4.73; N, 2.70%.

DESCRIPTION 14

(2R,3S)-3-((3,5-Bis(trifluoromethyl)phenyl)methyloxy)-2-(diphenylmethyl)pyrrolidinium Hydrochloride The title compound was prepared from N-t-butyloxycarbonyl-(R)-diphenylalanol by a procedure analagous to that described in Description 13: mp>230° C. [a]$^{23}_D$=+12.1° (C=1, CH$_3$OH).

DESCRIPTION 15

(2S,3S)-3-((3,5-Dichlorophenyl)methyloxy)-2-(diphenylmethyl)pyrrolidinium Hydrochloride (a) N-t-Butyloxycarbonyl-2-((3,5-dichlorophenyl)methyloxy-1-(diphenylmethyl)pent-4-enyl-1-amine The compound of Description 13b was alkylated with 3,5-dichlorobenzyl chloride by a procedure analagous to that described in Description 13c, to afford the title compound as an oil. $^1$H NMR (360 MHz, CDCl$_3$) δ 1.25 (9H, s), 2.41–2.27 (2H, m), 3.32 (1H, m), 4.07 (1H, d, J=11 Hz), 4.13 (1H, d, J=12 Hz), 4.30 (1H, d, J=12 Hz), 4.65 (2H, m), 5.13 (2H, m), 5.76 (1H, m), 7.35–6.60 (13H, m). MS (CI$^+$) m/z 526, 528 (M$^+$+1, 100%, 80%).

(b) (2S,3S)-3-((3,5-Dichlorophenyl)methyloxy)-2-(diphenylmethyl)pyrrolidinium Hydrochloride The compound of Description 15a above was treated with ozone followed by triethylsilane-trifluoroacetic add by a procedure analagous to that described in Description 13d to afford the title compound as a white crystalline solid: mp>230° C. Found: C, 64.52; H, 5.34; N, 3.12. Calcd. for C$_{24}$H$_{23}$Cl$_2$NO.HCl: C, 64.23; H, 5.39; N, 3.12%.

DESCRIPTION 16

(2S,3S)-3-((3-t-Butyl-5-chlorophenyl)methyloxy)-2-phenylpiperidinium Hydrochloride (a) 4-t-Butyl-2-chloro-6-(methylthiomethyl)aniline 4-t-Butyl-2-chloroaniline (30 g) was dissolved in dichloromethane (1.21) and the solution was cooled to −5° C. N-chlorosuccinimide (21.7 g) was added portionwise to the vigorously stirred solution and stirring was continued for 1 h. Dimethyl sulfide (35 ml) was added to the solution (−5° C.) and stirring was continued for a further 1 h. The solution was then cooled to −65° C. and triethylamine (27 ml) was added. This solution was allowed to warm to room temperature overnight. The solution was evaporated to half volume, washed with sodium hydroxide (1N), water and brine successively. The organic solution was dried and evaporated and the residue was purified on silica using hexane to 3% ether in hexane as eluant. This afforded the product (31.2 g)

as a red oil. $^1$H NMR (CDCl$_3$, 250 MHz) δ 1.27 (9H, s, (CH$_3$)$_3$), 1.99 (3H, s, SCH$_3$), 3.69 (2H, s, CH$_2$SCH$_3$), 4.38 (2H, br s, NH$_2$), 6.92 (1H, d, J=2.0 Hz, ArH), 7.21 (1H, d, J=2.0 Hz, ArH). MS (CI$^+$) m/z 244 (M$^+$+1, 100%).

(b) 4-t-Butyl-2-chloro-6-methylaniline 4-t-Butyl-2-chloro-6-(methylthiomethyl)aniline (1.3 g) was dissolved in methanol (50 ml) and Raney nickel (prewashed to pH 7) was added portionwise until t.l.c. indicated all starting material had reacted (ether-hexane, 1:10). The Raney nickel was removed by filtration through celite and the flitrate was evaporated. The residue was dissolved in ether and washed with brine, dried (MgSO$_4$) and evaporated. The residue was purified on silica using hexane—5% ether in hexane as eluant to afford the product as a yellow liquid. $^1$H NMR (360 MHz, CDCl$_3$) δ 1.26 (9H, s; (CH$_3$)$_3$), 2.19 (3H, s, CH$_3$), 3.97 (2H, s, NH$_2$), 6.97 (1H, d, J=2.0 Hz, ArH), 7.14 (1H, d, J=2.0 Hz, ArH).

(c) 3-t-Butyl-5-chlorotoluene 4-t-Butyl-2-chloro-6-methylaniline (1.97 g) was dissolved in ethanol (50 ml); sulphuric acid (1.88 ml, conc.) was added dropwise and the resulting blue solution was heated at reflux. Sodium nitrite (1.72 g) was added portionwise over 30 min. The resulting mixture was heated at reflux for a further 30 min, then cooled and was poured onto ice-water and extracted with ether (2×50 ml). The ethereal extract was dried (MgSO$_4$) and evaporated and the residue was purified on silica gel using hexane as eluant. This afforded the product as a colourless oil. $^1$H NMR (360 MHz, CDCl$_3$) δ 1.29 (9H, s, (CH$_3$)$_3$), 2.31 (3H, s, CH$_3$), 6.98 (1H, brs, ArH), 7.05 (1H, brs, ArH), 7.15 (1H, brs, ArH). MS (CI$^-$) m/z 181 (M$^+$–H, 100%).

(d) 3-t-Butyl-5-chlorobenzyl bromide 3-t-Butyl-5-chlorotoluene (5.7 g) was dissolved in carbon tetrachloride (80 ml) and N-bromosuccinimide (5.56 g) was added followed by benzoyl peroxide (750 mg). This mixture was heated at reflux for 6 h. The mixture was cooled, filtered through celite and the flitrate was concentrated in vacuo. The residue was purified by chromatography on silica using hexane as eluant. This afforded the title compound as a colourless liquid. $^1$H NMR (360 MHz, CDCl$_3$) δ 1.31 (9H, s, (CH$_3$)$_3$), 4.42 (2H, s, CH$_2$), 7.20 (1H, t, J=1.5 Hz, ArH), 7.26 (1H, t, J=1.5 Hz, ArH), 7.28 (1H, t, J=1.5 Hz, ArH).

(e) (2S,3S)-1-t-Butyloxycarbonyl-3-((3-t-butyl-5-chlorophenyl)methyloxy)-2-phenylpiperidine (+)-cis-3-Hydroxy-2-phenylpiperidine (Description 3c) was reacted with 3-t-butyl-5-chlorobenzyl bromide (Description 15d above) according to the procedure detailed in Description 1c–d to afford the title compound. $^1$H NMR (360 MHz, CDCl$_3$) δ 1.27 (9H, s, C(CH$_3$)$_3$), 1.46 (9H, s, C(CH$_3$)$_3$), 1.52–1.66 (2H, m), 1.8–2.0 (2H, m), 2.69 (1H, td, J=3.5 Hz, 13.0 Hz, NCHH), 3.81 (1H, q, J=5 Hz, NCHH), 3.92 (1H, brd, CHO), 4.60 (2H, q, J=12 Hz, OCH$_2$), 5.70 (1H, brs, CHPh), 7.10 (1H, s, ArH), 7.18 (1H, s, ArH), 7.22 (2H, s, ArH), 7.43–7.47 (2H, m, ArH), 7.57–7.59 (2H, m, ArH).

(f) The compound of Description 15e above was dissolved in methanolic hydrogen chloride overnight. The solution was then concentrated in vacuo and the residue triturated with ether. This afforded the title compound as a white crystalline powder: mp 210°–211° C. $^1$H NMR (360 MHz, DMSO-d$_6$) δ 1.21 (9H, s, C(CH$_3$)$_3$), 1.66–1.80 (2H, m, CH$_2$), 1.86–1.93 (1H, m, CHH), 2.18–2.22 (1H, m, CHH), 3.04–3.11 (1H, m, NCHH), 3.3 (1H, m, NCHH), 3.88 (1H, brs, CHO), 4.14 (1H, d, J=12 Hz, OCHH), 4.52 (1H, s, CHPh), 4.53 (1H, d, J=12 Hz, OCHH), 6.95 (1H, s, ArH), 7.00 (1H, s, ArH), 7.24 (1H, t, J=1.8 Hz, ArH), 7.3–7.5 (5H, m, ArH), MS (CI$^+$) m/z 358 (M$^+$+1, 100%). Found: C, 66.68; H, 7.29; N, 3.40. Calcd. for C$_{22}$H$_{28}$ClNO.HCl: C, 67.00; H, 7.41; N, 3.55%.

DESCRIPTION 17

(2R*,3R*)-3-((3-Carbomethoxyphenyl)methyloxy)-2-phenylpiperidine (a) (2R*,3R*)-1-t-Butyloxycarbonyl-3-((3-cyanophenyl)methyloxy)-2-phenylpiperidine This compound was prepared from 1-t-butyloxycarbonyl-3-hydroxy-2-phenylpiperidine (Description 1c) and α-bromo-m-tolunitrile according to the procedure described in Example 1d. $^1$H NMR (360 MHz, CDCl$_3$) δ 1.49 (9H, s, (CH$_3$)$_3$), 1.6–1.72 (2H, m), 1.87–1.99 (2H, m), 2.72 (1H, dt, J=13, 4 Hz, NCHH), 3.80–3.95 (2H, m, CHO+NCHH), 4.65 (2H, q, J=12 Hz, OCH$_2$), 5.69 (1H, brs, CHPh), 7.1–7.5 (9H, m, ArH).

(b) (2R*,3R*)-3-((3-Carbomethoxyphenyl)methyloxy-2-phenylpiperidine

The compound of (a) above (1.5 g) was dissolved in methanol (15 ml) and concentrated hydrochloric acid (aqueous, 10 ml) was added. The contents were heated at reflux for 12 h. The solution was cooled and evaporated to leave a brown oil. This was dissolved in methanolic hydrogen chloride and the resulting solution was stirred overnight, then evaporated. The residue was purified by dispersion between water and ethyl acetate and the organic layer was dried (MgSO$_4$) and concentrated. The residue was purified by chromatography on silica using a gradient elution of 2%–6% methanol in dichloromethane. The first compound to elute was characterised as the hydrochloride salt by dissolution in methanolic hydrogen chloride. The salt was recrystallised from ethyl acetate methanol: mp 206°–208° C.

(c) (2R*,3R*)-3-((3-(Carbomethoxy)phenyl)methyloxy)-2-phenylpiperidine $^1$H NMR (CDCl$_3$) δ 1.45–1.71 (2H, m, NCH$_2$CH$_2$CH$_2$), 1.83–2.02 (1H, m, NCH$_2$CHH), 2.12–2.23 (1H, m, NCH$_2$CHH), 2.44 (1H, bs, NH), 2.77–2.90 (1H, m, NCHH), 3.24–3.34 (1H, m, NCHH), 3.61–3.66 (1H, bs, CHO), 3.8–3.83 (1H, d, J=15 Hz, CHPh), 3.90 (3H, s, COOCH$_3$), 4.15 (1H, d, J=12 Hz, OCHH), 4.39 (1H, d, J=12 Hz, OCHH), 7.09 (7H, m, ArH), 7.71 (1H, bs, ArH), 7.83–7.89 (1H, m, ArH); MS (CI$^+$) m/z 326 (M$^+$+1, 100%). Found: C, 66.31; H, 6.36; N, 3.80. Calcd. for C$_{20}$H$_{23}$NO$_3$HCl: C, 66.38; H, 6.69; N, 3.87%.

DESCRIPTION 18

(2R*,3R*)-3-((3-Carboxamidophenyl)methyloxy)-2-phenylpiperidine

The second compound to elute from the column described in 17b above was isolated as a colourless oil. $^1$H NMR (360 MHz, CDCl$_3$) δ 1.2–2.2 (4H, m), 2.82 (1H, mc), 3.27 (1H, mc), 3.66 (1H, s), 3.82 (1H, s), 4.16 (1H, d, J=12 Hz, OCHH), 4.48 (1H, d, J=12 Hz, OCHH), 5.53 (1H, brs, CONHH), 6.18 (1H, brs, CONHH), 7.0–7.4 (9H, m, ArH).

DESCRIPTION 19

(2R*,3R*)-3-((2-Methoxy-3-nitrophenyl)methyloxy)-2-phenylpiperidinium Hydrochloride This compound was prepared from the compound of Description 1c and 2-methoxy-5-nitrobenzyl bromide, following the procedure described in Descriptions 1c–e. mp 246°–248° C. MS (CI⁺) m/z 343 (M⁺+1, 45%). Found: C, 60.52; H, 5.96; N, 7.45. Calcd. for $C_{19}H_{22}N_2O_4 \cdot HCl$: C, 60.24; H, 6.12; N, 7.39%.

DESCRIPTION 20

(2R*,3R*)-3-((5-Amino-2-methoxyphenyl)methyloxy)-2-phenylpiperidinium Hydrochloride The compound of Description 19 (0.342 g) was dissolved in methanol (20 ml) with hydrochloric acid (1 ml, 2N). Palladium on charcoal (50 mg) was added and the mixture placed under an atmosphere of hydrogen for 1 h at room temperature. The solvent was removed in vacuo and the residue basified with sodium hydroxide (2M). This solution was extracted with ethyl acetate and the organic extracts were dried ($MgSO_4$) and concentrated to leave a brown oil; this was purified by column chromatography on silica using 8% methanol in dichloromethane as eluent. The resulting oil was characterised as the salt prepared by treatment with methanolic hydrogen chloride: mp 241°–243° C.

The following piperidines were prepared according to the procedures outlined in Descriptions 1 and 3, using the appropriate benzyl halide.

DESCRIPTION 21

(2S,3S)-2-Phenyl-3-((3-(trifluoromethyl)phenyl)methyloxy)piperidine

¹H NMR ($CDCl_3$) δ 1.4–2.2 (4H, m), 2.45 (1H, brs), 2.83 (1H, td, J=13 Hz and 4 Hz), 3.3 (1H, m), 3.64 (1H, d, J=2 Hz), 3.82 (1H, d, J=2 Hz), 4.13 (1H, d, J=12 Hz, OCH$\underline{H}$), 4.42 (2H, J=12 Hz, OCH$\underline{H}$), 7.75 (m, 9H, ArH).

DESCRIPTION 22

(2S,3S)-3-((3,4-Dichlorophenyl)methyloxy)-2-phenylpiperidinium Hydrochloride

¹H NMR (DMSO-$d_6$), 1.65–1.8 (2H, m), 1.8 (1H, m), 2.16 (1H, d, J=12 Hz), 3.05 (1H, m), 3.25 (1H, m), 3.83 (1H, s), 4.12 (1H, d, J=12 Hz), 4.5 (2H, m), 7.05 (1H, dd, J=7 & 2 Hz), 7.28 (1H, d, J=2 Hz), 7.35–7.5 (6H, m), 9.05 (1H, br s), 9.8 (1H, br s).

DESCRIPTION 23

(2S,3S)-3-((2,3-Dimethylphenyl)methyloxy)-2-phenylpiperidinium Hydrochloride

Ethyl acetate (10 ml) was saturated with hydrogen chloride by passing HCl gas for 5 min and a solution of 0.254 g of (2S,3S)-1-t-butoxycarbonyl-3-((2,3-dimethylphenyl)methoxy)-2-phenylpiperidine (prepared according to Description 3d) in 7 ml of ethyl acetate was added. After stirring for 2 h, the reaction mixture was concentrated in vacuo. The residual white solid was washed with ether, filtered and dried to obtain 0.23 g of (2S,3S)-3-((2,3-dimethylphenyl)methyloxy)-2-phenylpiperidinium hydrochloride. ¹H NMR (DMSO-$d_6$) δ 1.6–1.9 (3H, m), 1.75 (3H, s), 2.15 (3H, s), 2.2 (1H, m), 3.05 (1H, m), 3.25 (1H, m), 3.84 (1H, s), 4.05 (1H, d, J=14 Hz), 4.45 (1H, d, J=14 Hz), 4.48 (1H, s), 6.95–7.5 (8H, m), 8.8 (1H, br s), 9.4 (1H, br s).

DESCRIPTION 24

(2S,3S)-3-((3-t-Butylphenyl)methyloxy)-2-phenylpiperidinium Hydrochloride

¹H NMR (360 MHz, $CDCl_3$) δ 1.21 (9H, s, $C(CH_3)_3$), 1.45 (3H, s), 1.52–1.67 (2H, m, $CH_2$), 2.04–2.12 (1H, m, CH$\underline{H}$), 2.30–2.34 (1H, m, C$\underline{H}$H), 2.93–2.96 (1H, m, NCH$\underline{H}$), 3.54 (1H, d, J=13 Hz, NC$\underline{H}$H), 3.72 (1H, s, NC$\underline{H}$CHO), 4.14 (1H, d, J=2 Hz, NCH$\underline{C}$HO), 4.28–4.36 (2H, q, J=13 Hz, OCH$\underline{H}$), 6.87–6.89 (1H, m, ArH), 7.05 (1H, s, ArH), 7.11–7.15 (1H, m, ArH), 7.20–7.34 (4H, m, ArH), 7.55–7.58 (2H, m, ArH). MS (CI+) m/z 323 (M⁺+1, 100%).

DESCRIPTION 25

(2R*,3R*)-3-((3,5-Dimethylphenyl)methyloxy)-2-phenylpiperidinium Hydrochloride

¹H NMR (360 MHz, $CDCl_3$) δ 1.48 (m), 1.62 (m), 1.86 (m), 2.20 (s), 2.82 (ddd, J=3.0. 3.0, 12.6 Hz), 3.26 (dt, J:2.15, 2.15, 12.5 Hz), 3.63 (s), 3.78 (s), 4.10 (d, J=12.0 Hz), 4.33 (d, J=12.0Hz), 6.31 (s), 7.2–7.4 (m). MS (CI⁺) m/z 296 (M⁺+1).

DESCRIPTION 26

(2R*,3R,)-3-((3,5-Bis(trifluoromethyl)phenyl)methyloxy)-2-(3-chlorophenyl)piperidine (a) Methyl-4-nitrobutyrate and 3-chlorobenzaldehyde were reacted in an analogous manner to that described in Description 1a to give 2-(3-chlorophenyl)-3-nitro-6-oxopiperidine: mp 131°–133° C. ¹H NMR (360 MHz, $CDCl_3$) δ 2.26–2.36 (1H, m), 2.50–2.72 (3H, m), 4.66–4.71 (1H, m), 5.24–5.28 (1H, d), 6.57 (1H, s), 7.17–7.40 (4H, m).

(b) The product of part a) was treated analogously to that described in Description 1b to give 2-(3-chlorophenyl)-3,6-dioxopiperidine: mp 144°–147° C. ¹H NMR (360 MHz, $CDCl_3$) δ 2.8 (4H, m), 5.0 (1H, d), 6.4 (1H, s), 7.22–7.42 (4H, m).

c) The product of part b) was treated analogously to that described in Description 1c and 3a to give cis-2-(3-chlorophenyl)-3-hydroxypiperidine tosylate salt: mp' 250° C. ¹H NMR (360 MHz, $CDCl_3$) δ 1.60–2.07 (4H, m), 2.28 (3H, s), 3.00–3.11 (1H, m), 4.02 (1H, s), 4.62–4.66 (1H, d), 5.96 (1H, s), 7.10–7.20 (2H, d), 7.41–7.59 (6H, m).

d) The product of part c) was treated analogously to that described in Description 1c to give cis-1-t-butyloxycarbonyl-2-(3-chlorophenyl)-3-hydroxypiperidine as a clear, viscous oil. ¹H NMR (360 MHz, $CDCl_3$) δ 1.40 (9H, s), 1.61–1.90 (4H, m), 2.88–3.01 (1H, ddd), 3.93–3.99 (1H, dd), 4.03–4.10 (1H, m), 5.33 (1H, d), 7.20–7.26 (2H, m), 7.34–7.38 (1H, m), 7.47–7.52 (1H, m) m/z (CI⁻) 310, 312; m/z (CI⁺) 312, 314.

e) The product of part d) and 3,5-bis(trifluoromethyl)benzylbromide were treated in an analogous manner to that described in Description 1d to give cis-3-((3,5-bis(trifluoromethyl)phenyl)methyloxy)- 1-t-butyloxy-carbonyl-2-(3-chlorophenyl)piperidine. ¹H NMR (250 MHz, $CDCl_3$) δ 1.24–1.30 (1H, m), 1.47 (9H, s), 1.60–2.00 (3H, m), 2.67–2.80 (1H, ddd), 3.81–4.01 (2H, m), 4.8 (2H, s), 5.61–5.67 (1H, d), 7.23–7.27 (2H, m), 7.39–7.44 (1H, m), 7.6 (1H, s), 7.78 (2H, s), 7.8 (1H, s).

f) The product of part e) was treated in an analogous manner to that described in Description 1e to give cis-3-((3,5-bis(trifluoromethyl)phenyl)methyloxy)-2-(3-chlorophenyl)piperidine hydrochloride salt, mp=158° C. $^1$H NMR (360 MHz, DMSO-d$_6$) δ 1.70–1.96 (4H, m), 2.19–2.28 (1H, m), 3.02–3.13 (1H, m), 3.84 (1H, s), 4.35–4.39 (2H, d), 4.60 (1H, s), 4.79–4.85 (2H, d), 7.39–7.44 (3H, m), 7.58 (1H, s), 7.84 (2H, s), 7.97 (1H, s), 9.2 (br s), 10.05 (br s). Found: C, 50.44; H, 4.13; N, 3.01. C$_{20}$H$_{18}$ClF$_6$NO.HCl requires C, 50.65; H, 4.04; N, 2.95%. m/z (CI$^+$), 438,440.

DESCRIPTION 27

2S,3S)-3-((3-Fluoro-5-methylphenyl)methyloxy)-2-phenylpiperidine mp 219°–221° C. $^1$H NMR (360 MHz, CDCl$_3$) δ 1.50–1.68 (2H, m), 2.11–2.15 (1H, m), 2.20 (3H, s, CH$_3$), 2.31–2.35 (1H, m), 2.94–2.98 (1H, m, NCHH), 3.55–3.58 (1H, d, J=12 Hz, NCHH), 3.69 (1H, bs, CHO), 4.15–4.18 (1H, m, CHPh), 4.18 (1H, d, J=13 Hz, OCHH), 4.33 (1H, d, J=13 Hz, OCHH), 6.47 (1H, d, ArH), 6.59 (1H, s, ArH), 6.66 (1H, d, ArH), 7.26–7.37 (3H, m, ArH), 7.52–7.54 (2H, m, ArH). MS (CI$^+$) m/z 300 (M$^+$+1, 100%).

DESCRIPTION 28

(3R*)-3-((3,5-Bis(trifluoromethyl)phenyl)methyloxy)-2-methyl-2-(2R*)-2-phenylpiperidine (a) 3,6-Dioxo-2-phenylpiperidine (Description 1b) (5 g) was dissolved in dimethylformamide (25 ml) at 0° C. Sodium hydride (873 mg, 80% dispersion in oil) was added portionwise and the mixture stirred for 15 min. Methyl iodide was added (1.8 ml) and the mixture was stirred for 12 h. The mixture was diluted with water (250 ml) and extracted with ethyl acetate (3 x). The combined organic extracts were washed with brine, dried (MgSO$_4$) and concentrated to leave a solid: 3,6-dioxo-2-methyl-2-phenylpiperidine.

(b) The ketene of (a) above (3.2 g) was suspended in methanol under nitrogen and the temperature brought to –40° C. Sodium borohydride (0.3 g) was added portionwise. The mixture was stirred for 30 min and then concentrated in vacuo, azeotroping with tetrahydrofuran. Borane tetrahydrofuran complex (64 ml, 1.0M in tetrahydrofuran) was added and the mixture was heated at reflux overnight. The mixture was cooled and quenched carefully with methanol, and the mixture was then concentrated in vacuo. The resulting residue was dissolved in ethanol (100 ml) and potassium carbonate (4.2 g) was added. The mixture was heated at reflux for 12 h. The mixture was cooled and evaporated and the residue was extracted with ethyl acetate and water. The organic extract was washed with brine, dried (MgSO$_4$) and evaporated to afford 3-hydroxy-2-methyl-2-phenylpiperidine as a white solid. $^1$H NMR (360 MHz, CDCl$_3$) δ 7.79 (2H, d, ArH), 7.40 (2H, t, ArH), 7.15–7.19 (1H, m, ArH), 3.89 (1H, mc), 2.89–3.01 (2H, m), 1.67–1.91 (4H, m), 1.39 (3H, s, CH$_3$).

(c) The alcohol of (b) above (3 g) was dissolved in dichloromethane (50 ml) and di-t-butyldicarbonate (3.48 g) was added. The solution was allowed to stir for 12 h. The solution was concentrated in vacuo and the residue was purified by chromatography on silica using ethyl acetate in petrol (20:80) as eluent. This afforded N-t-butyloxycarbonyl-2-hydroxy-2-methyl-2-phenylpiperidine as a clear oil. $^1$H NMR (250 MHz, CDCl$_3$) δ 1.08 (9H,s, (CH$_3$)$_3$), 1.80 (3H, s, CH$_3$), 1.6–2.0 (4H, m), 3.6–3.74 (2H, m), 3.8–3.92 (1H, m, CHO), 7.2–7.36 (5H, m, ArH).

(d) The alcohol of (c) above (2.2 g) was dissolved in dry dimethylformamide (12 ml). Sodium hydride was added (0.36 g, 60% dispersion in oil) portionwise and the mixture was allowed to stir at room temperature for 30 min. 3,5-Bis(trifluoromethyl)benzyl bromide (3.5 g) was added dropwise and the mixture was allowed to stir for 5 h. The mixture was diluted with aqueous ammonium chloride, extracted with ethyl acetate and the organic extract was washed with brine, dried (MgSO$_4$) and evaporated in vacuo. The residue as purified by column chromatography on silica using a gradient elution, 100% petrol to 10% ethyl acetate in petrol as eluant, to afford the product 3-((3,5-bis(trifluoromethyl)phenyl)methyloxy-1-t-butyloxycarbonyl-2-methyl-2-phenylpiperidine as a colourless oil. $^1$H NMR (360 MHz, CDCl$_3$) δ 1.13 (9H, s (CH$_3$)$_3$), 1.85 (3H, s, CH$_3$), 1.85–1.99 (4H, m, CH$_2$CH$_2$), 3.48 (1H, brs, NCHH), 3.68–3.75 (1H, m, NCHH), 3.80–3.85 (1H, m, CHO), 3.85 (1H, d, J=12 Hz, OCHH), 4.36 (1H, d, J=12 Hz, OCHH), 7.17–7.32 (5H, m, ArH), 7.42 (2H, s, ArH), 7.71 (1H, s, ArH).

(e) The compound of (d) above (2.1 g) was dissolved in trifluoroacetic acid (30 ml) for 10 min and was then evaporated in vacuo. The residue was dissolved in dichloromethane, washed with sodium hydroxide (2M), water and brine, then dried (MgSO$_4$) and concentrated in vacuo. Methanolic hydrogen chloride was added to the residue and when dissolved the solvent was evaporated. The residue was triturated with ether to afford the product as a white powder: (3R*)-3-((3,5Bis(trifluoromethyl)phenyl)methyloxy)-2-methyl-(2R*)-2-phenyl-piperidine. $^1$H NMR (360 MHz, DMSO) δ 1.67 (3H, s, CH$_3$), 1.70 (1H, m), 1.84–1.91 (1H, m), 1.99–2.06 (2H, m), 3.16 (1H, m), 3.33 (1H, m), 4.19 (1H, s), 4.29 (1H, d, J=12 Hz, OCHH), 4.75 (1H, d, J=12 Hz, OCHH), 7.29–7.33 (1H, m, ArH), 7.37–7.41 (3H, m, ArH), 7.54 (2H, s, ArH), 7.56 (1H, brs, ArH), 7.89 (1H, s, ArH). Found: C, 55.38; H, 4.92; N, 3.08 Calcd. for C$_{21}$H$_{21}$F$_6$NO: C, 55.58; H, 4.89; N, 3.09%.

DESCRIPTION 29

(2S,3S)-3-((3,4-Dimethylphenyl)methyloxy)-2-phenylpiperidine $^1$H NMR (CDCl$_3$) δ 1.4–1.9 (3H, m), 2.11 (3H, s), 2.17 (3H, s), 2.1–2.3 (1H, m), 2.78 (1H, m), 3.25 (1H, m), 3.60 (1H, s), 3.76 (1H, s), 4.08 (1H, d, J=12 Hz), 4.27 (1H, d, J=12 Hz), 6.7 (2H, m), 6.92 (1H, d, J=9 Hz), 7.2–7.5 (5H, m).

DESCRIPTION 30

(2S,3S)-3-((3-(isoPropoxy)phenyl)methyloxy)-2-phenylpiperidine $^1$H NMR (250 MHz, CDCl$_3$) δ 1.6–1.9 (3H, m), 1.97 (1H, d, J=7 Hz), 2.16 (1H, m), 3.05 (1H, m), 3.3 (1H, m), 3.84 (1H, s), 4.09 (1H, d, J=12 Hz), 4.41 (1H, d, J=12 Hz), 4.44 (1H, m), 4.5 (1H, s), 6.6 (2H, m), 6.72 (1H, m), 7.09 (1H, t, J=8 Hz), 7.3–7.5 (5H, m).

DESCRIPTION 31

(2S,3S)-3-((3,5-Bis(trifluoromethyl)phenyl)methyloxy)-2-(3-fluorophenyl)piperidine $^1$H NMR (360 MHz, CDCl$_3$) δ 1.66–1.9 (3H, m), 2.2–2.3 (1H, m), 2.43–2.5 (1H, m), 3.0–3.2 (1H, m), 3.98 (1H, s), 4.37 (1H, d, J=12 Hz), 4.62 (1H, s), 4.79 (1H, d, J=12 Hz), 7.04–7.46 (4H, m, ArH), 7.80 (2H, s, ArH), 7.96.(1H, s, ArH).

EXAMPLE 1

3-Amino-5-[{(2R*,3R*)-3-((3,5-Bis(trifluoromethyl)phenyl)methyloxy)-2-phenylpiperidino}methyl]-1,2,4-oxadiazole Hydroxyguanidine sulphate hydrate (2.3 g) was dissolved in water and freeze-dried overnight. Ethanol (35 ml) and powdered molecular sieves (1 g) were added to the solid hydroxyguanidine and the suspension was stirred under nitrogen for 1 hour. Sodium (670 mg) was added to the mixture which was stirred until all sodium had reacted. The suspension assumed an orange colour at this time and was placed in an ultrasound bath for 15 min. The ester of Description 2 (1.4 g) was added to the mixture which was then heated at reflux for 2 h. The reaction mixture was cooled and filtered through celite. Ethanol was removed in vacuo and the residue was extracted into ethyl acetate and washed with water and brine. The organic layer was dried ($MgSO_4$) and evaporated. The residue was purified on silica using 25% ethyl acetate in petrol as eluant. This afforded the product (800 mg) as a solid which was recrystallised from ether/hexane to afford colourless prisms: mp 160°–161° C. $^1$H NMR (360 MHz, DMSO-$d_6$) d 1.47–1.54 (2H, m, $CH_2$), 1.85–1.9 (1H, m, CHH), 2.14–2.17 (1H, m, CHH), 2.35–2.40 (1H, m, CHHN), 2.99–3.02 (1H, m, CHHN), 3.35 (1H, d, J=15.0 Hz, N-CHH-oxadiazole), 3.60 (2H, brs, NCHCHO), 3.65 (1H, d, J=15.0 Hz, N-CHH-oxadiazole), 4.06 (1H, d, J=13.0 Hz, OCHH), 4.62 (1H, d, J=13.0 Hz, OCHH), 6.2 (2H, brs, $NH_2$), 7.23–7.31 (3H, m, ArH), 7.42–7.44 (2H, m, ArH), 7.69 (2H, s, ArH), 7.93 (1H, s, ArH); MS (CI$^+$) m/z 501 ((M+1)$^+$, 75%). Found: C, 54.81; H, 4.47; N, 11.2. Calcd. for $C_{23}H_{22}F_6N_4O_2$: C, 55.20; H, 4.43; N, 11.2%.

EXAMPLE 2

5-[{(2R*,3R*)-3-((3,5-Bis(trifluoromethyl)phenyl)methyloxy)-2-phenylpiperidino}methyl]-3-methyl-1,2,4-oxadiazole Acetamideoxime (117 mg) and powdered molecular sieves were suspended in dry tetrahydrofuran (10 ml) and stirred under nitrogen for 1 hour. Sodium hydride (63 mg of 60% suspension in oil) was added and the mixture heated to 50° C. until all hydrogen evolution had ceased. The ester of Description 2 (500 mg) was dissolved in tetrahydrofuran (2 ml) and added to the above mixture. This mixture was heated at reflux for 2 h, cooled, filtered through celite and evaporated in vacuo. The residue was dissolved in ethyl acetate and washed with water and then brine. The organic layer was dried ($MgSO_4$) and evaporated in vacuo. The residue was purified by medium pressure chromatography (Lobar) using 25% ethyl acetate in petrol as eluant. This afforded the product as a crystalline solid: mp 85°–86° C.; $^1$H NMR (360 MHz, DMSO-$d_6$) d 1.47–1.54 (2H, m, $CH_2$), 1.85–1.89 (1H, m, CHH), 2.13–2.17 (1H, m, CHH), 2.31 (3H, s, $CH_3$), 2.34–2.40 (1H, m, CHHN), 2.98–3.01 (1H, m, CHHN), 3.51 (1H, d, J=15.0 Hz, NCHH-oxadiazole), 3.60 (2H, s, NCHCHO), 3.81 (1H, d, J=15.0 Hz, NCHH-oxadiazole), 4.06 (1H, d, J=13.0 Hz, OCHH), 4.62 (1H, d, J=13.0 Hz, OCHH), 7.25–7.31 (3H, m, ArH), 7.43–7.45 (2H, m, ArH), 7.70 (2H, s, ArH), 7.93 (1H, s, ArH); MS (EI) m/z 500 ((M+I)$^+$, 100%). Found: C, 57.94; H, 4.79; N, 8.23. Calcd. for $C_{24}H_{23}F_6N_3O_2$: C, 57.72; H, 4.64; N, 8.41%.

EXAMPLE 3

(+)3-Amino-5-[{(2S,3S)-3-((3,5-bis(trifluoromethyl) phenyl)methyloxy)-2-phenylpiperidino}methyl]-1,2,4-oxadiazole The title compound was prepared from the ester of Description 4 using the procedure described in Example 1: mp 138°–139° C.; [a]$^{23}_D$=+147.7° (c=1, MeOH). $^1$H NMR (360 MHz, CDCl$_3$) d 1.47–1.50 (2H, m, $CH_2$), 1.85–1.89 (1H, m, CHH), 2.14–2.17 (1H, m, CHH), 2.35–2.41 (1H, m, CHHN), 2.99–3.02 (1H, m, CHHN), 3.29 (1H, s, NCHCHO), 3.33 (1H, d, J=15.0 Hz, NCHH-het), 3.65 (1H, d, J=15.0 Hz, NCHH-het), 3.60 (1H, brs, NCHPh), 4.05 (1H, d, J=13.0 Hz, OCHH), 4.62 (1H, d, J=13.0 Hz, OCHH), 6.20 (2H, s, $NH_2$), 7.23–7.31 (3H, m, ArH), 7.42–7.44 (2H, m, ArH), 7.69 (2H, s, ArH), 7.93 (1H, s, ArH); MS (CI$^+$) m/z 501 (M+1$^+$, 75%). Found: C, 54.81; H, 4.47; N, 11.2. Calcd. for $C_{23}H_{22}F_6N_4O_2$: C, 54.98; H, 4.54; N, 11.30%.

EXAMPLE 4

3[{(2R*,3R*)-3-((3,5-Bis(trifluoromethyl)phenyl)methyloxy)-2-phenylpiperidino}methyl]pyridinium Hydrochloride The compound of Description 1 (410 mg), 3-picolyl chloride (167 mg) and potassium carbonate were suspended in dimethylformamide (3 ml) and the mixture heated at 60° C. for 12 h. The mixture was cooled, diluted with water (50 ml) and extracted with ethyl acetate (2×10 ml). The organic phase was washed with brine, dried ($MgSO_4$) and evaporated. The residue was purified on silica using a gradient elution of 25–50% ethyl acetate in petrol. The product was dissolved in ethereal hydrogen chloride to form the dihydrochloride salt which was recrystallised from benzene: mp 198°–200° C. $^1$H NMR (360 MHz, DMSO-$d_6$, 353K) d 1.68–1.82 (2H, m, $CH_2$), 2.09–2.18 (2H, m, $CH_2$), 3.06 (1H, mc, CHHN), 3.37 (1H, mc, CHHN), 3.89 (1H, s, NCHCHO), 4.16 (1H, brd, NCHH-pyridine), 4.20 (1H, brd, NCHH-pyridine), 4.26 (1H, d, J=13.0 Hz, CHHO), 4.56 (1H, brs, NCHPh), 4.72 (1H, d, J=13.0 Hz, CHHO), 7.37–7.41 (3H, m, ArH), 7.60–7.64 (1H, m, ArH), 7.71–7.72 (2H, m, ArH), 7.86 (1H, s, ArH), 7.89 (2H, s, ArH), 8.08 (1H, d, J=8.0 Hz, ArH), 8.64 (1H, s, ArH), 8.68 (1H, d, J=5.0 Hz, ArH); MS (CI$^+$) m/z 495 (M$^+$+1, 60%); Found: C, 52.45; H, 4.90; N, 4.52. Calcd. for $C_{26}H_{24}F_6N_2O$·2HCl·1.5$H_2O$: C, 52.54; H, 4.92; N, 4.71%.

EXAMPLE 5

2-[{(2R*,3R*)-3-((3,5-Bis(trifluoromethyl)phenyl)methyloxy)-2-phenylpiperidino}methyl] pyridinium Hydrochloride The compound of Description 1 was reacted with 2-picolyl chloride following the procedure illustrated in Example 4: mp 175°–180° C. $^1$H NMR (360 MHz, DMSO-$d_6$) d 1.65–1.83 (2H, m, $CH_2$), 2.08–2.15 (2H, m, $CH_2$), 3.16–3.20 (1H, m, CHHN), 3.30–3.40 (1H, m, CHHN), 3.70 (1H, s, NCHCHO), 4.18 (1H, d, J=14.0 Hz, CHH-pyridine), 4.23 (1H, d, J=14.0 Hz, CHH-pyridine), 4.30 (1H, d, J=13.0 Hz, OCHH), 4.79 (1H, d, J=13.0 Hz, OCHH), 4.78 (1H, s, CHPh), 7.24 (1H, d, J=7.5 Hz, ArH), 7.36–7.4 (3H, m, ArH), 7.47–7.51 (1H, m, ArH), 7.62 (2H, mc, ArH), 7.85 (1H, dt, J=7.5, 2.0 Hz, ArH), 7.94 (2H, s, ArH), 7.97 (1H, s, ArH), 8.65 (1H, d, J=7.5 Hz, ArH); MS (CI$^+$) m/z 495 (M+1)$^+$, 100%). Found: C, 53.01; H, 4.79; N, 4.69. Calcd. for $C_{26}H_{24}F_6N_2O$·2HCl·$H_2O$: C, 53.30; H, 4.82; N, 4.78%.

EXAMPLE 6

2-[{(2R*,3R*)-3-((3,5-Bis(trifluoromethyl)phenyl)methyloxy)- 2-phenylpiperidino}methyl] benzimidazole The compound of Description 1 was reacted with 2-(chloromethyl)benzimidazole following the procedure illustrated in Example 4: mp 152°–153° C. $^1$H NMR (360 MHz, DMSO-d$_6$) d 1.44–1.59 (2H, m, NCH$_2$CH$_2$CH$_2$), 1.85–1.89 (1H, m, CHHCH$_2$N), 2.15–2.18 (2H, m, NCHH+ CHHCH$_2$N), 2.86–2.89 (1H, m, NCHH), 3.15–3.19 (1H, d, J=14.0 Hz, NCHH-imidazole), 3.57 (1H, s, NCHCHO), 3.63 (1H, s, NCHCHO), 3.80–3.84 (1H, d, J=14.0 Hz, NCHH-imidazole), 4.10–4.13 (1H, d, J=13.0 Hz, —OCHH), 4.63–4.66 (1H, d, J=13.0 Hz, —OCHH), 7.07–7.15 (2H, m, ArH), 7.24–7.34 (3H, m, ArH), 7.43–7.52 (2H, m, ArH), 7.60–7.62 (2H, m, ArH), 7.67 (2H, s, ArH), 7.94 (1H, s, ArH), 12.10 (1H, s, NH); MS (CI$^+$) m/z 534 ((M+1)$^+$, 100%).

EXAMPLE 7

5-[{(2R*,3R*)-3-((3,5-Bis(trifluoromethyl)phenyl)methyloxy)- 2-phenylpiperidino}methyl] tetrazole The compound of Description 5 (1.0 g), triethylamine hydrochloride (467 mg) and sodium azide (441 mg) were dissolved in 1-methyl-2-pyrrolidinone (5 ml) and the reaction mixture was heated at reflux under nitrogen for 2 h. The mixture was then cooled, and diluted with ice/water (80 ml) and acidified to pH=2 with methanolic hydrogen chloride. This precipitated the product as a white solid, which was purified on silica using a gradient elution of methanol in dichloromethane (0–5%). The product was recrystallised from ether-hexane: mp 114°–115° C. $^1$H NMR (360 MHz, DMSO-d$_6$) d 1.59–1.65 (2H, m, NCH$_2$CH$_2$CH$_2$), 2.02–2.22 (2H, m, NCH$_2$CH$_2$), 2.39–2.46 (1H, m, CHHN), 2.98–3.02 (1H, m, CHHN), 3.62 (1H, s, NCHCHO), 3.66 (1H, s, NCHCHO), 3.70–3.74 (1H, d, J=15.5 Hz, NCHH-tetrazole), 4.05–4.10 (1H, d, J=15.5 Hz, NCHH-tetrazole), 4.08–4.12 (1H, d, J=12.0 Hz, OCHH), 4.51–4.54 (1H, d, J=12.0 Hz, OCHH), 5.30 (1H, s, NH), 7.30–7.35 (3H, m, ArH), 7.45–7.47 (2H, m, ArH), 7.51 (2H, s, ArH), 7.74 (1H, s, ArH); MS (CI$^+$) m/z 486 (M$^+$+1, 85%). Found: C, 53.14; H, 4.58; N, 13.96. Calcd. for C$_{22}$H$_{21}$F$_6$N$_5$O.0.5H$_2$O: C, 53.44; H, 4.48; N, 14.16%.

EXAMPLE 8

2-[{(2R*,3R*)-3-((3,5-Bis(trifluoromethyl)phenyl)methyloxy)- 2-phenylpiperidino}methyl]-4-methyl-1,3-thiazole Anhydrous acetone (2 ml) and methanol (2 ml) and tetrabutylammonium perbromide (111 mg) were stirred under nitrogen to generate a solution of bromoacetone in situ. The compound of Description 6 (150 mg) was added to this mixture and the resulting solution was stirred for 2 h. A second equivalent of bromoacetone was added and the mixture was stirred for a further 2 h. The volatile solvents were removed in vacuo and the residue was dispersed between aqueous potassium carbonate and ethyl acetate. The organic phase was washed with brine, dried (MgSO$_4$) and concentrated in vacuo affording a brown oil. This was purified on silica using a gradient elution of ethyl acetate in petrol (10–30%) which gave the product as a clear oil: $^1$H NMR (360 MHz, CDCl$_3$) 1.51–1.68 (2H, m, CH$_2$), 1.98–2.22 (2H, m, CH$_2$), 2.26–2.37 (1H, m, NCHH), 2.38 (3H, s, CH$_3$), 3.18–3.26 (1H, m, NCHH), 3.47 (1H, d, J=15.0 Hz, NCHH), 3.54 (H, bs, CHO), 3.58 (H, bs, CHPh), 3.94 (1H, d, J=15.0 Hz, NCHH), 4.01 (1H, d, J=12.5 Hz, OCHH), 4.47 (1H, d, J=12.5 Hz, OCHH), 6.80 (1H, s, SCH), 7.24–7.35 (3H, .m, Ar-H), 7.52–7.54 (2H, m, Ar-H), 7.58 (2H, s, Ar-H), 7.72 (1H, s, Ar-H); MS (CI$^+$) m/z 515 (M$^+$+1, 100%). Found: C, 58.59; H, 4.88; N, 5.48 Calc for C$_{25}$H$_{24}$F$_6$N$_2$OS: C, 58.36; H, 4.70; N, 5.44%.

EXAMPLE 9

(2R*,3R*)-3-((3,5-Bis(trifluoromethyl)phenyl)methyloxy)-1-(2-furoyl)-2-phenylpiperidine The compound of Description 1 (400 mg) and triethylamine (300 mg) were dissolved in dichloromethane and the mixture was stirred for 10 min at 0° C. 2-Furoyl chloride (155 mg) was added to the solution and the reaction mixture was stirred for 15 min. The mixture was then washed with brine; the organic layer was separated, dried (MgSO$_4$) and concentrated in vacuo. The residue-was purified by chromatography on silica using 20% ethyl acetate in petrol, affording a dear oil. $^1$H NMR (360 MHz, DMSO-d$_6$) d 1.6–1.8 (2H, m, CH$_2$), 1.9–2.1 (2H, m, CH$_2$), 2.99 (1H, mc, CHHN), 4.02 (1H, q, J=5.0 Hz, CHO), 4.0–4.2 (1H, m, CHHN), 4.78 (1H, d, J=13.0 Hz, OCHH), 4.86 (1H, d, J=13.0 Hz, OCHH), 5.95 (1H, s, CHPh), 6.62 (1H, s, furan-H), 6.99 (1H, s, furan-H), 7.25–7.36 (3H, m, ArH), 7.51–7.54 (2H, m, ArH), 7.83 (1H, s, furan-H), 7.90 (2H, s, ArH), 7.99 (1H, s, ArH); MS (CI$^+$) m/z 498 (M$^+$+1, 20%).

EXAMPLE 10

2-[{(2R*,3R*)-3-((3,5-Bis(trifluoromethyl)phenyl)methyloxy)- 2-phenylpiperidino}methyl] furan The compound of Example 9 (340 mg) was dissolved in tetrahydrofuran. To this solution was added borane-dimethyl sulfide complex (0.18 ml of 10M solution) and the resulting solution was heated at reflux for 8 h. The mixture was cooled, methanol added to quench excess borane, and the solvents were removed in vacuo. The residue was dissolved in methanol (10 ml) and potassium carbonate was added (238 mg). This mixture was heated at reflux for 1 hour; the methanol was removed in vacuo and the residue was dispersed between ethyl acetate and brine. The ethyl acetate layer was dried (MgSO$_4$) and evaporated. The residue was purified by chromatography on silica using 10% ethyl acetate in petrol. The product was recrystallised from ether-hexane: mp 103°–104° C. $^1$H NMR d 1.4–1.5 (2H, m, CH$_2$CH$_2$), 1.8–1.9 (1H, m, CHHCH$_2$N), 2.1–2.2 (2H, m, CHHCH$_2$N and CHHN), 2.95–3.0 (1H, m, CHHN), 3.11–3.15 (1H, d, J=15.0 Hz, NCHH-furan), 3.38 (1H, s, NCHCHO), 3.54–3.58 (1H, d, J=15.0 Hz, NCHH-furan), 3.56 (1H, s, NCHCHO), 4.02–4.06 (1H, d, J=13.0 Hz, OCHH—), 4.59–4.62 (1H, d, J=13.0 Hz, OCHH—), 6.08–6.09 (1H, m, furan H), 6.35–6.36 (1H, m, furan-H), 7.24–7.32 (3H, m, ArH), 7.46–7.48 (2H, m, ArH), 7.55 (1H, s, furan-H), 7.68 (2H, s, ArH), 7.93 (1H, s, ArH); MS (CI$^+$) m/z 485 (M$^+$+1, 100%). Found: C, 62.11; H, 4.80; N, 2.90. Calcd. for C$_{25}$H$_{23}$NF$_6$O: C, 62.27; H, 4.83; N, 2.96.

EXAMPLE 11

5-[{(2R*,3R*)-3-((3,5-Bis(trifluoromethyl)phenyl) methyloxy)-2-phenylpiperidino}methyl]-3-bromo-1, 2,4-oxadiazole hydrochloride Diisopropylethylamine (220 μl ) was added to a stirred suspension of the compound of Description 1 (200 mg) and 5-bromo-3-(chloromethyl)-1,2,4-oxadiazole (99 mg) (J. Heterocyclic Chem. 1989, 26, 23) in dry acetonitrile. The resulting solution was allowed to stir at room temperature for 48 hrs. After this time the solvent was removed under reduced pressure and the residual oil purified by column chromatography on silica using ethyl acetate in hexane (20%) as eluant to afford a waxy solid. Treatment of an ethereal solution of this solid with ethereal hydrogen chloride yielded a white precipitate. Recrystallisation from ether afforded the title compound as an amorphous white solid: mp 100°–102° C. $^1$H NMR (360 MHz, DMSO-$d_6$) d 1.67–1.70 (2H, m, $CH_2$), 1.83 (1H, m, CHH), 2.30 (1H, m, CHH), 2.74 (1H, m, CHHN), 3.10 (1H, m, CHHN), 3.70 (1H, d, J=11.0 Hz, CH—$OCH_2$), 3.82 (1H, brs, N—CH—Ph), 4.34 (1H, d, J=16.0 Hz, NCHH-oxadiazole), 4.36 (1H, d, J=11.0 Hz, OCHH—Ar), 4.58 (1H, d, J=16.0 Hz, NCHH-oxadiazole), 4.73 (1H, d, J=11.0 Hz, OCHH—Ar), 7.34–7.42 (5H, m, ArH), 7.68 (2H, s, ArH), 7.73 (1H, s, ArH); MS (CI$^+$) m/z 564 ((M+1)$^+$, 20%). Found: C, 45.64; H, 3.63; N, 6.70. Calcd. for $C_{23}H_{20}N_3O_2F_6Br·HCl$: C, 45.98; H, 3.52; N, 6.99%.

EXAMPLE 12

5-[{(2R*,3R*)-3-((3,5-Bis(trifluoromethyl)phenyl) methyloxy)-2-phenylpiperidino}methyl]-3-dimethylamino-1,2,4-oxadiazole hydrochloride The compound of Example 11 (169 mg) in dimethylamine (33% in ethanol) was heated to 40° C. for 30 min. The solvent was removed under reduced pressure and the residue purified by column chromatography on silica using ethyl acetate in hexane (20%) as eluant. The compound was dissolved in ether and treated with excess ethereal hydrogen chloride to afford a white precipitate. Recrystallisation from ether afforded the product as white powder (110 mg): mp 179°–180° C. $^1$H NMR (360 MHz, DMSO-$d_6$) d 1.59 (2H, m, $CH_2$), 2.1–2.21 (2H, m, $CH_2$), 2.4–2.45 (1H, m, CHHN), 3.01 (6H, s, N($CH_3$)$_2$), 3.10 (1H, m, CHHN), 3.60 (1H, brs, CH—O—$CH_2$), 3.70 (1H, d, J=16.0 Hz, NCHH-oxadiazole), 3.78 (1H, d, J=1.0 Hz, N—CH—Ph), 3.82 (1H, d, J=16.0 Hz, NCHH-oxadiazole), 4.01 (1H, d, J=15.0 Hz, O—CHH—Ar), 4.49 (1H, d, J=15.0 Hz, O—CHH—Ar), 7.3 (3H, m, ArH), 7.4 (2H, m, ArH), 7.49 (2H, s, ArH), 7.64 (1H, s, ArH); MS (CI$^+$) m/z (M$^+$+1) 529. Found: C, 51.87; H, 4.93; N, 9.62. Calcd. for $C_{25}H_{26}N_4O_2F_6·HCl·H_2O$. C, 51.51; H, 5.01; N, 9.61%.

EXAMPLE 13

(2R*,3R*)-3-((3,5-Bis(trifluoromethyl)phenyl)methyloxy)- 2-phenyl-1-(2-thienoyl)piperidine The compound of Description 1 was reacted with 2-thiophenecarbonyl chloride as outlined in Example 9. The oil obtained after work-up and removal of solvent was purified by chromatography on silica, eluting with 10% ethyl acetate in petroleum ether to afford the pure product as a clear oil. $^1$H NMR (250 MHz, CDCl$_3$) d 1.6–1.8 (2H, m, $CH_2$), 2.1–2.2 (2H, m, $CH_2$), 3.0 (1H, m, CHN), 4.0 (1H, dt, J=5 Hz, 2 Hz, CH), 4.1 (1H, brs, CHN), 4.7 (1H, d, J=7 Hz, CHAr), 4.8 (1H, d, J=7 Hz, CHAr), 6.2 (1H, brs, NCHPh), 7.02 (1H, dd, J=1, 2 Hz, thiophene-H), 7.3–7.44 (4H, m, Ar—H), 7.5 (1H, dd, J=1, 3 Hz, thiophene-H), 7.6–7.92 (5H, m, Ar—H).

EXAMPLE 14

(2R*,3R*)-3-((3,5-Bis(trifluoromethyl)phenyl)methyloxy)- 2-phenyl-1-(2-thienylmethyl)piperidine The compound of Example 13 was reacted with borane dimethylsulfide as described in Example 10. The free base was recrystallised from ether and hexane to give the product as a white crystalline solid. $^1$H NMR (250 MHz, CDCl$_3$) d 1.44–1.64 (2H, m, $CH_2$), 1.9–2.2 (2H, m, $CH_2$), 2.24 (1H, d, J=7 Hz, CHN), 3.14 (1H, d, J=7 Hz, CHN), 3.4 (1H, s, CHO), 3.56 (1H, s, NCHPh), 3.6 (1H, s, CH-thiophene), 4.88 (1H, d, J=10 Hz, CH-thiophene), 4.0 (1H, d, J=10 Hz, CHAr), 4.24 (1H, d, J= 10 Hz, CHAr), 6.7 (1H, d, J=1 Hz, thiophene-H), 6.9 (H, dd, J= 2 Hz, 3 Hz, thiophene-H), 7.2 (1H, d, J=3 Hz, thiophene-H), 7.28 (4H, m, Ar—H), 7.5 (3H, m, Ar—H), 7.68 (1H, s, Ar—H). MS m/z 500 (M$^+$, 100% ).

EXAMPLE 15

5-[{(2R*,3R*)-3-((3,5-Bis(trifluoromethyl)phenyl) methyloxy)-2-phenylpiperidino}methyl]-2,3-dihydro-4-methyl-3 -thioxo-1,2,4-triazole hydrochloride A suspension of the compound of Description 7 (0.50 g) and methyl isothiocyanate (0.09 ml) in 1-butanol (10 ml) was heated under reflux for 10 min. 1,8-Diazabicyclo[5.4.0] undec-7-ene (0.1 ml) was added and the reaction mixture was heated under reflux for 2.5 h. The solvent was removed in vacuo and the residue was partitioned between water and ethyl acetate. The organic layer was dried (MgSO$_4$) and evaporated. The residue was purified on silica using 5% methanol in dichloromethane as eluant to give the title compound. The product (470 mg) was characterised as the hydrochloride salt. $^1$H NMR (360 MHz, DMSO-$d_6$) d 1.77–1.93 (2H, m, $CH_2$), 2.05–2.22 (1H, m, CHH), 2.31 (1H, d, J=13.5 Hz, CHH), 3.42 (3H, s, $CH_3$), 3.45–3.51 (1H, m, NCHHCH$_2$), 3.83 (1H, d, J=12.0 Hz, NCHHCH$_2$), 3.97 (1H, brs, CHO), 4.24 (1H, d, J=15.5 Hz, N—CHH-het), 4.32 (1H, d, J=15.5 Hz, N—CHH-het), 4.33 (1H, d, J=12.5 Hz, O—CHH), 4.76 (1H, s, NCH), 4.80 (1H, d, J=12.5 Hz, O—CHH), 7.42–7.50 (3H, m, ArH), 7.59 (2H, brs, ArH), 7.85 (2H, s, ArH), 7.89 (1H, s, ArH), 9.15 (1H, brs, NH); MS (FAB) m/z 530 ((M+1)$^+$, 13%).

EXAMPLE 16

3-[{(2R*,3R*)-3-((3,5-Bis(trifluoromethyl)phenyl) methyloxy)-2-phenylpiperidino}methyl]-1,2,4-triazole The compound of Description 1 (1.0 g), anhydrous potassium carbonate (0.94 g) and N-formyl-2-chloroacetamidohydrazone (0.46 g), (prepared according to Yanagisawa, I., J. Med. Chem. 1984, 27, 849) were heated to 60° C. in anhydrous dimethylformamide for 3 h, followed by heating at 130° C. for 12 h. The reaction mixture was cooled, diluted with ethyl acetate (100 ml) and washed with water, (3×20 ml). The ethyl acetate layer was dried (MgSO$_4$), filtered and evaporated to give a brown oil. This was purified on silica using ethyl acetate in petrol (70:30) as eluant. This afforded the product as a white solid. $^1$H NMR (250 MHz, CDCl$_3$) d 1.6 (2H, m, CH$_2$), 1.95–2.24 (2H, m, CH$_2$), 2.34 (1H, m, NCHH), 3.06 (1H, m, NCHH), 3.44 (1H, d, NCHH-triazole), 3.5 (1H, bs, CHO), 3.6 (1H, bs, NCHPh), 3.8 (1H, d, N—CHH-triazole), 4.04 (1H, d, OCHH—Ar), 4.50 (1H, d, OCHHAr), 7.3 (3H, m, ArH), 7.44 (2H, m, ArH), 7.5 (2H, s, ArH), 7.7 (1H, s, ArH), 7.9 (1H, s, triazole-H). MS (CI$^+$) m/z 485 (M$^+$+1, 35%).

EXAMPLE 17

5-[{(2R*,3R*)-3-((3,5-Bis(trifluoromethyl)phenyl)methyloxy)-2-phenylpiperidino}methyl]-2,3-dihydro-(4H)-3-thioxo- 1,2,4-triazole The compound of Description 7, potassium thiocyanate (0.45 g) and conc. hydrochloric acid (2.3 ml) in water (12 ml) were heated under reflux for 2 h. After cooling, solid sodium hydroxide was added until pH=8 and the aqueous layer was extracted with ethyl acetate. The organic layer was dried (MgSO$_4$), filtered and evaporated to give the crude semi-carbazide which was heated at reflux in 2N sodium hydroxide solution (10 ml) for 2 h. After cooling the solution was acidified to pH 5–6 and the product extracted into ethyl acetate. The organic layer was dried (MgSO$_4$), filtered and evaporated. The crude triazole was chromatographed on silica eluting with 40% ethyl acetate/60–80 petroleum ether to give the title compound as a white solid. $^1$H NMR (250 MHz, CDCl$_3$) d 1.6 (2H, m, CH$_2$), 1.9–2.3 (3H, m, CH$_2$+NCHH), 2.95 (1H, bd, NCHH), 3.16 (1H, d, N—CHH-Het), 3.20 (1H, bs, CHO), 3.6 (1H, bs, NCHPh), 3.78 (1H, d, N—CHH-Het), 4.1 (1H, d, CHH—Ar), 4.58 (1H, d, CHH—Ar), 7.32 (5H, m, ArH), 7.5 (2H, s, Ar—H), 7.78 (1H, s, ArH). MS (FAB) m/z 517 (M$^+$+1, 80%).

EXAMPLE 18

5-[{(2R*,3R*)-3-((3,5-Bis(trifluoromethyl)phenyl)methyloxy)-2-phenylpiperidino}methyl]-2-methyltetrazole The compound of Example 7 (500 mg) was suspended in water (4 ml) and sodium hydroxide (44 mg) added. This was heated to an external temperature of 96° C. and dimethyl sulphate (65 mg) added. The reaction mixture was allowed to stir under nitrogen at 96° C. for 1 h after which time stirring was continued for 24 h at 5° C. After this time, the product was extracted into dichloromethane and washed with water and brine. The organic layer was dried (MgSO$_4$) and evaporated. The residue was purified on silica using medium pressure chromatography (Lobar), and eluted with 25% ethyl acetate in petrol. The first compound to be eluted was isolated, and this afforded the product (50 mg) as a crystalline solid, which was recrystallised from ether/hexane to afford white crystals: mp 139°–141° C. $^1$H NMR (360 MHz, DMSO) d 1.44–1.51 (2H, m, CH$_2$), 1.79–1.82 (1H, m, CHH), 2.12–2.15 (1H, m, CHH), 2.19–2.25 (1H, m, CHHN), 2.97–3.00 (1H, m, CHHN), 3.37 (1H, d, J=14 Hz, N—CHH-tetrazole), 3.52 (1H, s, NCHCHO), 3.58 (1H, s, NCHCHO), 3.81 (1H, d, J=14 Hz, N—CHH-tetrazole), 4.03 (1H, d, J=13 Hz, OCHH), 4.31 (3H, s, CH$_3$), 4.60 (1H, d, J=13 Hz, OCHH), 7.23–7.33 (3H, m, ArH), 7.49–7.51 (2H, m, ArH), 7.68 (2H, s, ArH), 7.93 (1H, s, ArH); MS (CI$^+$) m/z 500 ((M+1)$^+$, 100%). Found: C, 55.56; H, 4.76; N, 14.20. Calculated for C$_{23}$H$_{23}$N$_5$OF$_6$: C, 55.31; H, 4.64; N, 14.02%.

EXAMPLE 19

5-[{(2R*,3R*)-3-((3,5-Bis(trifluoromethyl)phenyl)methyloxy)-2-phenylpiperidino}methyl]-1-methyltetrazole The title compound was prepared as described in Example 18. During purification, the second compound to be eluted was isolated, and this afforded the product (120 mg) as a crystalline solid, which was recrystallised from ether/hexane to afford yellow crystals: mp 75°–77° C. $^1$H NMR (360 MHz, DMSO) d 1.51–1.55 (2H, m, CH$_2$), 1.84–1.87 (1H, m, CHH), 2.12–2.16 (1H, m, CHH), 2.31–2.37 (1H, m, CHHN), 2.81–2.84 (1H, m, CHHN), 3.52 (1H, d, J=15 Hz, NCHH-tet), 3.54 (1H, s, NCHCHO), 3.60 (1H, s, NCHCHO), 3.82 (1H, d, J=14 Hz, NCHH-tet), 3.84 (3H, s, CH$_3$), 4.14 (1H, d, J=13 Hz, OCHH), 4.85 (1H, d, J=13 Hz, OCHH), 7.26–7.32 (3H, m, ArH), 7.45–7.48 (2H, m, ArH), 7.74 (2H, s, ArH), 7.94 (1H, s, ArH); MS (CI$^+$) m/z 500 ((M+1)$^+$, 20%).

EXAMPLE 20

3-[{(2R*,3R*)-3-((3,5-Bis(trifluoromethyl)phenyl)methyloxy)-2-phenylpiperidino}methyl]-5-dimethylamino-1,2,4-thiadiazole a) 5-Dimethylamino-3-(chloromethyl)-1,2,4-thiadiazole A solution of dimethylamine in ethanol (0.5 ml×33%) was added to a stirred suspension of 5-chloro-3-(chloromethyl)-1,2,4-thiadiazole (540 mg) (J. Goerdeler, Chem. Ber. 1957, 90, p 182 or ICI EP 0006679) and potassium carbonate (1.0 g) in methanol. The solution was stirred at room temperature for three hours, and then the solvent removed under reduced pressure. The residue was taken up in ethyl acetate (40 ml), washed with water (20 ml) and brine (20 ml). The organic layers were dried (MgSO$_4$), filtered and the solvent removed to afford a yellow gum. Flash chromatography using 10% ethyl acetate in hexane as eluent, afforded the product as a yellow oil (330 mg). $^1$H NMR (360 MHz, CDCl$_3$) d 3.15 (6H, s, N(CH$_3$)$_2$), 4.51 (2H, s, Cl—CH$_2$); MS (CI$^+$) m/z 178 ((M+1)$^+$, 95%).

b) A solution of the compound of Description 1 (223 mg), 5-dimethylamino-3-(chloromethyl)-1,2,4-thiadiazole (100 mg) and diisopropylethylamine (0.2 ml) were heated at reflux in dry acetonitrile for three hours. The reaction was then allowed to cool to room temperature and the solvent removed under reduced pressure. Purification of the residue by flash chromatography (40% EtOAc/nHex) gave a yellow gum. Recrystallisation from n-hexane afforded the product as yellow plates: mp 144°–145° C. $^1$H NMR (360 MHz, CDCl$_3$) d 1.57 (2H, m, CH$_2$), 2.11 (3H, m, CH$_2$+CHH), 2.42 (1H, m, CHH), 3.11 (6H, s, N(CH$_3$)$_2$), 3.20 (1H, m, CH—OCH$_2$), 3.47 (1H, d, J=14.5 Hz, CHH-thiadiazole), 3.56 (1H, m, CHPh), 3.75 (1H, d, J=14.5 Hz, CHH-thiadiazole), 4.03 (1H, d, J=10.5 Hz, OCHH—Ar), 4.45 (1H, d, J=10.5 Hz, OCHH—Ar), 7.30 (3H, m, ArH), 7.51 (2H, s, ArH), 7.53 (2H, m, ArH), 7.69 (1H, s, ArH); MS (CI$^+$) m/z 545 ((M+1)$^+$, 60%). Found: C, 55.12; H, 4.75; N, 10.38. Calcd. for C$_{25}$H$_{20}$F$_6$N$_4$SO: C, 55.14; H, 4.81; N, 10.30%.

EXAMPLE 21

2-[{(2R*,3R*)-3-((3,5-Bis(trifluoromethyl)phenyl)methyloxy)-2-phenylpiperidino}methyl]-4,7-dimethylbenzoxazole A solution of 2-(chloromethyl)-4,7-dimethylbenzoxazole (285 mg) in dry acetonitrile (10 ml) was added to a solution of the compound of Description 1 in dry acetonitrile (10 ml)

containing diisopropylethylamine (0.4 ml). The resulting mixture was heated at reflux for three hours, cooled to room temperature and the residue purified by flash chromatography on silica gel using 20% ethyl acetate/n-hexane as eluant. Recrystallisation of the isolated material from n-hexane afforded the product as white needles: mp 109°–110° C. $^1$H NMR (CDCl$_3$) 1.49–1.53 (2H, m, CH$_2$), 1.56–1.60 (1H, m, CHH), 2.03–2.09 (1H, m, CHH), 2.10–2.16 (1H, m, CHHN), 2.36–2.40 (1H, m, CHHN), 2.47 (3H, s, Ar—CH$_3$), 2.54 (3H, s, ArCH$_3$), 3.24 (1H, m, CHN), 3.59 (1H, m, CHOCH$_2$), 3.67 (1H, d, J=12.0 Hz, N—CHH-benzoxazole), 3.79 (1H, d, J=12.0 Hz, N—CHH-benzoxazole), 3.96 (1H, d, J= 10.0 Hz, OCHH), 4.47 (1H, d, J=10.0 Hz, OCHH), 6.99 (2H, s, ArH), 7.32 (3H, m, ArH), 7.54 (2H, s, ArH), 7.57 (2H, m, ArH), 7.71 (1H, s, ArH); MS (CI$^+$) m/z 563 ((M+1)$^+$, 70%). Found: C, 64.09; H, 5.04; N, 5.12. Calcd for C$_{30}$H$_{28}$N$_2$O$_2$F$_6$: C, 64.05; H, 5.01; N, 5.00%.

EXAMPLE 22

2-[{(2R*,3R*)-3-((3,5-Bis(trifluoromethyl)phenyl)methyloxy)-2-phenylpiperidino}methyl]benzoxazole This compound was prepared following the procedure described in Example 21, using 2-(chloromethyl)benzoxazole as the alkylating agent: mp 95°–97° C. $^1$H NMR (CDCl$_3$) d 1.47–1.60 (2H, m, CH$_2$), 2.06–2.19 (2H, m, CH$_2$), 2.42–2.56 (1H, dd, 1H, J= 6.0, 4.0 Hz, NCHH), 3.26 (1H, dd, J=4.0, 2.0 Hz, NCHH), 3.61 (1H, s, CHO), 3.66 (1H, d, J=15.0 Hz, NCHH-benzoxazole), 3.66 (1H, d, J=2.0 Hz, CHPh), 4.02 (1H, d, J=15.0 Hz, CHH-benzoxazole), 4.04 (1H, d, J=12.0 Hz, OCHH), 4.48 (1H, d, J=12.0 Hz, OCHH), 7.26–7.67 (12H, m, ArH); MS (CI$^+$) m/z 535 ((M+1)$^+$ 65%). Found: C, 62.36; H, 4.67; N, 5.27. Calc for C$_{28}$H$_{24}$F$_6$N$_2$O$_2$.¼H$_2$O: C, 62.39; H, 4.58; N, 5.20%.

EXAMPLE 23

4-[{(2S,3S )-3-((3,5-Bis(trifluoromethyl)phenyl)methyloxy)- 2-phenylpiperidino}methyl]oxazole 1,3-oxazole-4-carboxaldehyde was prepared following the procedure described by J. Hodges, W. Patt and C. Connolly, *J. Org. Chem.* 1991, 56, 449–452.

a) 4-(Hydroxymethyl)-1,3-oxazole 1,3-Oxazole-4-carboxaldehyde (0.38 g) was dissolved in anhydrous methanol and stirred under nitrogen; sodium borohydride (0.074 g) was added carefully. After 1 hour no starting material was present by TLC using 50% ethyl acetate in hexane as eluent. The methanol was removed by rotary evaporator (water bath temp 40° C.). The residue was purified by chromatography on silica eluting with 100% diethyl ether. This afforded the alcohol (0.27 g) as a white solid. $^1$H NMR d (360 MHz, CDCl$_3$) 2.93 (OH), 4.63 (2H, s, CH$_2$OH), 7.64 (1H, s, oxazole-H), 7.90 (1H, s, oxazole-H).

b) 4-[{(2S,3S)-3-((3,5-Bis(trifluoromethyl)phenyl)methyloxy)-2-phenylpiperidino}methyl]oxazole 4-(Hydroxymethyl)-1,3-oxazole (0.13 g) was dissolved in anhydrous dichloromethane (4 ml) under an atmosphere of nitrogen. Triethylamine (0.19 ml) and p-toluenesulfonyl chloride (0.13 g) were added to the reaction mixture which was stirred for 1 hour at room temperature. A further portion of p-toluenesulfonyl chloride (0.13 g) and a catalytic amount of dimethylaminopyridine were added to the reaction mixture. The compound of Description 3 (1.2 g, free base) was dissolved in dimethylformamide (5 ml) and was added to the reaction mixture followed by triethylamine (0.19 ml). The mixture was heated at 60° C. for 2 h and the resulting mixture was diluted with water (50 ml) and extracted with dichloromethane (3×20 ml). The combined organic layers were dried (MgSO$_4$) and concentrated in vacuo to afford a yellow oil. This was purified by chromatography on silica gel using a gradient elution of 30–60% ether in hexane to afford the title compound as a white solid. This was recrystallised from ether/hexane: mp 102°–104° C. $^1$H NMR (360 MHz, CDCl$_3$) d 1.46–1.64 (1H, m, NCH$_2$CH$_2$CHH), 1.7–1.87 (1H, m, NCH$_2$CH$_2$CHH), 1.96–2.20 (2H, m, NCH$_2$CH$_2$), 2.32–2.48 (1H, m, NCHH), 3.20–3.46 (3H, m, NCHH+ NCHH-oxazole+CHOCH$_2$Ar), 3.55 (1H, brs, CHPh), 3.68 (1H, d, J=14.5 Hz, NCHH-oxazole), 4.01 (1H, d, J=11.5 Hz, OCHHAr), 4.46 (1H, d, J=11.5 Hz, OCHHAr), 7.24–7.58 (8H, m, ArH), 7.70 (1H, s, ArH), 7.80 (1H, s, ArH); MS (CI$^+$) 485 (M$^+$+ 1, 100%)

EXAMPLE 24

2-[{(2S,3S)-3-((3,5-Bis(trifluoromethyl)phenyl)methyloxy)-2-phenylpiperidino}methyl]pyrazine a) 2-(Chloromethyl)pyrazine 2-Methylpyrazine (1 g) was dissolved in carbon tetrachloride (50 ml) under nitrogen. N-Chlorosuccinimide (1.42 g) and benzoyl peroxide (50 mg) were added and the mixture was heated at reflux for 24 h. The reaction mixture was cooled and filtered through celite and the filtrate was concentrated in vacuo. The resulting oil was purified on silica using 30% ethyl acetate in petrol. $^1$H NMR (360 MHz, CDCl$_3$) d 4.72 (2H, s, CH$_2$Cl), 8.56 (2H, s, ArH), 8.76 (1H, s, ArH).

b) 2-[{(2S,3S)-3-((3,5-Bis(trifluoromethyl)phenyl)methyloxy)-2-phenylpiperidino}methyl]pyrazine 2-(Chloromethyl)pyrazine (0.17 g), potassium carbonate (0.6 g) and the compound of Description 3 (0.35 g) were suspended in dimethylformamide (3 ml); the reaction mixture was heated at 60° C. for 12 h. The mixture was cooled, diluted with water (30 ml) and extracted with ethyl acetate (2×20 ml). The combined organic layers were washed with brine, dried (MgSO$_4$) and concentrated in vacuo to afford a brown oil. The product was purified by column chromatography on silica gel using a gradient elution of 15–35% ethyl acetate in hexane. This afforded the product as a white solid, which was recrystallised from pentane to give colourless crystals: mp 108°–110° C. $^1$H NMR (360 MHz, DMSO-d$_6$) d 1.42–1.60 (2H, m NCH$_2$CH$_2$CH$_2$), 1.77–1.92 (1H, m, NCH$_2$CHH), 2.13–2.25 (2H, m, NCHH+ NCH$_2$CHH), 2.84–2.92 (1H, m, NCHH), 3.12 (1H, d, J=14.0 Hz, NCHH-pyrazine), 3.55 (1H, m, CHO), 3.63 (1H, m, CHPh), 3.78 (1H, d, 14.0 Hz, NCHH-pyrazine), 4.11 (1H, d, J=13.0 Hz, OCHHAr), 4.64 (1H, d, J=13.0 Hz, OCHHAr), 7.20–7.33 (3H, m, ArH), 7.49–7.56 (2H, m, ArH), 7.71 (2H, s, ArH), 7.93 (1H, s, ArH), 8.48–8.63 (3H, m, ArH); MS (CI$^+$) 496 (M$^+$+1, 60%). Found: C, 60.90; H, 4.86; N, 8.48. Calcd. for C$_{25}$H$_{23}$F$_6$N$_3$O: C, 60.60; H, 4.68; N, 8.48%.

EXAMPLE 25

4-[{(2S,3S)-3-((3,5-Bis(trifluoromethyl)phenyl)methyloxy)- 2-phenylpiperidino}methyl]-2-methyl-1,3-thiazolium dihydrochloride 4-(Chloromethyl)-2-methylthiazole hydrochloride (83 mg) was added to a suspension of the compound of Description 3 and potassium carbonate in dimethylformamide (5 ml). The resulting mixture was heated at 60° C. for 18 h, cooled to room temperature and diluted with water (50 ml). This solution was extracted with ethyl acetate (2×25 ml) and the combined organic extracts were washed with water (2×20 ml), brine (20 ml), dried ($MgSO_4$) and filtered. The resulting solution was evaporated under reduced pressure to afford a yellow oil. This was purified by medium pressure liquid chromatography using 50% ethyl acetate in hexane to afford the product as a white solid. This was treated with ethereal hydrogen chloride and recrystallised from methyl-t-butyl ether to afford the title compound: mp 58°–60° C. $^1$H NMR (360 MHz, DMSO-$d_6$) d 1.71 (2H, m, $CH_2$), 2.11 (2H, mc, $CH_2$), 2.49 (1H, m, CHHN), 2.69 (3H, s, Ar—$CH_3$), 3.15 (1H, m, CHHN), 3.54 (1H, m, CHO), 4.12 (2H, m, $CH_2$-thiazole), 4.16 (1H, d, J=10.0 Hz, OCHHAr), 4.58 (1H, brs, CHPh), 4.76 (1H, d, J=10.0 Hz, OCHHAr), 7.40–7.43 (5H, m, ArH), 7.64 (1H, brs, ArH), 7.92 (2H, s, ArH), 7.97 (1H, s, ArH); MS (CI$^+$) m/z 515 (M$^+$+1). Found: C, 48.17; H, 4.76; N, 4.52. Calcd. for $C_{25}H_{24}F_6N_2OS.2HCl.2H_2O$: C, 48.16; H, 4.85; N, 4.49%.

EXAMPLE 26

3-[{(2S,3S)-3-((3,5-Bis(trifluoromethyl)phenyl)methyloxy)- 2-phenylpiperidino}methyl]-1,2,4-oxadiazole hydrochloride 3-(Chloromethyl)-1,2,4-oxadiazole (270 mg) was added to a rapidly stirred suspension of the compound of Description 3 and potassium carbonate in dimethylformamide (10 ml). The reaction mixture heated at 60° C. for 4 h, cooled to room temperature and diluted with water (50 ml). The aqueous solution was extracted with ethyl acetate (3×50 ml) and the organic extracts were combined, washed with water (3×50 ml), brine (50 ml), dried ($MgSO_4$) and filtered. The resulting solution was concentrated under reduced pressure and purified by column chromatography on silica gel using 20% ethyl acetate in hexane as eluent. The resulting oil was treated with ethereal hydrogen chloride to afford the title compound as a white powder: mp 74°–75° C. $^1$H NMR (360 MHz, DMSO-$d_6$) d 1.62 (2H, m, $CH_2$), 1.97–2.1 (2H, m, $CH_2$), 2.50 (1H, m, CHHN), 3.16 (1H, m, CHHN), 3.51 (1H, m, CHO), 3.69–3.72 (3H, m, $CH_2$-oxadiazole+CHPh), 4.14 (1H, d, J=10.0 Hz, OCHHAr), 4.70 (1H, d, J=10.0 Hz, OCHHAr), 7.32 (3H, m, ArH), 7.45 (2H, m, ArH), 7.78 (3H, m, ArH), 7.94 (1H, s, ArH).

EXAMPLE 27

3-[{(2S,3S)-3-((3,5-Bis(trifluoromethyl)phenyl)methyloxy)- 2-phenylpiperidino} methyl]-5-iodo-1,2,4-thiadiazole a) 5-Iodo-3-(iodomethyl)-1,2,4-thiadiazole Sodium iodide (excess) was added to a stirred solution of 5-chloro-3-(chloromethyl)-1,2,4-thiadiazole (3.0 g) (J. Goerdeler, Chem. Ber. 1957, 90, 182) in dry butanone (15 ml). The resulting solution was heated at reflux for four hours, cooled to room temperature and filtered. The filtrate was diluted with water (20 ml) and extracted with ethyl acetate (50 ml). The ethyl acetate layer was dried ($MgSO_4$), filtered and concentrated in vacuo to afford a red oil, which was used in the following reaction without further purification.

b) 3-[{(2S,3S)-3-((3,5-Bis(trifluoromethyl)phenyl) methyloxy)-2- phenylpiperidino}methyl]-5-iodo-1,2,4-thiadiazole Diisopropylethylamine (116 mg) was added to a stirred solution of 5-iodo-3-(iodomethyl)-1,2,4,thiadiazole (160 mg) and the compound of Description 3 (200 mg) in dry acetonitrile (10 ml). The resulting solution was stirred at room temperature for 18 h. The reaction mixture was filtered and the solvent was removed in vacuo to afford a red oil. This was purified using column chromatography on silica gel using 20% ethyl acetate in hexane as eluent. This afforded the product as a powder: mp 98°–101° C. $^1$H NMR (360 MHz, CDCl$_3$) d 1.55 (3H, m, NCH$_2$CH$_2$CH$_2$+NCH$_2$CHH), 2.13 (2H, m, NCH$_2$CHH+NCHH), 2.42 (1H, m, CHHN), 3.21 (1H, m, CHO), 3.69 (2H, m, CHPh+CHH-thiadiazole), 4.02 (2H, m, CHH-thiadiazole+OCHH), 4.48 (1H, d, J=8.0 Hz, OCHH), 7.32 (5H, m ArH), 7.51 (2H, s ArH), 7.70 (1H, s, ArH).

EXAMPLE 28

3-[{(2S,3S )-3-((3,5-Bis(trifluoromethyl)phenyl)methyloxy)-2-phenylpiperidino}methyl]-1,2,4-thiadiazole hydrochloride Sodium borohydride (280 mg) was added to a stirred solution of the compound of Example 27 (500 mg) and palladium (II) chloride (280 mg) in dry methanol (25 ml). The resulting mixture was stirred for 30 min and then filtered through celite; the filtrate was concentrated in vacuo. The solid residue thus obtained was dissolved in ethyl acetate and the solution was washed with water (10 ml), the organic extract was dried ($MgSO_4$), filtered and concentrated in vacuo to afford a yellow oil. Treatment of this oil with ethereal hydrogen chloride afforded the title compound as a white powder: mp 89°–90° C. $^1$H NMR (360 MHz, DMSO-$d_6$) d 1.79 (2H, m, $CH_2$), 1.9–2.20 (3H, m, CHHN+NCH$_2$CH$_2$), 2.6 (1H, m, CHHN), 3.8 (1H, bm, CHO), 3.89 (1H, brs, CHPh), 4.2–4.3 (3H, m, $CH_2$-thiadiazole+OCHH), 4.76 (1H, d, J=9.0 Hz, OCHH), 7.39 (3H, m, ArH), 7.55 (2H, m, ArH), 7.89 (2H, s, ArH), 8.32 (1H, s, ArH), 10.32 (1H, s, N—CH—S); MS (CI$^+$) m/z 502 (M$^+$+1). Found, d: C, 49.31; H, 4.09; N, 7.18%. Calcd. for $C_{23}H_{21}F_6N_3OS.HCl.1.25H_2O$: C, 49.48; H, 4.37; N, 7.52%.

EXAMPLE 29

3-[{(2S,3S )-3-((3,5-Bis(trifluoromethyl)phenyl)methyloxy)- 2-phenylpiperidino}methyl]-5-methoxy-1,2,4-thiadiazole hydrochloride Sodium methoxide (34 mg) was added to a stirred solution of the compound of Example 27 (200 mg) in methanol (5 ml). The solution was heated at reflux for 2 h, cooled to room temperature and the solvent removed under reduced pressure affording a solid residue. The solid was dissolved in ethyl acetate (15 ml), and the organic phase was washed with water (20 ml), separated, dried ($MgSO_4$) and the solvent was removed under reduced pressure. The residual solid was treated with ethereal hydrogen chloride and the resulting solid was recrystallised from ethyl acetate to afford the product as white needles: mp 74°–75° C. $^1$H NMR (360 MHz, DMSO-$d_6$) d 1.55 (2H, m, $CH_2$), 1.73 (1H, m, CHH), 2.09 (2H, m $CH_2$), 2.43 (1H, m, CHH), 3.20 (1H, m, CHO), 3.49 (2H, m, CHPh+CHH-thiadiazole), 3.75 (1H, m, CHH-thiadiazole), 4.02 (1H, d, J=10.0 Hz, OCHH), 4.14 (3H, s, OCH$_3$), 4.45 (1H, d, J=10.0 Hz, OCHH), 7.30 (3H, m ArH), 7.51 (4H, brs, ArH), 7.54 (1H, s, ArH); MS (CI$^+$) m/z 532 (M$^+$+1). Found: C, 49.89; H, 4.10; N, 7.41. Calcd. for $C_{24}H_{23}F_6N_3O_2S.HCl.0.5H_2O$: C, 49.96; H, 4.37; N, 7.28%.

EXAMPLE 30

3-[{(2S,3S)-3-((3,5-Bis(trifluoromethyl)phenyl)methyloxy)- 2-phenylpiperidino}methyl]-1,2,4-triazole dihydrochloride The title compound was prepared according to the procedure described in Example 16, using the compound of Description 3 as starting material. The free base was treated with ethereal hydrogen chloride to afford the product as a white crystalline solid: mp (free base) 209°–210° C. Found: C, 49.36; H, 4.57; N, 10.05. Calcd. for $C_{23}H_{22}F_6N_4O.2HCl$: C, 49.56; H, 4.34; N, 10.05%.

EXAMPLE 31

5-[{(2S,3S )-3-((3,5-Bis(trifluoromethyl)phenyl)methyloxy)- 2-phenylpiperidino}methyl]-2,3-dihydro-(4H)-3-thioxo-1,2,4-triazole hydrochloride The title compound was prepared according to the procedure described in Example 17, using the compound of Description 8 as a starting material. This afforded the product as a white solid which was treated with ethereal hydrogen chloride to yield the crystalline hydrochloride: mp 154°–157° C. Found: C, 46.59; H, 4.52, N, 9.26; Cl, 5.84. Calcd. for $C_{23}H_{22}F_6N_4O.HCl.2H_2O$: C, 46.90; H, 4.62; N, 9.51; Cl, 6.02%.

EXAMPLE 32

2-[{(2S,3S)-3-((3,5-Bis(trifluoromethyl)phenyl)methyloxy)- 2-phenylpiperidino}methyl]-1-(p-toluenesulfonyl)imidazole dihydrochloride (a) N-(p-Toluenesulfonyl)imidazole-2-carboxaldehyde.

Imidazole-2-carboxaldehyde (1.92 g) was suspended in dichloromethane (20 ml). p-Toluenesulfonyl chloride (3.8 g) and triethylamine (2.8 ml) were added to the mixture which was stirred at room temperature for 12 hours. The resulting slurry was diluted with water and the organic layer was washed with brine, dried ($MgSO_4$) and filtered. The dichloromethane layer was concentrated in vacuo and the residue was purified by column chromatography on silica using 50% ethyl acetate in hexane as eluent. This afforded the product as a yellow oil which crystallised on standing. $^1H$ NMR (360 MHz, $CDCl_3$) d 2.44 (3H, s, $ArCH_3$), 7.31 (1H, d, J=1.5 Hz, imidazole-H), 7.37 (2H, d, J=8.0 Hz, ArH), 7.83 (1H, d, J=1.5 Hz, imidazole-H), 8.00 (2H, d, J=8.0 Hz, ArH), 9.78 (1H, s, CHO). MS ($CI^+$) m/z 251 ($M^+$+1).

(b) 2-(Hydroxymethyl)-1-(p-toluenesulfonyl)imidazole

The aldehyde of (a) above (3 g) was dissolved in methanol (15 ml) and sodium borohydride (114 mg) was added portionwise. This solution was stirred for 10 min. Methanol was removed in vacuo and the residue was dispersed between ethyl acetate and water. The organic layer was separated, dried ($MgSO_4$) and filtered and the solvent was removed in vacuo to afford a crystalline solid. $^1H$ NMR (250 MHz, $CDCl_3$) d 2.42 (3H, s, $ArCH_3$), 4.84 (2H, s, $CH_2O$), 7.00 (1H, d, J=1.5 Hz, imidazole-H), 7.36 (2H, d, J=8.0 Hz, ArH), 7.40 (1H, d, J=1.5 Hz, imidazole-H), 7.84 (2H, d, J=8.0 Hz, ArH).

(c) ((N-p-Toluenesulfonyl)imidazol-2-yl)methyl methanesulfonate

The alcohol described in (b) above (12.6 mg) was dissolved in dichloromethane (2.5 ml) and triethylamine (0.07 ml). This solution was cooled to 0° C. Methanesulfonyl chloride (0.04 ml) was added to the solution dropwise. After stirring for 10 mins the solution was diluted with water and the organic layer was separated, dried ($MgSO_4$), filtered and the solvent removed in vacuo to yield a white solid which was used in the following reaction without further purification. $^1H$ NMR (250 MHz, $CDCl_3$) d 2.44 (3H, s, ArH), 2.94 (3H, s, $SO_2CH_3$), 5.51 (2H, s, $CH_2SO_2$), 7.08 (1H, d, J=1.5 Hz, imidazole-H), 7.40 (2H, d, J=8.0 Hz, ArH), 7.49 (1H, d, J=1.5 Hz, imidazole-H), 7.92 (2H, d, J=8.0 Hz, ArH).

(d) ((N-p-Toluenesulfonyl)imidazol-2-yl)methylmethanesulfonate (1.6 g) was added to a suspension of the compound of Description 3 (2.47 g) and potassium carbonate (800 mg) in dimethylformamide (10 ml) and the resulting mixture was heated at 100° C. for 2 h. The mixture was cooled, diluted with water (100 ml) and extracted with ethyl acetate (3×20 ml). The organic extracts were combined, washed with brine, dried ($MgSO_4$) and concentrated in vacuo. This afforded a colourless oil which was purified by column chromatography on silica using 25–30% ethyl acetate in hexane. This afforded the product as a white crystalline solid which was recrystallised from dichloromethane/petrol: mp 125°–126° C. $^1H$ NMR (360 MHz, DMSO-$d_6$) d 1.4–1.5 (1H, m, $NCH_2CH_2CHH$), 1.5–1.67 (1H, m, $NCH_2CH_2CHH$), 1.8–2.0 (1H, m, $NCH_2CHH$), 2.06–2.1 (1H, m, $NCH_2CHH$), 2.35 (3H, s, $CH_3$), 2.4 (1H, mc, NCHH), 2.7–2.86 (1H, m, NCHH), 3.50 (1H, d, J=14.0 Hz, CHH-imidazole), 3.56 (1H, brs, CHO), 3.76 (1H, d, J=1.5 Hz, CHPh), 4.08 (1H, d, J= 14.0 Hz, CHH-imidazole), 4.09 (1H, d, J=12.0 Hz, OCHH), 4.48 (1H, d, J=12.0 Hz, OCHH), 6.96 (1H, d, J=1.0 Hz, imidazole-H), 7.12 (2H, d, J=8.5 Hz, ArH), 7.2–7.3 (3H, m, ArH), 7.34 (1H, d, J=1.0 Hz, imidazole-H), 7.46–7.58 (2H, m, ArH), 7.60 (2H, s, ArH), 7.71 (1H, ArH), 7.79 (2H, d, J=8.5 Hz, ArH); MS ($CI^+$) m/z 638 ($M^+$+1). Found: C, 58.48; H, 4.78; N, 6.72; S, 4.81. Calcd. for $C_{31}H_{29}F_6N_3O_3S$: C, 58.39; H, 4.58; N, 6.59; S, 5.03%.

EXAMPLE 33

2-[{2S,3S)-3-((3,5-Bis(trifluoromethyl)phenyl)methyloxy- 2-phenylpiperidino}methyl]imidazole dihydrochloride The compound of Example 32 was dissolved in dichloromethane and ethereal hydrogen chloride was added. The resulting solution was stirred for 30 minutes whereupon the title compound crystallised from solution. This was removed by filtration and recrystallised from ethyl acetate/methanol to afford the title compound as a white crystalline compound. $^1H$ NMR (360 MHz, $D_2O$) d 1.61–1.74 (1H, m, CHH), 1.76–1.88 (1H, m, CHH), 2.04–2.21 (2H, m, $CH_2$), 3.07–3.23 (1H, m, NCHH), 3.41–3.51 (1H, m, NCHH), 3.66 (1H, s, CHO), 4.09 (1H, d, J=13.0 Hz, OCHH), 4.25 (1H, d, J=15.5 Hz, CHH-imidazole), 4.30 (1H, s, CHPh), 4.39 (1H, d, J=15.5 Hz, CHH-imidazole), 4.55 (1H, d, J=13.0 Hz, OCHH), 7.1–7.2 (3H, m, ArH), 7.2–7.3 (2H, m, ArH), 7.38 (2H, s, imidazole-H), 7.48 (2H, s, ArH), 7.51 (1H, s, ArH); MS ($CI^+$) m/z 484 ($M^+$+1, 25%). Found: C, 50.32; H, 4.92; N, 7.23; Cl, 12.58. Calcd. for $C_{24}H_{23}F_6N_3O.2HCl.H_2O$: C, 50.18; H, 4.74; N, 7.32; Cl, 12.34%.

EXAMPLE 34

4-[{2S,3S )-3-((3,5-Bis(trifluoromethyl)phenyl)methyloxy-2-phenylpiperidino}methyl]imidazole dihydrochloride This was prepared following the procedure described for Example 33 using the compound of Description 3 and 4-(hydroxymethyl)imidazole as starting materials. This afforded the title compound as a white crystalline compound: mp 206°–210° C. $^1$H NMR (360 MHz, D$_2$O) d 1.73 (1H, m, NCH$_2$CH$_2$CHH), 1.94–2.06 (1H, m, NCH$_2$CH$_2$CHH), 2.22–2.40 (2H, m, NCH$_2$CH$_2$), 3.33 (1H, mc, NCHH), 3.70–3.81 (1H, m, NCHH), 3.97 (1H, brs, CHO), 4.30 (1H, d, J=12.5 Hz, OCHH), 4.42 (2H, s, NCH$_2$-imidazole), 4.50 (1H, s, NCHPh), 4.75 (1H, d, J=12.5 Hz, OCHH), 7.48 (6H, brs, ArH+imidazole-H), 7.74 (2H, s, ArH), 7.95 (1H, s, ArH), 8.80 (1H, s, imidazole-H); MS (CI$^+$) m/z 484 (M$^+$+1 Found: C, 50.22; H, 4.82; N, 7.18; Cl, 12.49. Calcd. for C$_{24}$H$_{23}$F$_6$N$_3$O.2HCl.H$_2$O: C, 50.18; H, 4.74; N, 7.32; Cl, 12.34%

EXAMPLE 35

5-[{(2R*,3R*)-3-((3,5-Bis(trifluoromethyl)phenyl)methyloxy)-2-phenylpiperidino}methyl]-2,3-dihydro-(4H)-3-oxo- 1,2,4-triazole hydrochloride (a) N-Carbomethoxy-2-chloroacetamidrazone Sodium methoxide (0.032 g) was added to a solution of chloroacetonitrile (1.26 ml) in anhydrous methanol (15 ml) at 0° C. The reaction mixture was stirred at room temperature for 0.5 hour and then neutralised with acetic add (0.034ml). Methyl hydrazinocarboxylate (1.79 g) was added and the reaction mixture stirred at room temperature for 0.5 hour. The solution was concentrated in vacuo to give the title compound as an orange solid. MS (CI)$^+$ m/z 166.

(b) The compound of Description 1 (0.50 g) was stirred with N-carbomethoxy-2-chloroacetamidrazone (0.19 g) and potassium carbonate (0.47 g) in dimethylformamide (10 ml) at 70° C. for 18 hours. The reaction mixture was then stirred at 140° C. for 1 hour. After cooling, the material was partitioned between ethyl acetate and water. The organic layer was washed with water, dried (MgSO$_4$), filtered and concentrated. The residue was purified by chromatography on silica using 5% methanol in ethyl acetate as eluent. The product was recrystallised from ethyl acetate/petrol to give the title compound as a white crystalline solid. This was characterised as its hydrochloride salt: mp 168°–172° C. MS (CI)$^+$ m/z 500 ((M+1)$^+$, 18%). Found: C, 50.65; H, 4.43; N, 10.22; Cl, 6.71. Calcd. for C$_{23}$H$_{24}$N$_4$O$_{2.5}$F$_6$Cl: C, 50.60; H, 4.43; N, 10.26; Cl, 6.49%.

EXAMPLE 36

5-[{(2R*,3R*)-3-((3,5-Bis(trifluoromethyl)phenyl)methyloxy)-2-phenylpiperidino}methyl]-3-(N,N-dimethylamino)- 1,2,4-thiadiazole (a) 5-(N,N-Dimethylamino)-1,3,4-oxathiazolin-2-one A solution of chlorocarbonylsulfenyl chloride (11.5 g) in acetonitrile was added to a suspension of N,N-dimethylurea (25.0 g) in acetonitrile (200 ml), over a period of 20 minutes. The reaction mixture was stirred for 1 hour at 23° C., then filtered. Methanol (20 ml) was added to the filtrate to decompose excess chlorocarbonylsulfenyl chloride. The solvents were removed in vacuo. The residue was purified by chromatography on silica using dichloromethane in hexane (3:1) to afford the product as a yellow oil. $^1$H NMR (250 MHz, CDCl$_3$) d 3.04 (6H, s, (CH$_3$)$_2$); MS (CI$^+$) m/z 164 (M$^+$+NH$_4$$^{+)}$ (b) 5-(Chloromethyl)-3-(N,N-dimethylamino)thiadiazole Chloroacetonitrile (1.3 ml) in dimethylformamide (1 ml) was heated to 150°–155° C. and 5-(N,N-dimethylamino)-1,3,4-oxathiazolin-2-one (1.0 g) was added in portions. After 5 minutes the reaction mixture was cooled and concentrated in vacuo. The residue was purified by chromatography on silica using hexane/ethyl acetate (9:1) as eluent. This afforded the product as a white crystalline solid. $^1$H NMR (250 MHz, CDCl$_3$) d 3.19 (6H, s, (CH$_3$)$_2$), 4.82 (2H, s, CH$_2$); MS (CI$^+$) m/z 178

(c) 5-[{(2R*,3R*)-3-((3,5-Bis(trifluoromethyl)phenyl)methyloxy)-2-phenylpiperidino}methyl]-3-(N,N-dimethylamino)- 1,2,4-thiadiazole hydrochloride The compound of Description 1 was reacted with 5-(chloromethyl)-3-(N,N-dimethylamino)thiadiazole according to the procedure described in Example 4. This afforded the title compound as a white solid: mp 160°–161° C.; $^1$H NMR (360 MHz, DMSO-d$_6$+TFA) d 1.69–1.87 (2H, m, CH$_2$), 2.01–2.26 (2H, m, CH$_2$), 3.10 (6H, s, (CH$_3$)$_2$), 3.22–3.34 (1H, m, CHH), 3.64–3.72 (1H, m, CHH), 3.90 (1H, s, CHO), 4.26–4.34 (2H, m, CH$_2$), 4.61 (1H, d, J=20.0 Hz, OCHH), 4.76–4.82 (2H, m, OCHH+CHPh), 7.36–7.62 (5H, m, ArH), 7.87 (2H, s, ArH), 7.99 (1H, s, ArH).

EXAMPLE 37

5-[{(2S,3S)-3-((3,5-Bis(trifluoromethyl)phenyl)methyloxy)- 2-phenylpiperidino}methyl]tetrazole This compound was prepared according to the procedure described in Example 7, using the compound of Description 9 as a starting material: mp 179°–181° C. MS (CI$^+$) m/z 486 (MH$^+$, 35%). Found: C, 54.61; H, 4.53; N, 14.37. Calcd. for C$_{22}$H$_{21}$F$_6$N$_5$O: C, 54.43; H, 4.36; N, 14.43%.

EXAMPLE 38

5-[{2S,3S)-3-((3,5-Bis(trifluoromethyl)phenyl)methyloxy)- 2-phenylpiperidino}methyl]-2-methyltetrazole This compound was prepared according to the procedure described in Example 18 using the compound of Example 37 as a starting material. This afforded the title compound as a white crystalline material: mp 158°–159° C. MS (CI$^+$) m/z 500 (MH$^+$, 70%). Found: C, 55.84; H, 4.66, N, 14.13. Calcd. for C$_{23}$H$_{23}$F$_6$N$_5$O: C, 55.31; H, 4.64; N, 14.02%.

EXAMPLE 39

5-[{(2S,3S)-3-((3,5-Bis(trifluoromethyl)phenyl)methyloxy)- 2-phenylpiperidino}methyl]-1-methyltetrazole This compound was prepared according to the procedure described in Example 19 using the compound of Example 37 as a staring material. This afforded the title compound as a clear oil. MS (CI$^+$) 500 (MH$^+$, 40%). Found: C, 55.27; H 4.69; N, 13.67. Calcd. for C$_{23}$H$_{23}$F$_6$N$_5$O: C, 55.31; H, 4.64; N, 14.02%.

EXAMPLE 40

3-[{(2S,3S)-3-((3,5-Bis(trifluoromethyl)phenyl)methyloxy)- 2-phenylpiperidino}methyl]pyridazine (a) 3-(Hydroxymethyl)-1,2-pyridazine 1,2-pyridazine-3-carboxaldehyde (0.89 g) (G. Heinisch, E. Luszczak and M. Pailer, Mh. Chem 104, 1372 (1973)) was dissolved in water and sodium borohydride (0.081 g)

was added carefully. After 1 hour no starting material was present by TLC using 10% methanol in dichloromethane as eluent. The water was removed in vacuo to afford a gum. The gum was extracted with dichloromethane, the combined organics were dried (MgSO$_4$) and concentrated in vacuo to afford the alcohol as a solid, which was used in the following experiment without further purification. $^1$H NMR (360 MHz, CDCl$_3$) d 5.04 (2H, s, CH$_2$OH), 7.54 (1H, dd, pyridazine-H), 7.65 (1H, dd, pyridazine-H), 9.17 (1H, dd, pyridazine-H).

(b) 3-[{(2S,3S)-3-((3,5-Bis(trifluoromethyl)phenyl)methyloxy)-2-phenylpiperidino}methyl]pyridazine 3-(Hydroxymethyl)-1,2-pyridazine was dissolved in anhydrous dichloromethane under an atmosphere of nitrogen and cooled in an ice/water bath. Triethylamine (0.68 ml) and methanesulfonyl chloride (0.378 ml) were added and the reaction stirred for 1 hour. No starting material was present by TLC using 5% methanol in dichloromethane as eluent. The solvent was removed in vacuo to afford a solid. The compound of Description 3 (0.48 g of free base) was dissolved in dimethylformamide (5 ml) and added to the solid followed by potassium carbonate (0.85 g). The mixture was heated at 60° C. for 12 hours then poured into water (75 ml), extracted with ethyl acetate (3×40 ml), dried (MgSO$_4$) and concentrated to afford a brown oil. This was purified by chromatography on silica gel using a gradient elution of 10–30% ethyl acetate in petrol. Further purification was carried out by medium pressure chromatography; elution with 50/50 ethyl acetate/petrol afforded the title compound as a white solid: mp 111°–113° C. $^1$H NMR d (360 MHz, DMSO-d$_6$) 1.43–1.66 (2H, m, NCH$_2$CH$_2$CH$_2$), 1.77–1.91 (1H, m, NCH$_2$CHH), 2.13–2.24 (2H, m, NCHHCHH), 2.75–2.87 (1H, NCHH), 3.27–3.35 (1H, d, NCHH-pyridazine), 3.57–3.70 (2H, NCHPh+CHO), 3.83–3.93 (1H, d, NCHH-pyridazine), 4.14 (1H, d, J=13 Hz, OCHHAr), 4.66 (1H, d, J=13 Hz, OCHHAr), 7.23–7.35 (3H, m, Ar—H), 7.50–7.56 (2H, m, ArH), 7.66 (2H, s, pyridazine-H), 7.71 (2H, s, ArH), 7.94 (1H, s, ArH), 9.11 (1H, m, 4H) MS (CI$^+$) m/z 496 ((M$^+$+1), 30%)

EXAMPLE 41

2-[{(2S,3S)-3-((3,5-Bis(trifluoromethyl)phenyl)methyloxy)- 2-phenylpiperidino}methyl]-1,3,5-triazine The compound of Description 3 (2 g), chloroacetamidine hydrochloride (1.17 g) and diisopropylethylamine (3.17 ml) were dissolved in acetonitrile (10 ml) and the resulting mixture was stirred at 60° C., under nitrogen, for 12 h. The resulting mixture was evaporated and the residue was dispersed between ethyl acetate and water. The aqueous layer was extracted with ethyl acetate (2×50 ml) and dichloromethane (2×50ml). The combined organic fractions were washed with brine, dried (MgSO$_4$) and evaporated. The residue was purified by chromatography on silica using 5% methanol in dichloromethane and gradient elution to 10% methanol, 1% aqueous ammonia in dichloromethane. This afforded the intermediate amidine as a semi-solid material, which was not further purified.

The intermediate amidine (2 g) and 1,3,5-triazine (0.35 g) were dissolved in acetonitrile (7 ml) and heated at reflux for 12 h. The solution was cooled and evaporated and the residue was purified by chromatography on silica using 50% petrol in ethyl acetate as eluent. This afforded the product as a crystalline solid which was recrystallised from hexane: mp 117°–119° C. $^1$H NMR (360 MHz, DMSO-d$_6$) δ 1.41–1.60 (2H, m, NCH$_2$CH$_2$CH$_2$), 1.81– 1.94 (1H, m, NCH$_2$CHH), 2.12–2.21 (1H, m, NCH$_2$CHH), 2.34– 2.41 (1H, m, NCHH), 2.99–3.06 (1H, m, CHH), 3.26–3.30 (1H, J=15.0 Hz, NCHH-triazine), 3.61 (1H, bs, CHO), 3.71 (1H, bs, CHPh), 3.80 (1H, d, J=15.0 Hz, NCHH-triazine), 4.08 (1H, d, J=13.0 Hz, OCHHAr), 4.63 (1H, d, J=13.0 Hz, OCHHAr), 7.18–7.29 (3H, m, ArH), 7.48–7.52 (2H, m, ArH), 7.68 (2H, s, ArH), 7.13 (1H, s, ArH), 9.20 (2H, s, triazine-H). MS (CI$^+$) m/z, 497 (M$^+$+1, 100%).

EXAMPLE 42

5-[{(2S,3S)-3-((3-t-Butyl-5-methylphenyl)methyloxy)- 2-(phenylpiperidino}methyl]-2,3-dihydro-3-oxo-1,2,4-triazole The compound of Description 10 was reacted according to the procedure described in Example 35 to afford the title compound as a crystalline solid: mp 185°–187° C. $^1$H NMR (360 MHz, CDCl$_3$) δ 1.22 (10H, m, C(CH$_3$)$_3$+ NCH$_2$CH$_2$CHH), 1.38–1.58 (2H, m, NCH$_2$CHHCHH), 1.98–2.26 (5H, m, CH$_3$+ NCHHCHH), 2.89 (1H, d, J=15.0 Hz, NCHH-triazole), 2.96–3.04 (1H, m, NCHH), 3.29 (1H, bs, CHO), 3.56 (1H, bs, CHPh), 3.65 (1H, J=15.0 Hz, NCHH-triazole), 4.13 (1H, d, J=12.0 Hz, OCHHAr), 4.28 (1H, d, J=12.0 Hz, OCHHAr), 6.53 (1H, s, ArH). 6.89 (1H, s, ArH), 7.00 (1H, s, ArH), 7.26–7.38 (3H, m, ArH), 7.45–7.50 (2H, m, ArH). MS (CI$^+$) m/z 435 (M$^+$+1, 60%). Found: C, 72.10; H, 7.94; N, 13.05. Calcd for C$_{26}$H$_{34}$N$_4$O$_2$: C, 71.86; H, 7.89; N, 12.89%.

EXAMPLE 43

2-[{(2S,3S)-3-((3,5-Dichlorophenyl)methyloxy)- 2-(phenylpiperidino}methyl]imidazole dihydrochloride The compound of Description 11 was reacted according to the procedure described in Examples 32/33, to afford the title compound: mp 129°–131° C. $^1$H NMR (360 MHz, DMSO-d$_6$) δ 1.84– 1.98 (2H, m, NCH$_2$CH$_2$CH$_2$), 2.14–2.24 (1H, m, NCH$_2$CHH), 2.44–2.62 (1H, m, NCH$_2$CHH), 3.09–3.20 (1H, m, NCHH), 3.69– 3.86 (2H, m, NCHH+ CHO), 4.25 (1H, d, J=13.0 Hz, OCHHAr), 4.53 (1H, d, J=13.0 Hz, OCHHAr), 4.83 (1H, d, J=15.0 Hz, NCHH-imidazole), 4.91 (1H, bs, CHPh), 5.14 (1H, d, J=15 Hz, NCHH-imidazole), 7.16–7.48 (10H, m, ArH), 7.84 (1H, bs, N—H). MS (CI$^+$) m/z 415 (M+1$^+$, 70%). Found: C, 50.71; H, 5.28; N, 8.05. C$_{22}$H$_{23}$Cl$_2$N$_3$O.2HCl.2H$_2$O requires: C, 50.30; H, 5.56; N, 7.99%.

EXAMPLE 44

5-[{(2S,3S)-3-((3-Chloro-5-methylphenyl)methyloxy)- 2-phenylpiperidino}methyl]-2,3-dihydro-3-oxo-1,2,4-triazole The compound of Description 12 was reacted according to the procedure described in Example 35 to afford the title compound as a white crystalline solid: mp 227°–228° C. $^1$H NMR (360 MHz, DMSO-d$_6$) δ 1.35–1.55 (2H, m, NCH$_2$CH$_2$CH$_2$), 1.78– 1.88 (1H, m, NCH$_2$CHH), 2.06–2.13 (2H, m, NCHHCHH), 2.20 (3H, s, CH$_3$), 2.73 (1H, d, J=14.0 Hz, NCHH-triazole), 2.89 (1H, d, J=11.0 Hz, NCHH), 3.32–3.39 (1H, m, CHO), 3.42 (1H, d, J=14.0 Hz, NCHH-triazole), 3.47 (1H, s, CHPh), 3.86 (1H, d, J=12.0 Hz, OCHH), 4.29 (1H, d, J=12.0 Hz, OCHH), 6.65 (1H, s, ArH), 6.79 (1H, s, ArH), 7.07 (1H, s, ArH), 7.25–7.34 (3H, m, ArH), 7.51–7.53 (2H, m, ArH). MS (CI⁺) m/z 412 (M⁺+1, 20%). Found: C, 64.30; H, 6.13; N, 13.67. $C_{22}H_{25}ClN_4O_2$ requires: C, 63.99; H, 6.10; N, 13.57%.

EXAMPLE 45

5-[{(2S,3S)-3-((3,5-Bis(trifluoromethyl)phenyl)methyloxy-2-(diphenylmethyl)pyrrolidino}methyl]-2,3-dihydro-3-oxo-1,2,4-triazole The compound of Description 13 was reacted with N-carbomethoxy- 2-chloroacetamidrazone according to the procedure described in Example 35 to afford the product as a white crystalline solid. ¹H NMR (250 MHz, CDCl₃) δ 1.92 (2H, m), 2.62 (1H, m), 2.90 (1H, d, J=15 Hz), 3.14 (2H, m), 3.78 (2H, m), 4.08 (1H, m), 4.28 (2H, m), 7.1–7.4 (10H, m, ArH), 7.48 (2H, s, ArH), 7.77 (1H, s, ArH). MS (CI⁺) m/z 577 (M⁺+1, 100%).

EXAMPLE 46

5-[{(2R,3S)-3-((3,5-Bis(trifluoromethyl)phenyl)methyloxy-2-(diphenylmethyl)pyrrolidino}methyl]-2,3-dihydro-3-oxo-1,2,4-triazole The compound of Description 14 was reacted with N-carbomethoxy- 2-chloroacetamidrazone according to the procedure described in Example 35 to afford the title compound as a white crystalline solid. ¹H NMR (360 MHz, CDCl₃) δ 2.00 (2H, m), 2.69 (1H, m), 3.03 (1H, t, J=7.5 Hz), 3.26 (1H, d, J=14.5 Hz), 3.32 (1H, d, J=14.5 Hz), 3.68 (2H, s), 3.76 (1H, d, J=3.5 Hz), 4.31 (1H, d, J=12.5 Hz), 4.42 (1H, d, J=12.5 Hz), 7.40– 7.19 (10H, m, ArH), 7.64 (2H, s, ArH), 7.76 (1H, s, ArH). MS (CI⁺) m/z 577 (M⁺+1, 100%).

EXAMPLE 47

3-[{2S,3S)-3-((3,5-Dichlorophenyl)methyloxy)-2-(diphenylmethyl)pyrrolidino}methyl]-1,2,4-triazole The compound of Description 15 was reacted with N-formyl- 2-chloroacetamidrazone according to the procedure in Example 16 to afford the title compound as a crystalline solid: mp 128°–129° C. ¹H NMR (360 MHz, DMSO-d₆) δ 1.65 (1H, brs), 1.76 (1H, brs), 3.10 (2H, m), 3.61 (1H, d, J=12.0 Hz), 3.92 (1H, brs), 4.01 (1H, brs), 4.22 (2H, m), 7.02 (2H, d, J=1.8 Hz, ArH), 7.10 (1H, m, ArH), 7.14 (3H, m, ArH), 7.22 (2H, t, ArH), 7.39 (2H, d, ArH), 7.46 (3H, m, ArH). MS (CI⁺) m/z 493 (M⁺+1, 60%). Found: C, 65.95; H, 5.22; N, 11.33. Calcd for $C_{27}H_{26}Cl_2N_4O$: C, 65:72; H, 5.31; N, 11.35%.

EXAMPLE 48

5-[{(2S,3S)-3-((3-t-Butyl-5-chlorophenyl)methyloxy)- 2-phenylpiperidino}methyl]-2,3-dihydro-3-oxo-1,2,4-triazole The compound of Description 16 was reacted with N-carbomethoxy- 2-chloroacetamidrazone, according to the procedure described in Example 35, to afford the title compound as a white crystalline solid: mp 181°14 182° C. MS (CI⁺) m/z 455 (M⁺+1, 100%). Found: C, 65.99; H, 6.87; N, 12.31. Calcd for $C_{25}H_{31}ClN_4O$: C, 66.47; H, 6.91; N, 12.45%.

EXAMPLE 49

5-[{(2S,3S)-3-((3-Bis(trifluoromethyl)phenyl)methyloxy- 2-phenylpiperidino}methyl]-2,3-dihydro-3-oxo-1,2,4-triazole hydrochloride The title compound was prepared according to the procedure described in Example 35, using the compound of Description 3 as starting material. The hydrochloride salt was recrystallised from ethyl acetate-methanol to give a white crystalline solid: mp 265°–266° C. ¹H NMR (360 MHz, DMSO-d₆+ TFA) δ 1.75–1.95 (2H, m, CH₂), 2.04–2.30 (2H, m, CH₂), 3.20–3.32 (1H, m, NCHH), 3.58–3.69 (1H, m, NCHH), 3.90 (1H, d, J=15.0 Hz, NCHH-triazole), 3.93 (1H, s, CHO), 3.94.(1H, d, J=15.0 Hz, NCHH-triazole), 4.30 (1H, d, J=12.0 Hz, OCHH), 4.73 (1H, bs, CHPh), 4.80 (1H, d, J=12.0 Hz, OCHH), 7.42 (3H, brs, ArH), 7.56 (2H, brs, ArH), 7.89 (2H, s, ArH), 7.95 (1H, s, ArH). MS (CI⁺) m/z 501 (M⁺+1), 60%). Found: C, 51.41; H, 4.15; N, 10.58; Cl, 6.46. Calcd for $C_{23}H_{22}F_6N_4O.HCl$: C, 51.45; H, 4.32; N, 10.44; Cl, 6.60%.

EXAMPLE 50

3-[{(2S,3S)-3-((3,5-Bis(trifluoromethyl)phenyl)methyloxy)- 2-phenylpiperidino}methyl]-1-methyl-1,2,4-triazole hydrochloride The compound of Example 30 (0.5 g) was dissolved in methanol in a tube. Sodium (0.03 g) and iodomethane (0.075 ml) were added and the container was sealed. The resulting solution was heated at 65° C. for 1 h, cooled and evaporated. The residue was suspended between water and ethyl acetate. The organic layer was dried (MgSO₄), filtered and the solvent removed in vacuo. The residue was purified by chromatography on silica using ethyl acetate as eluent. This afforded the product as a colourless oil, which was converted to the hydrochloride salt by addition of ethereal hydrogen chloride. The salt was recrystallised from ether/petrol. ¹H NMR (360 MHz, DMSO-d₆) δ 1.70–1.84 (2H, m, CH₂), 2.12–2.51 (2H, m, CH₂), 3.36 (3H, s, NCH₃), 3.52 (1H, brs, CHHN), 3.73 (1H, brs, CHHN), 3.87 (1H, s, CHO), 4.25 (2H, m, CHH-triazole), 4.28 (1H, d, OCHHAr), 4.65 (1H, brs, NCHPh), 4.78 (1H, d, OCHHAr), 7.41 (3H, s, ArH), 7.60 (2H, brs, ArH), 7.93 (2H, s, ArH), 7.96 (1H, s, ArH), 8.05 (1H, s, CH=NH (triazole)); MS (CI⁺) m/z 499 (M⁺+1, 85%).

EXAMPLE 51

3-[{(2S,3S)-3-((3,5-Bis(trifluoromethyl)phenyl)methyloxy)- 2-phenylpiperidino}methyl]-5-phenyl-1,2,4-oxadiazole hydrochloride The compound of Description 3 was reacted with 3-chloromethyl-5-phenyl-1,2,4-oxadiazole according to the procedure described in Example 26. The product was characterised as its hydrochloride salt: mp 88°–90° C. ¹H NMR (360 MHz, CDCl₃, free base) δ 1.50–1.64 (2H, m, CH₂), 2.06–2.22 (2H, m, CH₂), 2.44–2.56 (1H, m, CHHN), 3.18–3.28 (1H, m, CHHN), 3.60 (1H, s, CHO), 3.66–3.74 (1H, d, J=15.0 Hz, NCHH-oxadiazole), 3.78 (1H, s, CHPh), 3.88–3.98 (1H, d, J=15.0 Hz, NCHH-oxadiazole), 4.02–4.10 (1H, d, J=12.0 Hz, OCHHAr), 4.44– 4.52 (1H, d, J=12.0 Hz, OCHHAr), 7.28–7.64 (10H, m, ArH), 7.68 (1H, s, ArH), 8.08–8.18 (2H, m, ArH); MS (CI⁺) m/z 562 (M⁺+1).

EXAMPLE 52

3-[{(2R*,3R*)-3-((3,5-Bis(trifluoromethyl)phenyl)methyloxy)-2-phenylpiperidino}methyl]-5-thiomethyl-1,2,4-triazole hydrochloride Sodium methoxide (0.001 g) was added to a solution of the compound of Example 17 (0.10 g) in ethanol (5 ml) and the mixture was heated at reflux for 10 min. Methyl iodide (0.012 ml) in ethanol (1 ml) was added and the mixture was heated at reflux for 3 h. The solvent was then removed in vacuo and the residue was partitioned between ethyl acetate and water. The organic layer was dried ($MgSO_4$) and concentrated in vacuo. The residue was purified by chromatography on silica using 50% ethyl acetate in petrol as eluent. The compound was isolated as the hydrochloride salt by treatment of the free base with methanolic hydrogen chloride: mp 105°–107° C. $^1$H NMR (360 MHz, DMSO-$d_6$+ TFA) δ 1.73–1.91 (2H, m, $CH_2$), 2.05–2.20 (1H, m, CHH), 2.21–2.30 (1H, m, CHH), 2.63 (3H, s, $CH_3$), 3.28 (1H, m, $NCHHCH_2$), 3.73 (1H, m, $NCHHCH_2$), 3.92 (1H, brs, CHO), 4.10 (2H, dd, J=20 Hz, 14.5 Hz, $NCH_2$), 4.29 (1H, d, J=13 Hz, OCHH), 4.68 (1H, s, CHPh), 4.79 (1H, d, J=13 Hz, OCHH), 7.42–7.48 (3H, m, ArH), 7.57 (2H, brs, ArH), 7.88 (2H, s, ArH), 7.95 (1H, s, ArH). MS ($CI^+$) m/z 531 ($M^+$+1, 44%). Found: C, 51.29; H, 4.62; N, 9.79; Cl, 6.06. Calcd for $C_{29}H_{24}F_6N_4OS$.HCl: C, 50.84; H, 4.44; N, 9.88; Cl, 6.25%.

EXAMPLE 53

5-[{(2S,3S)-3-((3,5-Dichlorophenyl)methyloxy)-2-phenylpiperidino}methyl]-2,3-dihydro-3-oxo-1,2,4-triazole The compound of Description 11 was reacted according to the procedure described in Example 35 to afford the title compound which was recrystallised from hot dimethylformamide: mp >220° C. $^1$H NMR (360 MHz, DMSO-$d_6$, 353K) δ 1.45–1.58 (2H, m, $CH_2$), 1.81–1.95 (1H, m, CHH), 2.02–2.12 (1H, m, CHH), 2.18 (1H, dt, J=2.5, 11.5 Hz, $NCHHCH_2$), 2.82 (1H, d, J=14.2 Hz, NCHH), 2.94 (1H, brd, $NCHHCH_2$), 3.40 (1H, d, J=14.5 Hz, NCHH), 3.45 (1H, d, CHO), 3.52 (1H, d, CHPh), 3.91 (1H, d, J=12.5 Hz, OCHH), 4.34 (1H, d, J=12.5 Hz, OCHH), 7.21–7.37 (5H, m, ArH), 7.47–7.55 (3H, m, ArH).

EXAMPLE 54

4-[{(2R*,3R*)-3-((3-Carbomethoxyphenyl)methyloxy)-2-phenylpiperidino}methyl]pyridinium dichloride The compound of Description 17 was reacted with 4-picolyl chloride according to the procedure described in Example 4 to afford the title compound. $^1$H NMR (250 MHz, $CDCl_3$) δ 1.42–1.61 (2H, m, $NCH_2CH_2CH_2$), 1.98–2.18 (3H, m, $NCHHCH_2$), 2.87–3.04 (2H, m, NCHH-pyridine+NCHH), 3.31–3.39 (1H, m, CHO), 3.48–3.54 (1H, m, NCHPh), 3.86 (1H, d, J=14 Hz, NCHH-pyridine), 3.93 (3H, s, $OCH_3$), 4.06 (1H, d, J=11 Hz, OCHHAr), 4.30 (1H, d, J=11 Hz, OCHHAr), 7.12 (1H, m, ArH), 7.22–7.39 (6H, m, ArH), 7.45–7.56 (2H, dd, pyridine-H), 7.77 (1H, bs, ArH), 7.85–7.92 (1H, ArH), 8.46–8.55 (2H, dd, pyridine-H). MS ($CI^+$) m/z 417 ($M^+$+1, 50%). Found: C, 64.10; H, 6.06; N, 5.62. $C_{26}H_{28}N_2O_3$.2HCl requires: C, 63.80; H, 6.18; N, 5.72%.

EXAMPLE 55

4-[{(2R*,3R*)-3-((3-Carboxamidophenyl)methyloxy)-2-phenylpiperidino}methyl]pyridine The compound of Description 18 was reacted with 4-picolyl chloride according to the procedure described in Example 4 to afford the title compound. $^1$H NMR (360 MHz, $CDCl_3$) 1.43–1.56 (2H, m, $NCH_2CH_2CH_2$), 2.00–2.17 (3H, m, $NCHHCH_2$), 2.88–3.04 (2H, m, NCHH+NCHHAr), 3.35 (1H, m, CHO), 3.54 (1H, bs, CHPh), 3.83 (1H, d, J=14.5 Hz, NCHHAr), 4.08 (1H, d, J=12 Hz, OCHHAr), 4.35 (1H, d, J=12 Hz, OCHHAr), 5.6–6.16 (2H, bs, $CONH_2$), 7.11–7.74 (11H, m, ArH), 8.48 (2H, d, J=4 Hz, pyridine-H). MS ($CI^+$) m/z 402 ($M^+$+1, 20%).

EXAMPLE 56

5-[{(2R*,3R*)-3-((2-Methoxy-3-nitrophenyl)methyloxy)-2-phenylpiperidino}methyl]-3-methyl-1,2,4-oxadiazole The compound of Description 19 was reacted according to the procedure described in Example 2 to afford the title compound. $^1$H NMR (360 MHz, $CDCl_3$) δ 1.48–1.64 (2H, m, $NCH_2CH_2CH_2$), 2.09–2.25 (2H, m, $NCH_2CH_2$), 2.37 (3H, s, $CH_3$), 2.41–2.51 (1H, m, NCHH), 3.12–3.20 (1H, m, NCHH), 3.59 (1H, bs, CHO), 3.64 (1H, bs, CHPh), 3.73 (1H, d, J=16 Hz, NCHH-het), 3.80 (3H, s, $OCH_3$), 3.91 (1H, d, J=16 Hz, NCHH-het), 3.98 (1H, d, J=13 Hz, OCHHAr), 4.48 (1H, d, J=13 Hz, OCHHAr), 6.78 (1H, d, J=9 Hz, H), 7.22–7.37 (3H, m, ArH), 7.48–7.54 (2H, bd, ArH), 8.09–8.14 (1H, dd, J=9 Hz, J=3 Hz, ArH), 8.15–8.18 (1H, d, J=3 Hz, ArH). MS ($CI^+$) m/z 439 ($M^+$+1, 100%).

EXAMPLE 57

3-Amino-5-[{(2R*,3R*)-3-((5-amino-2-methoxyphenyl) methyloxy)-2-phenylpiperidino}methyl]-1,2,4-oxadiazole The compound of Description 20 was reacted according to the procedure described in Example 1 to afford the title compound. $^1$H NMR (360 MHz, $CDCl_3$) δ 1.41–1.60 (2H, m, $NCH_2CH_2CH_2$), 2.13–2.24 (2H, m, $NCH_2CH_2$), 2.31 (1H, m, NCHH), 3.12–3.21 (1H, m, NCHH), 3.39 (1H, d, J=16 Hz, NCHH-het), 3.47 (1H, m, CHO), 3.56 (1H, m, NCHPh), 3.61 (3H, s, $OCH_3$), 3.82 (1H, d, J=16 Hz, NCHH-Het), 4.13 (1H, d, J=13 Hz, OCHHAr), 4.34 (1H, d, J=13 Hz, OCHHAr), 5.17 (2H, bs, $NH_2$), 6.38 (1H, bs, ArH), 6.43–6.48 (1H, m, ArH), 6.54–6.58 (1H, d, J=8.5 Hz, ArH), 7.26–7.58 (3H, m, ArH), 7.48–7.54 (2H, m, ArH).

EXAMPLE 58

6-[{(2S,3S)-3-((3,5-Bis(trifluoromethyl)phenyl)methyloxy)-2-phenylpiperidino}methyl]uracil The compound of Description 3 was reacted with 6-(chloromethyl)uracil following the conditions described in Example 4 to afford the title compound. $^1$H NMR (360 MHz, $CDCl_3$) 1.52–1.71 (2H, m, $NCH_2CH_2CH_2$), 1.99–2.25 (3H, m, $NCHHCH_2$), 2.69 (1H, d, J=16 Hz, NCHH-uracil), 2.92–3.01 (1H, m, NCHH), 3.38–3.40 (1H, m, CHO), 3.52–3.62 (2H, m, NCHH-uracil+NCHPh), 4.08 (1H, d, J=12 Hz, OCHHAr), 4.49 (1H, d, J=12 Hz, OCHHAr), 5.41 (1H, s, $H_A$), 7.32–7.40 (5H, m, ArH), 7.50 (2H, s, H), 7.56 (1H, s, H), 8.64–9.04 (2H, bs, NH+NH). MS ($CI^+$) m/z 528 ($M+1^+$, 100%). $C_{25}H_{23}N_3O_3F_6$ requires C, 56.93; H, 4.40; N, 7.97%. Found C, 57.16; H, 4.03; N, 7.88%.

EXAMPLE 59

3-[{(2R*,3R*)-3-((3,5- Bis(trifluoromethyl)phenyl) methyloxy)-2-phenylpiperidino}methyl]-5-carboxamido-1,2,4-triazole The compound of Description 1 was reacted with 2-chloro-N-carboxamidoacetamidhydrazone according to the procedure described in Example 35 to afford the title compound as a white solid: mp 195° C. $\upsilon_{max}$ (KBr) 1680 cm$^{-1}$; Found: C, 55.14; H, 4.58; N, 12.82. Calcd for $C_{24}H_{23}F_6N_5O_2$: C, 54.65; H, 4.40; N, 13.27%.

EXAMPLE 60

3-[{(2R*,3R*)-3-((3,5-Bis(trifluoromethyl)phenyl) methyloxy)-2-phenylpiperidino}methyl]-5-cyano-1, 2,4-triazole The compound of Example 59 (0.61 g) was dissolved in chloroform (10 ml) and the resulting solution was cooled to 0° C. in an ice bath. Triethylamine (2 ml) was added followed by phosphorus oxychloride (1.2 ml), dropwise. The solution was stirred at room temperature for 1 h. The solvent was removed in vacuo and the residue was dispersed between chloroform and sodium hydrogen carbonate. The organic layer was washed with brine, dried (MgSO$_4$), filtered and concentrated in vacuo. The residue was purified by column chromatography on silica using 30% petrol in ethyl acetate as eluent. The product was isolated as the hydrochloride salt using ethereal hydrogen chloride: mp 81° C. MS (CI$^+$) m/z 510 (M$^+$+1, 60%).

EXAMPLE 61

3-[(1S)-1-{(2S,3S)-3-((3,5-Dichlorophenyl)methyloxy)- 2-phenylpiperidino}ethyl]-1,2,4-triazole (a) (±) N-Formyl-2-chloropropionamidohydrazone Sodium methoxide (0.162 g) was added to a solution of 2-chloropropionitrile (10.5 g) in anhydrous methanol (150 ml ) at 0° C. The reaction mixture was stirred at room temperature for 1 h, then neutralised with acetic acid (0.18ml). N-Formylhydrazine (7.04 g) was added and the mixture was stirred overnight. The resulting pink solution was concentrated in vacuo to give the title compound as a pink solid.

(b) The compound of Description 11 (5.9 g) was dissolved in dimethylformamide (46 ml ) and N-formyl-2-chloropropionamidohydrazone (3.5 g) was added, followed by potassium carbonate (5.7 g). The mixture was stirred at room temperature for 2 h, then diluted with xylene (150 ml) and heated at reflux for 2 h. When cool, the mixture was filtered and concentrated in vacuo to afford a brown residue. Crude $^1$H NMR indicated a mixture of diastereoisomers in 3:1 ratio. The residue was purified by medium pressure chromatography (Lobar) on silica using 4% methanol in dichloromethane as eluent. The first product eluted, diastereoisomer 1, was isolated as a foam which was recrystallised from ether-hexane: mp 105°14 107° C. $^1$H NMR (360 MHz, CDCl$_3$) δ 1.31 (3H, d, J=7.0 Hz, —CHCH$_3$), 1.52–1.59 (2H, m, NCH$_2$CHHCHH), 2.02–2.05 (1H, m, NCH$_2$CHH), 2.05–2.16 (1H, m, NCH$_2$CH$_2$CHH), 2.51 (1H, t, J=11.5 Hz, NCHH), 2.62 (1H, m, NCHH), 3.56 (1H, s, CHO), 3.77 (1H, s, CHPh), 3.99 (1H, d, J=12.0 Hz, OCHH), 4.22 (1H, q, J=7.0 Hz, —CHCH$_3$), 4.30 (1H, d, J=12.0 Hz, OCHH), 6.89 (2H, d, J=2.0 Hz, ArH), 7.21 (1H, t, J=2.0 Hz, ArH), 7.3–7.4 (3H, m, ArH), 7.40–7.47 (2H, m, ArH), 7.89 (1H, s, triazole-2H). MS (CI$^+$) m/z.

EXAMPLE 62

3-[(1R)-1-{(2S,3S)-3-((3,5-Dichlorophenyl)methyloxy)- 2-phenylpiperidino}ethyl]-1,2,4-triazole The second product isolated from the column described in Example 61 was recrystallised from ether to afford the title compound whose stereochemistry was established from $^1$H NMR n.O.e. experiments: mp 132°–134° C. $^1$H NMR (360 MHz, DMSO-d$_6$) δ 1.06–1.15 (1H, m, NCH$_2$CH$_2$CHH), 1.35 (3H, d, J=7.0 Hz, CHCH$_3$), 1.34–1.42 (1H, m, NCH$_2$CHH), 1.66–1.85 (2H, m, NCHHCHH), 1.98–2.02 (1H, m, NCH$_2$CH$_2$CHH), 3.01–3.03 (1H, d, J=10.5 Hz, NCHH), 3.39 (1H, s, CHO), 3.86 (1H, d, J=13.0 Hz, OCHH), 3.98 (1H, q, J=7 Hz, CHCH$_3$), 4.33 (1H, d, J=13.0 Hz, OCHH), 6.92 (1H, d, J=2.0 Hz, ArH), 7.26–7.46 (6H, m, ArH,

EXAMPLE 63

3-[{(2S,3S)-3-((2,3-Dimethylphenyl)methyloxy)- 2-phenylpiperidino}methyl]-1,2,4-triazole Following the method described in Example 16, the compound of Description 23 (100 mg) was reacted with 69 mg of N-formyl-2-chloroacetamidohydrazone, to give the title compound. $^1$H NMR (CDCl$_3$) δ 1.50 (2H, m), 1.94 (3H, s), 2.0– 2.35 (3H, m), 2.2 (3H, s), 3.02 (1H, m), 3.45 (2H, m), 3.57 (1H, s), 3.95 (1H, br s), 3.95 (1H, d, J=11 Hz), 4.26 (1H, d, J=11 Hz), 6.86 (1H, d, J=7 Hz), 7.06 (1H, d, J=7 Hz), 7.2–7.5 (6H, m), 7.7 (1H, br s).

The following compounds were prepared by the procedure described in Example 35.

EXAMPLE 64

5-[{(2S,3S)-3-((2,3-Dimethylphenyl)methyloxy )- 2-phenylpiperidino}methyl]-2,3-dihydro-(4H )-3- oxo-1,2,4-triazole The compound of Description 23 was used as starting material. $^1$H NMR (CDCl$_3$) δ 1.4–1.55 (2H, m), 1.89 (3H, s), 1.9– 2.2 (3H, m), 2.15 (3H, s), 2.91 (1H, d, J=15 Hz), 2.95 (1H, m), 3.28 (1H, s), 3.50 (1H, s), 3.66 (1H, d, J=15 Hz), 4.06 (1H, d, J=12 Hz), 4.29 (1H, d, J=12 Hz), 6.77 (1H, d, J= 7 Hz), 6.9 (1H, t, J=7 Hz), 6.97 (1H, d, J=7 Hz), 7.2–7.45 (5H, m).

EXAMPLE 65

5-[{(2S,3S),2-Phenyl-3-((3-(trifluoromethyl)phenyl) methyloxy)piperidino}methyl]-3-oxo-1,2,4-triazole The compound of Description 21 was used as starting material. $^1$H NMR (CDCl$_3$) δ 1.5 (2H, m), 1.9–2.2 (3H, m), 2.91 (1H, d, J=15 Hz), 3.0 (1H, m), 3.3 (1H, s), 3.5 (1H, s), 3.64 (1H, d, J=15 Hz), 4.12 (1H, d, J=12 Hz), 4.41 (1H, d, J=12 Hz), 7.0–7.45 (9H, m), 9.9 (2H, br s).

EXAMPLE 66

5-[{(2S,3S)-3-((3,4-Dichlorophenyl)methyloxy)-2-phenylpiperidino}methyl]-3-oxo-1,2,4-triazole The compound of Description 22 was used as starting material. $^1$H NMR (CDCl$_3$) δ 1.5 (2H, m), 1.85–2.2 (3H, m), 2.88 (1H, d, J=15 Hz), 3.0 (1H, m), 3.27 (1H, s), 3.48 (1H, s), 3.67 (1H, d, J=15 Hz), 4.05 (1H, d, J=12 Hz), 4.35 (1H, d, J=12 Hz), 6.7 (1H, br d, J=7 Hz), 6.95 (1H, br s), 7.16 (1H, d, J=7 Hz), 7.2–7.45 (5H, m), 9.8 (1H, br s), 10.5 (1H, br s).

EXAMPLE 67

5-[{(2S,3S)-3-((3-t-Butylphenyl)methyloxy)-2-phenylpiperidino}methyl]-3-oxo-1,2,4-triazole The compound of Description 24 was used as starting material. $^1$H NMR (CDCl$_3$) δ 1.23 (9H, s, C(CH$_3$)$_3$), 1.40–1.51 (2H, m, CH$_2$), 1.82–1.85 (1H, m CHH), 2.01–2.14 (2H, m, CHH and NCHH), 2.74 (1H, d, J=14 Hz, NCHH-triazolone), 2.88 (1H, m, NCHH), 3.38 (1H, d, J=14 Hz, NCHH-triazolone), 3.40 (1H, m, NCHCHO), 3.51 (1H, s, NCHCHO), 3.85 (1H, d, J=12 Hz, OCHH), 4.23 (1H, d, J=12 Hz, OCHH), 6.80–6.82 (1H, m, ArH), 7.06–7.34 (6H, m, ArH), 7.53–7.55 (2H, m, ArH), 11.16 (1H, s, NH), 11.24 (1H, s, NH); MS (CI$^+$) m/z 420 (M$^+$+1, 10%). Found: C, 71.51; H, 7.51; N, 13.08. Cacld. for C$_{25}$H$_{32}$N$_4$O: C, 71.40; H, 7.67; N, 13.32%.

EXAMPLE 68

5-[{(2R*,3R*)-3-((3,5-Dimethylphenyl)methyloxy)-2-phenylpiperidino}methyl]-3-oxo-1,2,4-triazole The compound of Description 25 was used as starting material. $^1$H NMR (360 MHz, DMSO-d$_6$) δ 1.41–1.47 (2H, m, CH$_2$), 1.81–1.85 (1H, m, CHH), 2.05–2.11 (2H, m, CHH and NCHH), 2.15 (6H, s, CH$_3$), 2.72 (1H, d, J=14 Hz, NCHH-triazolone), 2.86–2.89 (1H, m, NCHH), 3.36 (1H, d, J=2.5 Hz, CHO), 3.40 (1H, d, J=14 Hz, NCHH-triazolone), 3.44 (1H, brs, CHPh), 3.82 (1H, d, J=12 Hz, OCHH), 4.20 (1H, d, J=12 Hz, OCHH), 6.50 (2H, s, ArH), 6.79 (1H, s, ArH), 7.25–7.33 (3H, m, ArH), 7.51–7.53 (2H, m, ArH), 11.16 (1H, s, NH), 11.25 (1H, s, NH).

EXAMPLE 69

(2S,3S)-3-((3,5,-Bis(trifluoromethyl)phenyl)methyloxy)-2-phenyl-1-(3-(1,2,4-triazolyl))piperidine 1-Hydroxybenzotriazole hydrate (308 mg), 1-(3-dimethylaminopropyl)- 3-ethylcarbodiimide hydrochloride (436 mg), triethylamine (0.3 ml) and 1,2,4-triazole-3-carboxylic acid (129 mg) were dissolved in dimethylformamide (5 ml) and the resulting mixture was stirred for 15 min. The compound of Description 3 (0.5 g) was added and the resulting mixture was stirred at room temperature for 12 h. The reaction mixture was diluted with water (100 ml) and the product was extracted into ethyl acetate (3×50 ml). The organic fractions were washed successively with citric acid (aqueous), water, potassium carbonate and brine, then dried (MgSO$_4$) filtered and concentrated. The residue was purified by column chromatography on silica using 70% ethyl acetate in hexane as eluant. The product was recrystallised from ethyl acetate/petrol to afford a crystalline white solid: mp 77°–79° C. MS (CI$^-$) m/z 478 ((M–HF)$^-$, 100%).

EXAMPLE 70

(2S,3S)-3-((3,5-Bis(trifluoromethyl)phenyl)methyloxy-1 -(1-oxo-2-pyrid-4-yl)ethyl-2-phenylpiperidinium hydrochloride The compound of Description 3 was reacted with 4-pyridylacetic acid following the procedure outlined in Example 69. This afforded a colourless oil which was treated with ethereal hydrogen chloride and the solid obtained was recrystallised from benzene/hexane. MS (CI$^+$) m/z 523 (M$^+$+1, 100%). Found: C, 54.67; H, 4.86; N, 4.66; Cl, 6.16. Calcd. for C$_{27}$H$_{24}$F$_6$N$_2$O$_2$.2H$_2$O: C, 54.50; H, 4.91; N, 4.70; Cl, 5.96%.

EXAMPLE 71

(2S,3S)-3-((3,5-Bis(trifluoromethyl)phenyl)methyloxy-1 -(2-oxo-2-pyrid-3-yl)ethyl-2-phenylpiperidine 3-(Bromoacetyl)pyridinium hydrobromide (336 mg) was dissolved in dimethylformamide (3 ml) and to this solution was added the compound of Description 3 (440 mg) followed by potassium carbonate (550 mg). The mixture was stirred at room temperature for 2 h, diluted with water and extracted into ethyl acetate. The organic phase was washed with brine, dried (MgSO$_4$) and evaporated. The residue was purified by chromatography on silica using 70% ether in hexane as eluant and further purified by medium pressure chromatography (Lobar) using ethyl acetate in hexane (60:40) as eluant. $^1$H NMR (250 MHz, DMSO-d$_6$) δ 1.4–1.6 (2H, m), 1.8–1.98 (1H, m, CHH), 2.06–2.2 (1H, m, CHH), 2.5–2.6 (1H, m), 2.9–3.0 (1H, m), 3.54 (1H, d, NCHHCO), 3.62 (1H, brs, CHO), 3.74 (1H, d, CHPh), 3.84 (1H, d, OCHH), 7.2–7.3 (2H, m, ArH), 7.38–7.5 (3H, m, ArH), 7.5 (1H, dd, pyr-H), 7.85 (2H, s, ArH), 7.92 (1H, s, ArH), 8.14 (1H, dt, pyr-H), 8.62 (1H, dd, pyr-H), 8.94 (1H, d, pyr-H).

EXAMPLE 72

3-[(1S)-1-{(2S,3S)-3-((3,5-Bis(trifluoromethylphenyl) methyloxy)-2-phenylpiperidino}ethyl]-1,2,4-triazole This was prepared from the compound of Description 3 and N-formyl-2-chloropropionamidohydrazone following the procedure described in Example 61. The first compound to be eluted from the column (using 3% methanol in dichloromethane as eluant on silica) was isolated and characterised as the title compound: mp 66°–68° C. MS (CI$^+$) m/z 499 ((M+1)$^+$, 100%).

EXAMPLE 73

3-[(1R)-1-{(2S,3S)-3-((3,5-Bis(trifluoromethyl)phenyl) methyloxy)-2-phenylpiperidino}ethyl]-1,2,4-triazole The second product isolated from the column described in Example 72 was recrystallised from ethyl acetate/hexane to afford the title compound: mp 108°–111° C. MS (CI$^+$) m/z 499 ((M+1)$^+$, 100%).

EXAMPLE 74

5-[(1S)-1-{(2S,3S)-3-((3,5-Bis(trifluoromethylphenyl) methyloxy)-2-phenylpiperidino}ethyl]-2, 3-dihydro-3-oxo-1,2,4-triazole This compound was prepared according to the procedure described in Example 35 using the compound of Description 3 and N-carbomethoxy-2-chloropropionamidohydrazone (ClCH(CH$_3$)C(=NH)NHNHCOOCH$_3$) as starting materials. $^1$H NMR (CDCl$_3$) δ 0.94 (3H, d, J=7 Hz), 1.4–1.58 (2H, m), 1.8 (1H, mc), 2.06–2.2 (1H, m), 2.26–2.4 (1H, m), 3.3 (1H, mc), 3.52 (1H, s), 3.64–3.72 (2H, m), 4.06 (1H, d, J=12 Hz), 4.64 (1H, d, J=12 Hz), 7.2–7.38 (3H, m), 7.6–7.7 (2H, m), 7.74 (2H, s), 7.94 (1H, s). MS (CI$^+$) m/z 515 ((M+1)$^+$, 23%).

EXAMPLE 75

3-[{(2S,3S )-3-((3,5-Dichlorophenyl)methyloxy)-2 -phenylpiperidino}methyl]-1,2,4-triazole This was prepared from the compound of Description 11 according to the procedure described in Example 16 to afford the title compound: mp 208°–212° C. MS (CI$^+$) m/z 417 ((M+1)$^+$, 100%).

EXAMPLE 76

5-[{(2R*,3R*)-3-(3,5-Bis(trifluoromethyl)phenyl)methyloxy)- 2-(3-chlorophenyl)piperidino}methyl]-2,3-dihydro-(4H )-3-oxo- 1,2,4-triazole This was prepared from the compound of Description 26 according to the procedure described in Example 35: mp 125°– 127° C. $^1$H NMR (360 MHz, DMSO) δ 1.46–1.52 (2H, m), 1.9–1.95 (1H, m), 2.0–2.2 (2H, m) 2.92 (1H, d, J=15 Hz, NCHH-triazolone), 2.98 (1H, mc), 3.35 (1H, s, CHO), 3.44 (1H, d, J=12 Hz, NCHHtriazolone), 3.50 (1H, brs, CHPh), 3.96 (1H, d, J=12 Hz, OCHH), 4.43 (1H, d, J=12 Hz, OCHH), 7.15–7.22 (2H, m, ArH), 7.37–7.41 (2H, m, ArH), 7.48 (2H, s, ArH), 7.65 (1H, s, ArH). MS (CI$^+$) m/z 535, 537 (M$^+$+1, 100, 30%).

EXAMPLE 77

5-[{(2S,3S)-3-((3,4-Dimethylphenyl)methyloxy)-2 -phenylpiperidino}methyl]-2,3-dihydro-(4H)-3-oxo- 1,2,4-triazole This compound was prepared according to the procedure described in Example 35 using the compound of Description 29 as starting material. $^1$H NMR (CDCl$_3$) δ 1.37–1.55 (2H, m), 1.9– 2.2 (3H, m), 2.1 (3H, s), 2.15 (3H, s), 2.85 (1H, d, J=15 Hz), 2.97 (1H, m), 3.26 (1H, s), 3.51 (1H, s), 3.65 (1H, d, J=15 Hz), 4.06 (1H, d, J=11 Hz), 4.26 (1H, d, J=11 Hz),6.65 (2H, m), 6.9 (1H, d, J=8 Hz), 7.2–7.45 (5H, m), 9.5 (1H, brs).

EXAMPLE 78

5-[{(2S,3S)-3-((3-iPropoxyphenyl)methyloxy)-2-phenylpiperidino}methyl]-2,3-dihydro-(4H)- 3-oxo-1,2,4-triazole This compound was prepared according to the procedure described in Example 35 using the compound of Description 30 as starting material. $^1$H NMR (CDCl$_3$) δ 1.25 (6H, d, J=6 Hz), 1.35–1.55 (2H, m), 1.9–2.2 (3H, m), 2.89 (1H, d, J=15 Hz), 2.99 (1H, d, J=10 Hz), 3.27 (1H, s), 3.51 (1H, s), 3.66 (1H, d, J=15 Hz), 4.1 (1H, d, J=12 Hz), 4.38 (1H, m), 6.48 (1H, d, J=7 Hz), 6.57 (1H, s), 6.66 (1H, d, J=7 Hz), 7.2–7.5 (5H, m).

EXAMPLE 79

5-[{(2S,3S)-3-((3-Fluoro-5-methylphenyl)methyloxy)-2 -phenylpiperidino}methyl]-2,3-dihydro-(4H)-3-oxo-1,2,4-triazole This was prepared by the reaction of the compound of Description 27 according to the procedure outlined in Example 35: mp 228°–229° C. $^1$H NMR (360 MHz, DMSO) δ 1.4–1.55 (2H, m, CH$_2$), 1.8–1.9 (1H, m, CH$_2$), 2.02–2.18 (2H, m, CH$_2$ and NCHH), 2.21 (3H, s, CH$_3$), 2.73 (1H, d, NCHH-het, J=14 Hz), 2.87–2.90 (1H, d, NCHH, J=11 Hz), 3.32–3.40 (1H, m, NCHCHO), 3.41 (1H, d, NCHH-het, J=14 Hz), 3.46 (1H, s, NCHCHO), 3.87 (1H, d, OCHH—Ar, J=12.5 Hz), 4.28 (1H, d, OCHH—Ar, J=12.5 Hz), 6.50–6.55 (2H, m, ArH), 6.80–6.83 (1H, m, ArH), 7.29–7.31 (3H, m, ArH), 7.51–7.53 (2H, m, ArH), 11.18 (1H, s, NH), 11.28 (1H, s, NH). MS (CI$^+$) m/z 397 (M$^+$+1, 10%).

EXAMPLE 80

5-[{3-(3R*)-((3,5-Bis(trifluoromethyl)phenyl)methyloxy)-2-methyl-2-(2R*)-phenylpiperidino}methyl]-2,3-dihydro-(4H)-3 -oxo-1,2,4-triazole This was prepared from the compound of Description 28 according to the procedure outlined in Example 35. $^1$H NMR (360 MHz, MeOD) δ 1.43 (3H, s, CH$_3$), 1.46 (1H, m), 1.91 (3H, m), 2.57 (2H, m), 2.98 (1H, d, J=15 Hz, NCHHtriazolone), 3.21 (2H, m), 3.58 (1H, d, J=15 Hz, NCHH triazolone), 3.72 (1H, d, J=12 Hz, OCHH), 4.36 (1H, d, J=12 Hz, OCHH), 7.18 (1H, t, ArH), 7.25 (2H, t, ArH), 7.37 (2H, s, ArH), 7.53 (1H, s, ArH), 7.56 (1H, s, ArH), 7.71 (1H, s, ArH).

EXAMPLE 81

5-[{(2S,3S)-3-((3,5-Bis(trifluoromethyl)phenyl)methyloxy)-2-(3-fluorophenyl)piperidino}methyl]2,3-dihydro-(4H)-3-oxo-1,2,4-triazole $^1$H NMR (CDCl$_3$) δ 1.42–1.62 (2H, m), 1.84–2.2 (3H, m), 2.86– 3.1 (2H, m), 3.38–3.58 (3H, m), 4.08 (1H, d, J=12 Hz, OCHH), 4.54 (1H, d, J=12 Hz, OCHH), 6.92–7.04 (1H, m, ArH), 7.16–7.32 (3H, m, ArH), 7.54 (2H, s, ArH), 7.76 (1H, s, ArH).

EXAMPLE 82

3-[{(2S,3S)-3-((3,5-Bis(trifluoromethyl)phenyl)methyloxy)-2-phenylpiperidino}methyl]-1,2,4-triazine (a) The compound of Description 3 (1 g) was dissolved in dimethylformamide (8 ml) and N-t-butyloxycarbonyl-2-chloroacetamidrazone (0.6 g) was added, followed by potassium carbonate (0.9 g). The mixture was stirred at room temperature overnight. The mixture was diluted with water, extracted with ethyl acetate and the organic layer was washed with brine, dried (MgSO$_4$) and evaporated. The residue was purified by column chromatography on silica using ethyl acetate as eluant. This afforded the compound as a white solid which was recrystallised from ether-hexane. $^1$H NMR (360 MHz, CDCl$_3$) δ 1.40 (9H, s, (CH$_3$)$_3$), 1.42–1.6 (3H, m), 2.13–2.2 (2H, m), 2.62 (1H, d, J=15 Hz, NCHHC=NH), 3.07–3.10 (1H, m, CHHN), 3.36 (1H, d, J=15 Hz, NCHHC=NH), 3.38 (1H, s, CHO), 3.57 (1H, brs, CHPh), 4.02 (1H, d, J=12 Hz, OCHH), 4.45 (1H, d, J=12 Hz, OCHH), 7.25–7.40 (5H, m, ArH), 7.53 (2H, s, ArH), 7.73 (1H, s, ArH).

(b) The Boc-protected amidrazone (1 g) was dissolved in methanolic hydrogen chloride and stirred for 12 h. The solvent was evaporated and the crude product was used in subsequent reactions without further purification.

(c) The amidrazone hydrochloride of (b) above (200 mg) was dissolved in ethanol (2 ml). Magnesium sulphate was added (100 mg) and the mixture stirred for 30 min. Triethylamine (0.06 ml) was added followed by glyoxal (90 mg, trimeric dihydrate). This mixture was allowed to stir for 12 h. The solvent was removed in vacuo and the residue was dispersed between ethyl acetate and water. The organic layer was dried (MgSO$_4$) and concentrated to afford a brown oil. This was purified by column chromatography on silica using hexane in ethyl acetate (95%) to afford the title compound. $^1$H NMR (360 MHz, CDCl$_3$) δ 1.53–1.72 (2H, m, CH$_2$), 1.98–2.22 (2H, m, CH$_2$), 2.42–2.53 (1H, m, NCHH), 3.14–3.22 (1H, m, NCHH), 3.61 (1H, bs, CHO), 3.74–3.81 (2H, m, NCHPh+OCHH), 4.04 (1H, d, J=12 Hz, NCHHtriazine), 4.19 (1H, d, J=12 Hz, OCHH), 4.47 (1H, d, J=12 Hz, NCHHtriazine), 7.24–7.37 (4H, m, ArH), 7.48–7.6 (4H, m, ArH), 7.70 (1H, s, ArH), 8.6 (1H, s, ArH). MS (CI$^+$) m/z 497 (M$^+$1, 100%). The following examples illustrate pharmaceutical compositions according to the invention.

EXAMPLE 83A

Tablets Containing 1–25 mg of Compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 83B

Tablets Containing 26–100 mg of Compound

|  | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 84

Parenteral Injection

|  | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 85

Topical Formulation

|  | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

We claim:

1. A compound of formula (I), or a pharmaceutically acceptable salt or prodrug thereof:

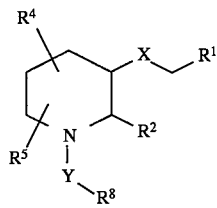

wherein:

X represents O or S;

Y represents a hydrocarbon chain of 1, 2, 3 or 4 carbon atoms which may optionally be substituted by oxo;

R$^1$ represents unsubstituted phenyl or phenyl substituted by 1, 2 or 3 substituents selected from the group consisting of: C$_{1-6}$alkyl, C$_{2-6}$alkenyl, C$_{2-6}$alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ and —CONR$^a$R$^b$;

R$^2$ represents phenyl or benzhydryl, wherein the phenyl or benzhydryl moiety is unsubstituted or substituted by a substituent selected from the group consisting of: C$_{1-6}$alkyl, C$_{1-6}$alkoxy, halo and trifluoromethyl;

R$^4$ and R$^5$ may be present on any available carbon atom of the azacyclic ring and are each independently selected from the group consisting of: H, halo, C$_{1-6}$alkyl, oxo, CH$_2$OR$^a$, CO$_2$R$^a$ and CONR$^a$R$^b$;

R$^8$ represents an aromatic heterocycle selected from the group consisting of: thiazolyl, oxazolyl, oxadiazolyl, thiadiazolyl, isoxazolyl, isothiazolyl and benzoxazolyl, wherein the heterocycle is unsubstituted or substituted with a substituent selected from the group consisting of: $C_{1-6}$alkyl, $C_{1-6}$alkoxy, phenyl, oxo, thioxo, halo, trifluoromethyl, trimethylsilyl, $-NR^aR^b$, $-NR^aCOR^b$, $-CONR^aR^b$, $-CO_2R^a$, $-SR^a$, $-SOR^a$, $SO_2R^a$, and $CH_2OR^a$; and $R^a$ and $R^b$ are each independently selected from the group consisting of: H, trifluoromethyl, $C_{1-6}$alkyl, unsubstituted phenyl and phenyl substituted by a substituent selected from the group consisting of: $C_{1-6}$alkyl, halo and trifluoromethyl.

2. The compound according to claim 1 wherein $R^1$ represents phenyl substituted by one or more substituents selected from the group consisting of: $C_{1-4}$alkyl, trifluoromethyl and halo.

3. The compound according to claim 1 wherein $R^8$ is selected from the group consisting of unsubstituted or substituted oxazolyl, oxadiazolyl and thiadiazolyl.

4. A compound which is selected from the group consisting of:

3-amino-5-[((2R*,3R*)-3-((3,5-bis(trifluoromethyl)phenyl) methyloxy)- 2-phenylpiperidino)methyl]-1,2,4-oxadiazole;

5-[((2R*,3R*)-3-((3,5-bis(trifluoromethyl)phenyl) methyloxy)-2 -phenylpiperidino)methyl]-3-methyl-1,2,4-oxadiazole;

(+)-3-amino-5-[((2S,3S)-3-((3,5-bis(trifluoromethyl) phenyl)methyloxy)- 2-phenylpiperidino)methyl]-1,2,4-oxadiazole;

5-[((2R*,3R*)-3-((3,5-bis(trifluoromethyl)phenyl) methyloxy)-2 -phenylpiperidino)methyl]-3-bromo-1,2, 4-oxadiazole;

5-[((2R*,3R*)-3-((3,5-bis(trifluoromethyl)phenyl) methyloxy)-2 -phenylpiperidino)methyl]-3-dimethylamino-1,2,4-oxadiazole;

3-[((2R*,3R*)-3-((3,5-bis(trifluoromethyl)phenyl) methyloxy)-2 -phenylpiperidino)methyl]-5-dimethylamino-1,2,4-thiadiazole;

2-[((2R*,3R*)-3-((3,5-bis(trifluoromethyl)phenyl) methyloxy)-2 -phenylpiperidino)methyl]-4,7-dimethylbenzoxazole;

2-[((2R*,3R*)-3-((3,5-bis(trifluoromethyl)phenyl) methyloxy)-2 -phenylpiperidino)methyl]benzoxazole;

4-[((2S,3S)-3-((3,5-bis(trifluoromethyl) phenyl)methyloxy)-2 -phenylpiperidino)methyl]oxazole;

4-[((2S,3S)-3-((3,5-bis(trifluoromethyl) phenyl)methyloxy)-2 -phenylpiperidino)methyl]-2-methyl-1,3-thiazole;

3-[((2S,3S)-3-((3,5-bis(trifluoromethyl) phenyl)methyloxy)-2 -phenylpiperidino)methyl]-1,2,4-oxadiazole;

3-[((2S,3S)-3-((3,5-bis(trifluoromethyl) phenyl)methyloxy)-2 -phenylpiperidino)methyl]-5-iodo-1,2,4-thiadiazole;

3-[((2S,3S)-3-((3,5-bis(trifluoromethyl) phenyl)methyloxy)-2 -phenylpiperidino)methyl]-1,2,4-thiadiazole;

3-[((2S,3S)-3-((3,5-bis(trifluoromethyl) phenyl)methyloxy)-2 -phenylpiperidino)methyl]-5-methoxy-1,2,4-thiadiazole;

5-[((2R*,3R*)-3-((3,5-bis(trifluoromethyl)phenyl)methyloxy)-2 -phenylpiperidino)methyl]-3-(N,N-dimethylamino)-1,2,4-thiadiazole;

3-[((2S,3S)-3-((3,5-bistrifluoromethyl)phenyl)methyloxy)-2 -phenylpiperidino)methyl]-5-phenyl-1,2, 4-oxadiazole;

5-[((2R*,3R*)-3-((2-methoxy-3-nitrophenyl)methyloxy)-2 -phenylpiperidino)methyl]-3-methyl-1,2,4-oxadiazole;

3-amino-5-[((2R*,3R*)-3-((5-amino-2-methoxyphenyl)methyloxy)- 2-phenylpiperidino)methyl]-1,2,4-oxadiazole;

and pharmaceutically acceptable salts and prodrugs thereof.

5. A pharmaceutical composition comprising an effective amount of a compound according to claim 1 and a pharmaceutically acceptable carrier therefor.

6. The pharamaceutical composition according to claim 5 further comprising a bronchodilator.

7. A method for the treatment or prevention of a physiological disorder associated with an excess of tachykinins, which method comprises administration to a patient in need thereof of a tachykinin-reducing amount of a compound according to claim 1.

8. The method according to claim 7 for the treatment or prevention of pain or inflammation.

9. The method according to claim 7 for the treatment or prevention of migraine.

10. The method according to claim 7 for the treatment or prevention of arthritis.

11. The method according to claim 7 for the treatment or prevention of postherpetic neuralgia.

12. A method for the treatment of a respiratory disease, which method comprises administration to a patient in need thereof of an effective amount of a compound according to claim 1 and an effective amount of a bronchodilator.

* * * * *